US008642743B2

(12) United States Patent
Herne

(10) Patent No.: US 8,642,743 B2
(45) Date of Patent: Feb. 4, 2014

(54) METHOD FOR REDUCING THE IMMUNE RESPONSE TO A BIOLOGICALLY ACTIVE PROTEIN

(75) Inventor: Nina Herne, Stockholm (SE)

(73) Assignee: AFFIBODY AB, Solna (SE)

( * ) Notice: Subject to any disclaimer, the term of this patent is extended or adjusted under 35 U.S.C. 154(b) by 1369 days.

(21) Appl. No.: 11/547,888

(22) PCT Filed: Apr. 6, 2005

(86) PCT No.: PCT/GB2005/001321
§ 371 (c)(1),
(2), (4) Date: Nov. 15, 2007

(87) PCT Pub. No.: WO2005/097202
PCT Pub. Date: Oct. 20, 2005

(65) Prior Publication Data
US 2008/0187517 A1 Aug. 7, 2008

(30) Foreign Application Priority Data

Apr. 6, 2004 (EP) .................................... 04008299

(51) Int. Cl.
*C07K 1/00* (2006.01)
(52) U.S. Cl.
USPC ......................................................... 530/402
(58) Field of Classification Search
None
See application file for complete search history.

(56) References Cited

U.S. PATENT DOCUMENTS

| 6,010,871 A | 1/2000 | Takahara et al. |
| 2003/0166877 A1 | 9/2003 | Gillies et al. |
| 2004/0001827 A1 | 1/2004 | Dennis |

FOREIGN PATENT DOCUMENTS

| WO | 91/01743 | * | 2/1991 |
| WO | WO 91/00174 | | 2/1991 |
| WO | WO 00/23580 | | 4/2000 |
| WO | 01/45746 | | 6/2001 |

OTHER PUBLICATIONS

Sjolander et al, Journal of Immunological Methods, 201:115-123, 1997.*
Dennis, M.S., et al., "Albumin binding as a general strategy for improving the pharmacokinetics of proteins," J. Biol. Chem., vol. 277, No. 38, Sep. 20, 2002, pp. 35035-35043.
Nord, K., et al., "Binding proteins selected from combinatorial libraries of an alpha-helical bacterial receptor domain," Nature Biotech., vol. 15, Aug. 1997, pp. 772-777.
Yeh, P., et al., "Design of yeast—secreted albumin derivatives for human therapy: biological and antiviral properties of a serum albumin-CD4 genetic conjugate," Proc. Natl. Acad. Sci. USA, vol. 89, Mar. 1992, pp. 1904-1908.
Affibody Ab, Presentation at BioEquity Europe, Edinburgh, UK, May 17-18, 2004.
Nygren, Per-Ake, *Characterization and use of the serum albumin binding region of streptococcal protein G*, Royal Institute of Technology, Department of Biochemistry and Biotechnology, ISBN 91-7170-087-0 (1992).
Rönnmark, Jenny et al., "Construction and characterization of affibody-Fc chimeras produced in Escherichia coli", Journal of Immunological Methods, Vo. 261, pp. 199-211 (2002).
Sandström, K. et al., "*Inhibition of the CD28-CD80 co-stimulation signal by CD28-binding affibody ligand developed by combinatorial protein engineering*", Protein Engineering, vol. 16, No. 9, pp. 691-697 (2003).
Kohita, Hideki et al., "*Binding of Carprofen to Human and Bovine Serum Albumins*", Chemical and Pharmaceutical Bulletin, vol. 42, No. 4, pp. 937-940 (1994).
Hansson, Marianne et al., *An in vitro selected binding protein (affibody) shows conformation-dependent recognition of the respiratory syncytial virus (RSV) G protein:*, Immunotechnology, vol. 4, pp. 237-252 (1999).
Nord, K. et al., "A combinatorial library of an α-helical bacterial receptor domain", Protein Engineering, vol. 8, No. 6

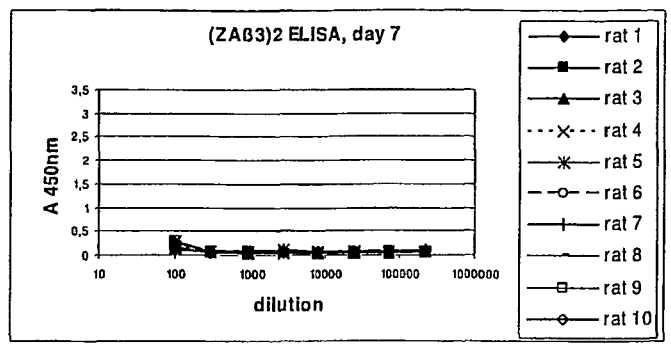
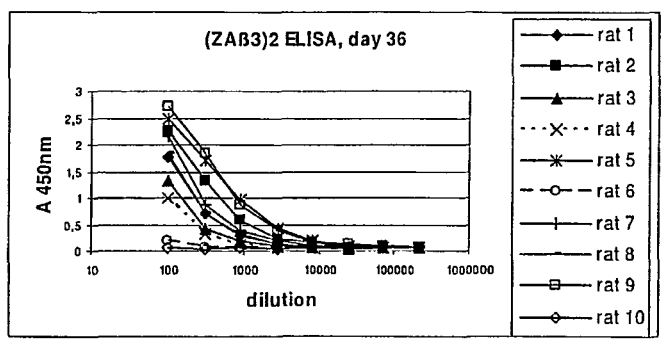
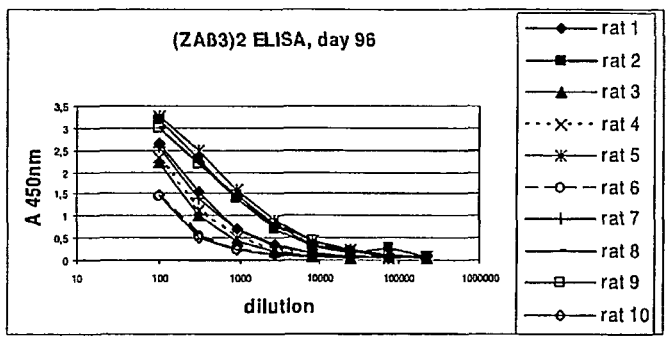
Figure 24

Fig 26

ZTaq4:1-ABD  PB00004  pAY 83

AQHDEAVDNKFNKEKGEVVEIFRLPNLNGRQVKAFIASLYDDPSQSANLLAE
AKKLNDAQAPKSSSLAEAKVLANRELDKYGVSDYYKNLINNAKTVEGVKAL
IDEILAALPSSSATPAKSE*
(SEQ ID NO: 5)

ABD-ZHer2:4  PB00048  pAY262

MGLAEAKVLANRELDKYGVSDYYKNLINNAKTVEGVKALIDEILAALPVDN
KFNKELRQAYWEIQALPNLNWTQSRAFIRSLYDDPSQSANLLAEAKKLNDAQ
APK*  (SEQ ID NO: 6)

ABD-(ZHer2:4)2  PB00053  pAY263

MGLAEAKVLANRELDKYGVSDYYKNLINNAKTVEGVKALIDEILAALPVDN
KFNKELRQAYWEIQALPNLNWTQSRAFIRSLYDDPSQSANLLAEAKKLNDAQ
APKVDNKFNKELRQAYWEIQALPNLNWTQSRAFIRSLYDDPSQSANLLAEAK
KLNDAQAPK*  (SEQ ID NO: 7)

ABD-(ZHer2:4)3  PB00050  pAY264

MGLAEAKVLALRELDKYGVSDYYKDLIDKAKTVEGVKALIDEILAALPVDN
KFNKELRQAYWEIQALPNLNWTQSRAFIRSLYDDPSQSANLLAEAKKLNDAQ
APKVDNKFNKELRQAYWEIQALPNLNWTQSRAFIRSLYDDPSQSANLLAEAK
KLNDAQAPKVDNKFNKELRQAYWEIQALPNLNWTQSRAFIRSLYDDPSQSA
NLLAEAKKLNDAQAPK*  (SEQ ID NO: 8)

ABD-(ZHer2:4)4  PB00051  pAY265

MGLAEAKVLALRELDKYGVSDYYKDLIDKAKTVEGVKALIDEILAALPVDN
KFNKELRQAYWEIQALPNLNWTQSRAFIRSLYDDPSQSANLLAEAKKLNDAQ
APKVDNKFNKELRQAYWEIQALPNLNWTQSRAFIRSLYDDPSQSANLLAEAK
KLNDAQAPKVDNKFNKELRQAYWEIQALPNLNWTQSRAFIRSLYDDPSQSA
NLLAEAKKLNDAQAPKVDNKFNKELRQAYWEIQALPNLNWTQSRAFIRSLY
DDPSQSANLLAEAKKLNDAQAPK*  (SEQ ID NO: 9)

ABD-(ZAβ3)2           PB00106            pAY597

MGSSLAEAKVLANRELDKYGVSDYYKNLINNAKTVEGVKALIDEILAALPLQ
VDNKFNKEMASAGGEIVYLPNLNPDQLSAFIHSLHDDPSQSANLLAEAKKLN
DAQAPKVDNKFNKEMASAGGEIVYLPNLNPDQLSAFIHSLHDDPSQSANLLA
EAKKLNDAQAPKVD* (SEQ ID NO: 10)

(ZAβ3)2           PB00117            pAY596

MGSSLQVDNKFNKEMASAGGEIVYLPNLNPDQLSAFIHSLHDDPSQSANLLA
EAKKLNDAQAPKVDNKFNKEMASAGGEIVYLPNLNPDQLSAFIHSLHDDPSQ
SANLLAEAKKLNDAQAPKVD* (SEQ ID NO: 11)

(Figure 26 continued)

A  Set-up of Mechanistic Study

| Group | Phase 1 Immunizations day 0,3,6,9,12 | Phase 2 Immunizations day 21,24,27,30,33 |
|---|---|---|
| Control | Z | Z |
| Tolerance1 | ABD-Z | Z |
| Tolerance2 | ABD-Z | ABD-Z + Z |
| Anergy | Z | ABD-Z |

$Z = Z_{taq4:5}$

B   -ABD-Mediated Immunity is Due to Passive Suppression

20 μg s.c. d 0, 3, 6, 9,12 (1st molecule) and 21, 24, 27, 30, 33 (2nd molecule); 5 NMRI/group

METHOD FOR REDUCING THE IMMUNE RESPONSE TO A BIOLOGICALLY ACTIVE PROTEIN

CROSS-REFERENCE TO RELATED APPLICATIONS

This application is a U.S. National Stage application of International Application Ser. No. PCT/GB2005/001321 filed Apr. 6, 2005.

FIELD OF THE INVENTION

The present invention relates to methods and uses that reduce the immunogenicity of biologically active proteins. In particular, it relates to the use of a molecule comprising a biologically active protein part and an albumin binding part for preparation of a medicament.

BACKGROUND OF THE INVENTION

Serum Albumin

Serum albumin is the most abundant protein in mammalian sera (40 g/l; ≈0.7 mM in humans), and one of its functions is to bind molecules such as lipids and bilirubin (Peters T, Advances in Protein Chemistry 37:161, 1985). The half-life of serum albumin is directly proportional to the size of the animal, where for example human serum albumin (HSA) has a half-life of 19 days and rabbit serum albumin has a half-life of about 5 days (McCurdy T R et al, J Lab Clin Med 143:115, 2004). Human serum albumin is widely distributed throughout the body, in particular in the intestinal and blood compartments where it is mainly involved in the maintenance of osmolarity. Structurally, albumins are single-chain proteins comprising three homologous domains and totaling 584 or 585 amino acids (Dugaiczyk L et al, Proc Natl Acad Sci USA 79:71 (1982)). Albumins contain 17 disulfide bridges and a single reactive thiol, Cys34, but lack N-linked and O-linked carbohydrate moieties (Peters, 1985, supra; Nicholson J P et al, Br J Anaesth 85:599 (2000)). The lack of glycosylation simplifies recombinant expression of albumin. This property, together with the fact that the three-dimensional structure is known (He X M and Carter D C, Nature 358:209 (1992)), has made it an attractive candidate for use in recombinant fusion proteins. Such fusion proteins generally combine a therapeutic protein (which would be rapidly cleared from the body upon administration of the protein per se) and a plasma protein (which exhibits a natural slow clearance) in a single polypeptide chain (Sheffield W P, Curr Drug Targets Cardiovacs Haematol Disord 1:1 (2001)). Such fusion proteins may provide clinical benefits in requiring less frequent injection and higher levels of therapeutic protein in vivo.

Fusion or Association with HSA Results in Increased In Vivo Half-Life of Proteins Serum albumin is devoid of any enzymatic or immunological function and, thus, should not exhibit undesired side effects upon coupling to a bioactive polypeptide. Furthermore, HSA is a natural carrier involved in the endogenous transport and delivery of numerous natural as well as therapeutic molecules (Sellers E M and Koch-Weser M D, Albumin Structure, Function and Uses, eds Rosenoer V M et al, (Pergamon, Oxford, p 159 (1977)). Several strategies have been reported to either covalently couple proteins directly to serum albumins or to a peptide or protein that will allow in vivo association to serum albumins. Examples of the latter approach have been described e.g. in EP 486 525 and U.S. Pat. No. 6,267,964, in WO01/45746 and in Dennis et al, J Biol Chem 277:35035-43 (2002). The first two documents describe inter alia the use of albumin-binding peptides or proteins derived from streptococcal protein G (SpG) for increasing the half-life of other proteins. The idea is to fuse the bacterially derived, albumin-binding peptide/protein to a therapeutically interesting peptide/protein, which has been shown to have a rapid clearance in blood. The thus generated fusion protein binds to serum albumin in vivo, and benefits from its longer half-life, which increases the net half-life of the fused therapeutically interesting peptide/protein. WO01/45746 and Dennis et al relate to the same concept, but here, the authors utilize relatively short peptides to bind serum albumin. The peptides were selected from a phage displayed peptide library. In Dennis et al, earlier work is mentioned in which the enhancement of an immunological response to a recombinant fusion of the albumin binding domain of streptococcal protein G to human complement receptor Type 1 was found. US Patent application no. 2004/0001827 (Dennis) also discloses the use of constructs comprising peptide ligands, again identified by phage display technology, which bind to serum albumin conjugated to bioactive compounds for tumour targeting. Whilst the constructs are said to have improved pharmacokinetic and pharmacodynamic properties, there is no disclosure or suggestion in this document of a reduction in the immunogenicity of the constructs compared to the unconjugated bioactive compounds. There is no suggestion that further serum albumin-binding conjugate molecules would be desirable.

As an alternative, the therapeutically interesting peptide/protein in question may also be fused directly to serum albumin, as mentioned above and described by Yeh et al (Proc Natl Acad Sci USA 89:1904 (1992)) and Sung et al (J Interferon Cytokine Res 23:25 (2003)). Yeh et al describe the conjugation of two extracellular Ig-like domains (V1 and V2) of CD4 to HSA. The HSA-CD4 conjugate has a retained biological activity of CD4, but the half-life was reported to increase 140 times in an experimental rabbit model, as compared to CD4 alone. Soluble CD4 alone has an elimination half-life of 0.25±0.1 hrs, whereas the elimination half-life of HSA-CD4 was reported to be 34±4 hrs. A prolonged elimination half-life was also observed for interferon-beta (IFN-β) upon conjugation to HSA, as outlined by Sung et al, supra. Here, IFN-β-HSA conjugate was evaluated in primates, and the half-life of IFN-β was reported to increase from 8 hrs alone to 36 to 40 hrs when conjugated to HSA.

Albumin Binding Domains of Streptococcal Protein G

Streptococcal protein G (SpG) is a bifunctional receptor present on the surface of certain strains of streptococci and is capable of binding to both IgG and serum albumin (Björck L et al, Mol Immunol 24:1113 (1987)). The structure is highly repetitive with several structurally and functionally different domains (Guss B et al, EMBO J. 5:1567 (1986)). More precisely, SpG comprises one Ig-binding motif and three serum albumin binding motifs (Olsson A et al, Eur J Biochem 168:319 (1987)).

The albumin-binding protein BB, derived from streptococcal protein G, has 214 amino acid residues and contains about 2.5 of the albumin-binding motifs of SpG (Nygren P-Å et al, J Mol Recognit 1:69 (1988)). It has been shown previously that BB has several properties that make it highly suitable as a fusion partner for peptide immunogens with the purpose of creating powerful vaccines. For example, BB has been fused with repeated structures from the *P. falciparum* malaria antigen Pf155/RESA (M3) (Sjölander A et al, J Immunol Meth 201:115 (1997)), and to a respiratory syncital virus (RSV) (Long) G protein fragment (G2Na) (Power U F et al, Virol 230:155 (1997)). Both BB-M3 and BB-G2Na were able to trigger strong and long-lasting antibody responses against both immunogen fusion moieties in several animal models. BB-M3 induced high titres of antibodies in rabbits after covalent conjugation to immune stimulating complexes (iscoms) (Sjölander A et al, Immunometh 2:79 (1993)) and is immunogenic in mice (Sjölander et al, 1997, supra) and Aotus monkeys (Berzins K et al, Vaccine Res 4:121 (1995)). The observed effect was observed in the presence of a potent adjuvant, e.g. Freund's complete adjuvant (FCA). Furthermore, BB-G2Na induced detectable and protective antibody responses in both mice and man (Power et al, 1997, supra; Power U F et al, J Infect Dis 184:1456 (2001)). In agreement with BB-M3, this effect was observed in the presence of a strong adjuvant, in this case mannitol and aluminum phosphate.

The structure of one of the serum albumin-binding motifs of SpG, designated A3, ABD3 or just ABD ("albumin binding domain"), has been determined (Kraulis P J et al, FEBS Lett 378:190 (1996)). This study revealed a three-helix bundle domain, surprisingly similar in structure to the Ig binding domains of staphylococcal protein A. The SpG domain ABD corresponds to 46 amino acids.

The albumin binding parts of SpG have been epitope mapped closely, as described by Goetsch et al (Clin Diagn Lab Immunol 10:125 (2003)).

Other Albumin-Binding Domains

Albumin-binding proteins are found in other bacteria. For example, naturally occurring albumin-binding proteins include certain surface proteins from Gram[+] bacteria, such as streptococcal M proteins (e.g. M1/Emm1, M3/Emm3, M12/Emm12, EmmL55/Emm55, Emm49/EmmL49 and Protein H), streptococcal proteins G, MAG and ZAG, and PPL and PAB from certain strains of *Finegoldia magna* (formerly *Peptostreptococcus magnus*). See review of Gram[+] surface proteins by Navarre W W and Schneewind O (Microbiol Mol Biol Rev 63:174-229 (1999)), and references contained therein. The characteristics of albumin-binding by some of these proteins have been elucidated further, by e.g. Johansson M U et al (J Biol Chem 277:8114-8120 (2002)); Linhult et al (Prot Sci 11:206-213 (2002), and Lejon S. et al J. Biol. Chem. 279, 41, 2004, 42924-42928).

Clinical Implications of Immunogenicity

Most biologically active proteins, including proteins that are more or less identical to proteins native to the species in question, induce antibody responses upon administration to a significant fraction of subjects. The main factors that contribute to immunogenicity are presence of foreign epitopes, e.g. new idiotypes, different Ig allotypes or non-self sequences, impurities and presence of protein aggregates. In the majority of cases, the induced antibodies have no biological or clinical effects. Where a clinical effect is observed, the most common is a loss of efficacy of the biopharmaceutical.

However, cases with more serious adverse events have been reported. On these occasions, antibodies raised against a protein pharmaceutical cross-reacted with endogenous proteins. Erythropoietin is such an example. When administering erythropoietin to humans, immune responses were induced that led to pure red cell aplasia in the patients (Casadevall N et al, New Eng J Med 346:469 (2002)). The specific antibodies that were generated were of high affinity, and were also shown to cross-react with other forms of erythropoietin such as Eprex®, Epogen® and NeoRecormon®, which indicates that the reactivity was most likely directed against the erythropoietin active site conformation. Another example is thrombopoietin, which, upon administration to humans, resulted in the production of neutralizing antibodies. The antibodies inhibited the activity of endogenous thrombopoietin, which resulted in autoimmune thrombocytopenia (Koren E et al, Curr Pharm Biotech 3:349 (2002)).

Given that the clinical use of biopharmaceuticals often elicits an immune response, immunogenicity is a risk factor to be managed during the development of all biopharmaceutical products. Besides erythropoietin and thrombopoietin mentioned above, several other biopharmaceuticals have also been reported to induce immune responses in patients. Examples are ciliary neurotrophic factor (CNTF), granulocyte-macrophage colony-stimulating factor (GM-CSF), growth hormone (GH), insulin and interferon-beta (IFN-$\beta$). The reasons why the above proteins are observed to generate antibodies in the treated patients differ depending on the product. More precisely, the main factor in the immunogenicity of insulin appeared to have been protein impurities which acted as adjuvants, whereas in the case of IFN-$\beta$ the main factors were believed to be lack of glycosylation when the protein was produced in a bacterial host cell and presence of aggregates due to low solubility (Karpusas M et al, Cell Mol Life Sci 54:1203 (1998)). Before the advent of recombinant human GH, GH from human cadavers was used to treat GH-deficiency in children. Mainly due to a high content of protein impurities, 45% of the children produced antibodies against this first generation of products (Raben M S, Recent Prog Horm Res 15:71 (1959)). When recombinant GH, which includes an extra methionine residue that enables production in *E. coli*, was administered to the patients, the incident of antibodies decreased to 8.5% (Okada Y et al, Endocrinol Jpn 34:621 (1987)). The immunogenicity of GH is more complex than percent identity to the self-protein or lack of immune tolerance, judging from the fact that only one twin developed antibodies to recombinant GH when twins with homozygous GH deletion mutants were treated with the therapeutic protein (Hauffa B P et al, Acta Endocrinol 121:609 (1989)). Recombinant human CNTF was produced with the purpose of treating patients with amyotrophic lateral sclerosis (ALS), since CNTF is believed to enhance the survival of motor neurons. Unfortunately, more than 90% of these patients were tested positive for anti-CNTF antibodies after two weeks of treatment. The clinical effect of the therapeutic protein was severely hampered by the specific antibodies, as shown by the ALS CNTF Study Group report in 1995 (Clin Neuropharmacol 18:515 (1995)). A second generation of CNTF, which contains a truncated C-terminus and is PEGylated, is currently under development.

Furthermore, the immunogenicity of therapeutic antibody molecules is a significant problem which severely limits their widespread and repeated application in treating many diseases.

Different Strategies to Decrease Immunogenicity

Technologies that reduce immunogenicity of proteins are therefore needed. Actually, the importance of such technologies is increasing, since it is becoming more and more common that protein pharmaceuticals have amino acid sequence modifications compared to the naturally occurring protein, or are altogether comprised of amino acid sequences foreign to the subject. One important method to prevent immunogenicity is by optimization of production, purification and formulation of the biopharmaceutical protein to generate soluble, non-aggregated, native protein which is free of contaminating adjuvants. There are several reports on the reduction of immunogenicity of proteins, e.g. human growth hormone (Moore W V et al, J Clin Endocrin Meth 51:691 (1980)) and interferon-$\alpha$ 2a (Hochuli E, J Inter Cyto Res 17:15 (1997)), through improvement of purification and formulation.

Other methods to alter immunogenicity are directed against the actual sequence or structure of the protein in question, and sometimes referred to as "deimmunization methods". Examples of such strategies are epitope neutralization, gene-shuffling, chemical modifications and immune tolerance. Epitope neutralization involves rational identification of dominant T and/or B-cell epitopes using in silico and/or in vitro methods, and subsequent redesign of highlighted sequences to eliminate the dominant epitopes and, hopefully, obtain decreased immunogenicity (Stickler M et al, J Immunother 6:654 (2000); US Patent Application Publication No. 2003/0166877). Another example of deimmunization and gene-shuffling is the humanization of antibody molecules (Kuus-Reichel K et al, Clin Diagn Lab Immunol 1:365 (1994)). The immunogenicity has been reported to drop going from murine to chimeric to fully human antibodies. The evolution of human proteins using DNA gene-shuffling involves homology-dependent recombination of DNA fragments to generate ordered chimaeras of genes. Gene-shuffling could be useful when seeking proteins with reduced immunogenicity and with retained biological activity (Pavlinkova G et al, Int. J. Cancer 94:717 (2001)).

Another method to alter the antigenicity (binding to pre-existing antibodies) and immunogenicity (ability to induce new immune responses) of a protein is to modify the protein chemically. Chemical modifications can be accomplished using covalently bound polymers such as polyethylene glycol (PEG) (Molineux G, Pharmacother 23:3 (2003)) and Dextran (Kobayashi K et al, J Agric Food Chem 49:823 (2001)), or performing neutralization of positive charges with succinic anhydride. PEG is a non-toxic, highly soluble molecule that has been shown to increase the half-life in vivo of proteins covalently bound thereto, and to reduce the immunogenicity of such proteins (Molineux G, supra). The PEG approach is commonly referred to as "PEGylation" of a protein.

Induction of immune tolerance offers a more acceptable means for preventing an immune response than PEGylation, since no chemical additions are made to the therapeutic molecule. The same pharmaceutical is administered, which e.g. ensures a better patient compliance. This approach has been tried for example in the context of administration of factor VIII to patients suffering from hemophilia A. One complication in using factor VIII to treat hemophilia A is the generation of inhibitory antibodies to the therapeutic protein, which is observed in about one-third of all patients (Scharrer I, Haemophilia 5:253 (1999)). Daily injections of large doses of factor VIII together with immunosuppressive agents, which should be given for time periods of from months to years is one strategy that is being pursued in the effort of trying to limit the immune response.

Drawbacks of Current Strategies for Reducing Immunogenicity

The drawbacks of the different approaches to reduce immunogenicity are several. For one thing, it is difficult to achieve covalent attachment to a protein of PEG molecules without obstructing the active sites that are essential for drug efficacy. Avoiding this is a major challenge in PEGylation. There is a great variation in the quality of PEGylated products, and numerous factors have shown to play a part in this variation: the presence or absence of linkers between PEG and the protein; the nature and stability of the bond(s) between the PEG, linker and protein; the impact of PEG attachment on surface charge of the resulting PEGylated protein; the coupling conditions; the requirement of proving that the product is homogeneous; and the relative toxicity of the activated polymer. Moreover, considerable modifications of the prototype method, and also a process of biological optimization have been required to achieve good results in terms of conservation of bioactivity. Any reduction in activity has to be addressed by increasing the treatment dosage, which once again increases the risk of an immune reaction to those molecules. Another drawback of the PEGylation approach is that PEGylated therapeutics increase the cost of treatment by an estimated USD 1000 per month per patient. There has been very little success with polymers other than PEG with regard to improving the pharmacological and immunological properties of therapeutic protein molecules (Burnham N L, Am J Hosp Pharm 51:210 (1994)).

As stated above, the immunogenicity of therapeutic antibody molecules has been addressed using the humanization approach. Humanization has worked well for some murine antibodies, e.g. HERCEPTIN®, which is approved for treatment of some breast cancers. In other cases, humanized antibodies, e.g. CAMPATH®-1H used for treatment of rheumatoid arthritis, still induce an immune response in 60% of the treated patients. Additionally, data from animal studies have shown that rodents are clearly not tolerant of antibodies from the same species and strain (Cobbold S P et al, Meth Enzym 127:19 (1990)) and fully human antibodies are believed to have the potential to evoke anti-idiotypic antibodies just like any other antibody.

Furthermore, the "deimmunization" approach, for example the targeted elimination of T and B-cell epitopes, is not as trivial as it may seem. The algorithms that are available for in silico prediction of epitopes may not be reliable. In the case of predicting B-cell epitopes, this is fairly difficult to do using algorithms, since such epitopes to a great extent are conformational epitopes. T-cell epitopes, on the other hand, are linear, which means that the existing in silico tools are more reliable. Unfortunately, most algorithms are suitable for identifying major histocompatibility complex (MHC) class I associated peptides and not MHC class II associated peptides. Since the latter are more relevant for T-helper cell activation, this is a drawback when seeking to reduce antibody responses. Furthermore, the great polymorphism of MHC molecules makes it difficult to predict, using immunoinformatics, the majority of the T-cell epitopes of any given protein antigen. It is important to remember that epitopes identified by immunoinformatics should always be verified by experimental studies in e.g. in vitro human T-cell stimulation assays. One of the reasons for this is that binding of an immunogenic peptide (i.e. a T-cell epitope) to MHC class II molecules is not sufficient to ensure recognition by a given T cell antigen receptor that has specificity for the peptide. The studies that are necessary for the identification of both T and B-cell epitopes are time-consuming as well as experimentally difficult.

The major disadvantages involved in inducing tolerance to different therapeutics, such as factor VIII exemplified above, are the effects of long-term treatment with immunosuppressive agents (such as sensitivity to infections following suppression of the immune system, and potential toxic effects of the agents) and the high cost involved. It has been estimated that the induction of immune tolerance against factor VIII in a paediatric patient costs nearly USD 1 million.

Despite the existence of strategies for reducing the immunogenicity of biopharmaceuticals and other proteins with biological activity, none of these strategies has proved itself useful in all situations where the reduction or elimination of immunogenicity is desired. Thus, there is a continued need for complementary approaches to the problem.

DISCLOSURE OF THE INVENTION

It is an object of the present invention to meet this need, through the provision of a new way to avoid problems associated with immunogenicity of proteins upon administration thereof to a mammalian subject.

It is a related object of the present invention to reduce, or ideally completely avoid, the generation of antibodies against an administered biopharmaceutical or protein drug.

It is another object of the present invention to exploit the abundance of serum albumin in the mammalian blood for a novel purpose.

In view of these objects, and others which are apparent to the skilled person through the disclosure herein, the present invention, in its various aspects, provides a surprising alternative to the hitherto known alternatives for solving the immunogenicity problem.

Thus, in one aspect, the invention provides the use of a molecule ("the molecule of the invention") comprising at least one moiety which is a biologically active protein and at least one moiety capable of binding to a serum albumin of a mammal, for the preparation of a medicament which elicits no or a reduced immune response upon administration to the mammal, as compared to the immune response elicited upon administration to the mammal of the biologically active protein per se.

In another aspect, the invention provides a method of reducing or eliminating the immune response elicited upon administration of a biologically active protein to a human or non-human mammal, which comprises coupling the polypeptide to at least one moiety capable of binding to a serum albumin of the mammal to form a molecule prior to administration of the molecule ("the molecule of the invention") to the mammal.

In still another aspect, the invention provides an improvement in a method of administering a biologically active protein to a non-human or human mammal, wherein the improvement comprises administering a molecule comprising at least one moiety which is derived from the biologically active protein and at least one moiety capable of binding to a serum albumin of a mammal ("the molecule of the invention"), whereby the molecule elicits no or a reduced immune response as compared to a compound consisting of the biologically active protein per se.

In another aspect of the invention, there is provided a molecule comprising at least one moiety which is a biologically active protein and at least one moiety capable of binding to a serum albumin of a mammal ("the molecule of the invention"), which elicits no or a reduced immune response upon administration to the mammal, as compared to the immune response elicited upon administration to the mammal of the biologically active protein per se.

The invention also provides a composition comprising such a molecule and a pharmaceutically acceptable carrier, and the use of such a molecule in the preparation of a medicament.

As a basis for the different aspects of the invention, it has been surprisingly shown by the present inventors that it is feasible to reduce substantially or even eliminate the immune response against a biologically active protein through covalent coupling of the biologically active protein to a moiety with affinity for a serum albumin. The immune response elicited by administration of the resulting molecule to a mammal is significantly reduced in comparison with that elicited by administration of the biologically active protein without an albumin-binding moiety covalently coupled thereto. This is a surprising observation indeed, especially in view of the fact that the only immunological effect shown in the prior art of coupling a biologically active protein or peptide to an albumin-binding moiety is an increase in the generation of antibodies to an immunogen coupled to the albumin-binding protein BB in the presence of an adjuvant (see Background of the invention).

In one embodiment of the invention, the immune response that is reduced or eliminated is a humoral immune response. The humoral immune response reduced or eliminated in this embodiment may be for example the production of antibodies especially of the IgG isotype.

Without wishing to be bound by any specific theory, it is thought that association of the molecule with serum albumin within the body after administration thereof to the subject mammal results in the immune system of the subject ignoring the molecule, so that an immune response to the molecule does not come about. The equilibrium of albumin association is likely to be shifted very far in the direction of the complex between the molecule and albumin.

The moiety capable of binding to a serum albumin of a mammal may be a protein or peptide, such as a polypeptide or oligopeptide.

The moiety capable of binding to a serum albumin of a mammal may be a naturally occurring polypeptide with the desired ability to interact with a serum albumin. Also, fragments or derivatives of such naturally occurring polypeptides may be used as the albumin-binding moiety, provided of course that the capability of binding albumin is at least partially retained in such a fragment or derivative. As non-limiting examples of naturally occurring polypeptides with albumin-binding activity, mention can be made of certain surface proteins from Gram$^+$ bacteria, such as streptococcal M proteins (e.g. M1/Emm1, M3/Emm3, M12/Emm12, EmmL55/Emm55, Emm49/EmmL49 and Protein H), streptococcal proteins G, MAG and ZAG, and PPL and PAB from certain strains of *Finegoldia magna* (formerly *Peptostreptococcus magnus*). See review of Gram$^+$ surface proteins by Navarre W W and Schneewind O (Microbiol Mol Biol Rev 63:174-229 (1999)), and references contained therein. The characteristics of albumin-binding by some of these proteins have been elucidated further, by e.g. Johansson M U et al (3 Biol Chem 277:8114-8120 (2002)); Linhult et al (Prot Sci 11:206-213 (2002), and Lejon S. et al J. Biol. Chem. 279, 41, 2004, 42924-42928). With the knowledge from these and other publications of what domains are responsible for albumin-binding in these and other proteins, it lies within the normal capability of the person skilled in the field to find a suitable fragment or derivative of any of the listed proteins for use as the albumin-binding moiety in the molecule to be used in the context of the present invention. For example, Protein PAB contains a 53 amino acid residue albumin-binding domain, known as the GA module, which has high sequence homology with the streptococcal ABD is discussed in detail in Lejon et al supra. In particular, this paper discloses the identification of amino acid residues which are important in the binding of the module with human serum albumin. The skilled worker can produce serum albumin-binding moieties having suitable residues which cause the serum albumin-binding moiety to bind to an albumin or to enhance the albumin binding properties of the moiety.

Specifically Lej on et al supra found that the hydrophobic core of the interface between human serum albumin and the GA module is lined with residues Phe-228, Ala-229, Ala-322, Val-325, Phe-326, and Met-329 from human serum albumin, and residues Phe-27, Ala 31, Leu-44, and Ile-48 from GA. The skilled worker may provide a serum-albumin binding moiety that includes alternative amino acid residues which contribute to this interaction surface, e.g. to the hydrophobic core of the interface, or which contribute to the surrounding hydrogen bond interactions so as to enhance binding of the molecule to albumin. Such variants having retained or enhanced affinity for serum-albumin may be constructed based on the information on the complex found in Lejon et al. supra, and comprise alternative surface residues of helix 2 and 3 and of the loops preceding and following helix 2. In addition to altering the binding surface of the crystallized complex by replacing residues directly involved in binding, alternative amino acids may be replaced as a means of obtaining an enhanced binding affinity for serum-albumin due to indirect structural effects or electrostatic steering forces (Low et al., J. Mol. Biol. 260: 359-368, 1996; Schreiber and Fersht, Struct. Biol. 3: 427-431, 1996), or as a means of introducing simultaneous interactions with other portions of serum-albumin. It will be appreciated that the interactions may be in the nature of hydrogen bonds, van der Waals interactions or electrostatic bonds according to the context. All sequence variants resulting from either or both of these approaches for modification are considered as directly related variants of the serum-albumin binding domain described by Kraulis et al supra and used in the examples in this application.

The possible formation of a complex with a fatty acid at the binding interface between human serum albumin is discussed by Lejon et al supra. The applications of the present invention may be modified to enhance binding in the presence or the absence of a fatty acid.

Thus, as stated above and in the Background section, one naturally occurring polypeptide with an albumin-binding function is streptococcal protein G, SpG. Intact SpG, or any albumin-binding domain or fragment or derivative thereof, may therefore be used as the albumin-binding moiety in the molecule used in accordance with the present invention. One example of such a domain with albumin-binding capability is the SpG domain ABD (the 46 amino acid domain also referred to in the prior art as ABD3 or A3. See e.g. Kraulis P J et al, supra). Variants or fragments thereof with retained albumin-binding capacity may of course also be useful. For example, the preferred binding affinity for albumin of a suitable variant or fragment may be as set out below.

As another non-limiting alternative, the moiety capable of binding to a serum albumin of a mammal may be an albumin-binding peptide having from about 5 to about 40 amino acid residues, such as from about 10 to about 20 amino acid residues. Such peptides have been described e.g. in WO01/45746 and in Dennis et al, J Biol Chem 277:35035-43 (2002) in the application of prolonging the half-life of a biologically active protein. In particular, peptides comprising the amino acid sequence DICLPRWGCLW (SEQ ID NO:1) and/or peptides comprising the amino acid sequence DLCLRDWGCLW (SEQ ID NO:2) and/or peptides comprising the amino acid sequence DICLARWGCLW (SEQ ID NO:3) or albumin-binding derivatives of those sequences may be useful as the albumin-binding moiety in the context of the present invention. Specific examples of useful albumin-binding peptides are found in Tables II, III and IV of Dennis et al, supra, and on p 12-13 of WO01/45746, these sections being hereby incorporated by reference into the present disclosure.

The moiety capable of binding to a serum albumin of a mammal may, alternatively, be an organic, non-proteinaceous compound with affinity for the mammalian serum albumin. The moiety is preferably a radical of such an organic compound, which is covalently bound to the biologically active protein moiety. Compounds with affinity for serum albumin are known in the art, and may for example be selected from the group consisting of non-steroidal anti-inflammatory drugs (NSAIDs), such as ibuprofen and carprofen; diclofenac; salicylic acid; warfarin; propofol; and halothane.

In order to obtain an efficient association of the molecule with the serum albumin of the mammal to which it is administered the molecule should have a binding affinity for the albumin such that the $K_D$ of the interaction is $\leq 10^{-6}$ M, such as $\leq 10^{-7}$ M $\leq 10^{-8}$ M, $\leq 10^{-9}$ M, $\leq 10^{-10}$ M, $\leq 10^{-11}$ M, $\leq 10^{-12}$ M, $\leq 10^{-13}$ M or $\leq 10^{-14}$ M. However, in certain circumstances it may be desirable that the albumin binding is not excessively tight, so that the molecule used in accordance with the invention is able to dissociate and perform its intended function in the body. The $K_D$ of a biospecific interaction, such as the one between albumin and the molecule in the present invention, may for example be measured using surface plasmon resonance as known to the skilled person, using for example a Biacore® instrument.

The albumin-binding moiety of the molecule of the invention, and therefore the molecule itself, has an affinity for a serum albumin from a certain mammal. Suitably, the subject to which the molecule is administered belongs to the same mammalian species, so that the association of the albumin-binding moiety and the albumin in the serum of the subject is optimal. Preferably, the albumin-binding moiety is adapted to enhance binding to the serum albumin of a certain mammal. For example, where the mammal is a monkey, the albumin-binding moiety may have enhanced affinity for simian serum albumin. Similarly in the case of a human subject the albumin binding moiety may be modified to enhance the affinity of the molecule of the invention for human serum albumin.

The affinity of the moiety capable of binding to a serum albumin of a mammal may be modified to suit the mammal to be treated. At any time there may be a small amount of the molecule of the invention not bound to albumin. In pharmacokinetic terminology the total exposure over time of non-bound molecule may be expressed as the area under the curve (AUC). It is appreciated by a person within the field of pharmacokinetics that the value of this AUC in a given species will depend both on the affinity to albumin and on the half-life of albumin. In particular, the affinity of the moiety capable of binding to a serum albumin of a mammal, and therefore that of the molecule of the invention, may be arranged so that it is greater for use in mammals such as humans where the half life of the serum albumin is greater. Thus, a higher affinity may be required in a species having a longer circulation time of albumin, such as in a human individual. For example, the affinity of the moiety capable of binding to a serum albumin may be increased by mutating that moiety. Current experiments in the mouse confirm the hypothesis that the AUC should be minimized to avoid an immune response; a mutant having a too low affinity did not yield protection against an immune response. Thus, a higher affinity may be required in a species having a longer circulation time of albumin, such as in a human individual. Therefore, the affinity towards human serum albumin may preferably be increased by mutating the albumin-binding moiety as discussed above.

However, it is possible for one and the same albumin-binding moiety to be capable of binding to serum albumin from different mammalian species. Thus, for example, SpG and its fragments are capable of binding to serum albumins from at least mouse, rat and human beings. In one embodiment of the invention, the reduction or elimination of immune response according to the invention is achieved upon administration of the molecule to a human being. In other embodiments, the effect is exploited in connection with administration to another, non-human, mammal.

The molecule which elicits a reduced immune response also comprises a biologically active protein moiety. The biologically active protein moiety may be any protein that one wishes to administer to a mammal for a given purpose, for example for a therapeutic, preventive or diagnostic purpose. Thus, the term "biologically active protein" comprises any protein or polypeptide, or fragment of a protein or polypeptide that displays a useful biological activity in a mammal to which it is administered, and in general the term protein as used herein embraces polypeptides and fragments of proteins and polypeptides. The biologically active protein moiety may be derived from a protein which is endogenous to the mammal to which the molecule is administered, but may just as well be a heterologous protein or an engineered protein. The biologically active protein moiety may be a soluble molecule or may bind to a receptor. Non-limiting examples of such activities are discussed below.

The activity of the biologically active protein may reside in an ability to interact with a certain target molecule in the body of the mammal in question. Suitably, this target molecule is not a serum albumin of the mammal. There are several examples of biologically active proteins that recognize and bind to target molecules, such as receptors and other proteins, that are present on the surface of cells, or that recognize and bind to target molecules within any of the cells various compartments, or that recognize and bind to target molecules that are present in extracellular body fluids.

Such biologically active proteins have, for example, been shown to be useful in binding to target molecules that are preferentially present on the surface of tumor cells or cancerous cells. A multitude of cancer targets or tumor targets have been described, as has a plethora of antibodies, antibody fragments and other binding molecules with affinity for these targets. As examples of such targets, mention is made of HER2 (involved in certain forms of breast cancer), of CD4, CD20, CD22 and CD74 (all involved in different varieties of lymphoma), and of CEA and EpCAM (present on certain forms of solid tumors). A biologically active protein in the context of the present invention may for example be a protein with an ability to interact with HER2, CD4, CD20, CD22, CD74, CEA or EpCAM as a target molecule.

Further target molecules include toxins. For example a snake venom toxin may be a suitable target and methods of the invention employed to deliver a biologically active moiety which neutralizes the toxin without stimulating a further immune response.

The biologically active protein moiety of the molecule used in accordance with the present invention may also interact with molecules that are not cell-bound, and/or not involved in cancer. Thus, the biologically active protein may for example be a protein that has the ability to block an enzyme, for example to block enzymes involved in the blood clotting cascade or to block elastase. The biologically active protein may, alternatively, have the ability to block hormone or cytokine receptors.

As outlined immediately above, the biologically active protein may be selected from groups of proteins having the ability to interact with a given target molecule. A non-limiting list of such proteins comprises antibodies and fragments and derivatives thereof, staphylococcal protein A and fragments and derivatives thereof, fibronectin and fragments and derivatives thereof, lipocalin and fragments and derivatives thereof, transferrin and fragments and derivatives thereof, and lectins and fragments and derivatives thereof. The naturally occurring forms of many of these molecules have been subjected to protein engineering techniques, such as mutations and alterations in site-directed or randomized approaches, with a view to create novel properties, such as binding affinities for target molecules to which the naturally occurring form does not bind. Any such variant, or derivative, of the proteins listed above may naturally be used as the biologically active protein moiety in the method or use according to the invention. A fragment of any such molecule, whether of the naturally occurring form or of an engineered variant thereof, is also encompassed by the definition, insofar as the activity of the full-length protein is substantially retained in the fragment.

Further suitable biologically active proteins include growth hormone (GH), especially human growth hormone, ciliary neurotrophic factor (CNTF), granulocyte-macrophage colony stimulating factor (GM-CSF), insulin, interferon beta (IFN-β), factor VIII, erythropoietin, GL1P, and thrombopoietin.

The biologically active protein may therefore be staphylococcal protein A, or a fragment or derivative thereof. For example, the IgG-binding B domain, or the Z protein derived therefrom (see Nilsson et al (1987), Prot Eng 1, 107-133, and U.S. Pat. No. 5,143,844), may be useful as the biologically active protein moiety. Based on the Z protein as a basic structure or scaffold, variants with an altered binding affinity have been selected from a library created by random mutagenesis in a combinatorial approach. Such proteins have been characterized in several reports, and commercialized under the designation AFFIBODY® molecules. Representative publications include U.S. Pat. No. 6,534,628, Nord K et al, Prot Eng 8:601-608 (1995) and Nord K et al, Nat Biotech 15:772-777 (1997). Such variants of protein Z derived from staphylococcal protein A are useful as the biologically active protein moiety within the context of the present invention.

The biologically active protein may alternatively, or additionally, exhibit a useful biological activity other than binding to a certain target molecule. For example, it may exhibit an enzymatic activity or a hormone activity.

All of the activities exemplified above may of course have a therapeutic, preventive or diagnostic effect. Thus, it is evident that the activity of the biologically active protein in some cases may be described as a pharmaceutical activity.

Above, the at least two moieties of the molecule to be administered in carrying out the present invention are described as deriving from two different molecular species, which have been coupled covalently in order to provide the molecule which exhibits a reduced or non-existent immune response upon administration. However, it is also contemplated that the two functions of i) biologically useful activity and ii) albumin binding ability may be combined within one and the same molecular species. The use as claimed herein of such molecules also falls within the scope of the present invention. An example of a molecule that illustrates this situation is a protein with a first site, at which site the biologically useful activity resides, and a second site, which is an albumin binding site. In other words the molecule consists of a protein with a first site, which site has a biologically useful activity and corresponds to the biologically active protein, and a second site, which mediates the capability of binding to a serum albumin of a mammal. The biologically useful activity could then be any of the activities discussed above in relation to the biologically active protein moiety. The two sites are spatially separated, and could for example reside on different faces of a protein. A specific such protein is constituted by an albumin-binding domain from streptococcal protein G, which has been provided with an additional binding site at another location on the molecule's surface. At this additional site, the albumin-binding domain may for example have been provided with an ability to interact with any one of the targets discussed above. This additional binding site could be provided through the site-directed or random introduction of amino acid mutations in the protein, such as addition, deletion or replacement of amino acid residues. The resulting protein will exhibit a reduced or eliminated immunogenicity, as compared to the immunogenicity of a protein which is similar in all respects except for the fact that the albumin-binding function is not present.

According to a further aspect of the invention there is provided the constructs $Z_{Taq4:1}$-ABD, ABD-$Z_{her2:4}$, ABD-$(Z_{her2:4})_2$, ABD-$(Z_{her2:4})_3$, ABD-$(Z_{her2:4})_4$, $(Z_{A\beta3})_2$, ABD- and $(Z_{A\beta3})_2$.

According to a further aspect of the invention there is provided a composition comprising a molecule comprising at least one moiety which is a biologically active protein and at least one moiety capable of binding to a serum albumin of a mammal, for the preparation of a medicament which elicits no or a reduced immune response upon administration to the mammal, as compared to the immune response elicited upon administration to the mammal of the biologically active protein per se, as described above and a target molecule or portion or analogue thereof which the biologically active protein binds to or otherwise interacts with. Preferably the target molecule is bound to the biologically active protein moiety.

The invention will now be exemplified by the disclosure of experiments carried out in accordance therewith and with reference to the accompanying drawings FIGS. 1 to 25. The examples are not to be interpreted as limiting the scope of the invention.

BRIEF DESCRIPTION OF THE DRAWINGS

FIG. 24 shows ELISA titration curves for plasma from rats injected with $(ZA\beta3)_2$ as described in Example 6.

FIG. 26 is a table giving the sequence of various constructs in accordance with the invention.

FIG. 27B illustrates results obtained in Example 5.

EXAMPLE 1

Figure 1:
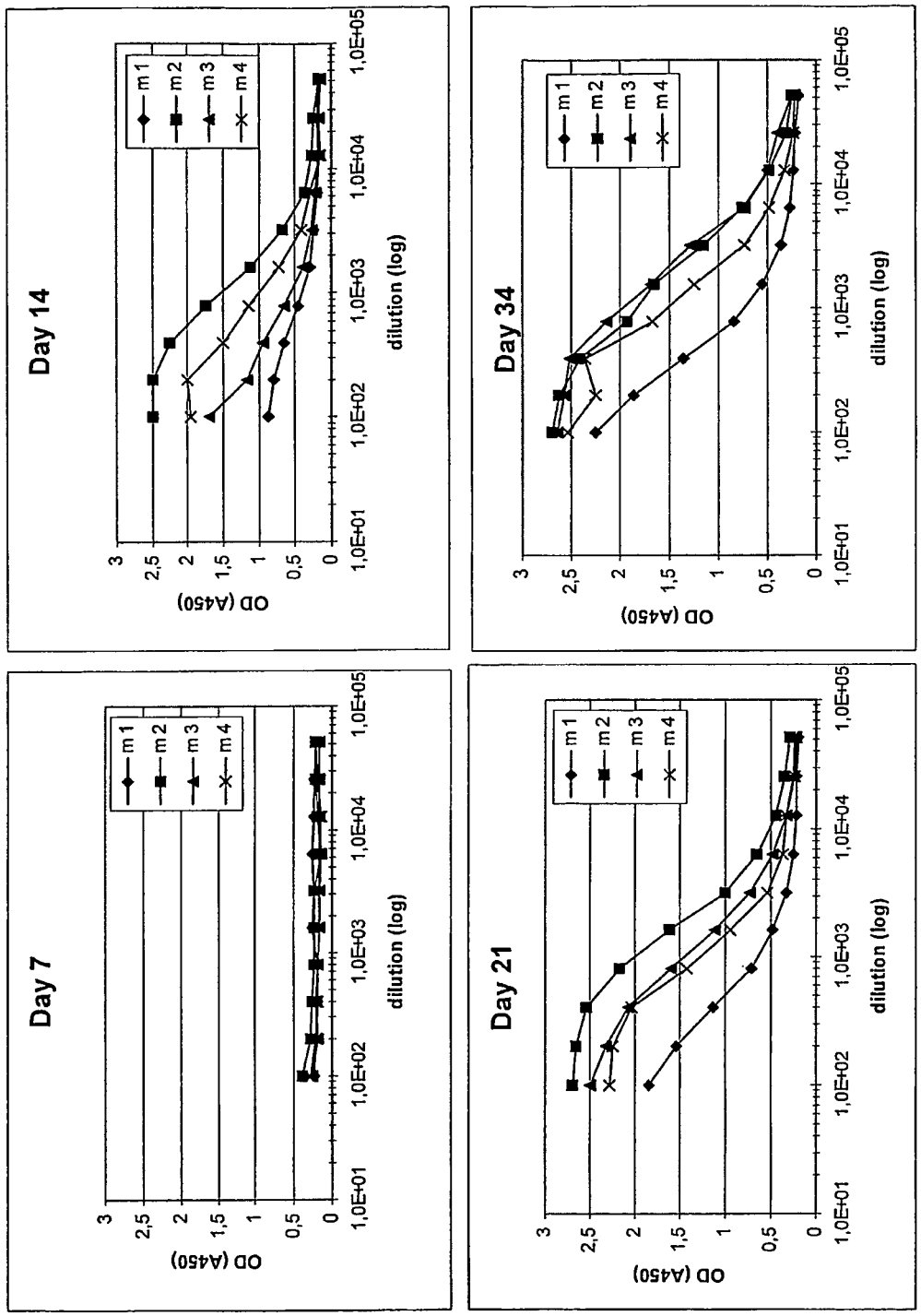
FIG. 1 shows ELISA titration curves for plasma from mice injected with $His_6$-$Z_{Taq4:1}$ as described in Example 1, when analyzed on ELISA plates coated with $His_6$-$Z_{Taq4:1}$.

Humoral Immune Response in Mice Following Administration of Various Molecules Molecules Studied In this Example, the inventive concept was studied through a comparison of the antibody response in mice upon administration of different molecules. The molecules administered were the following:

His$_6$-Z$_{Taq4:1}$—a variant of protein Z, in turn derived from the B domain of staphylococcal protein A. This Z variant was produced using recombinant DNA technology, through the expression of the DNA sequence encoding it, and simultaneously provided with a hexahistidyl tag according to known molecular biology procedures. Z variant Z$_{Taq4:1}$ has previously been selected on the basis of its affinity for Taq DNA polymerase. A description of the Z$_{Taq4:1}$ molecule, including its amino acid sequence and the procedure for selection thereof, is given in Gunneriusson E et al, Protein Eng 12: 10, 873-878 (1999) (see e.g. FIG. 1 in this article). Used for comparative purposes.

Z$_{Taq4:1}$-ABD—a fusion protein between the Z variant Z$_{Taq4:1}$ and the 46 amino acid albumin binding domain (ABD) of streptococcal protein G strain G148 (Kraulis P J et al, FEBS Lett 378:190 (1996))). The fusion protein was prepared through expression of the corresponding DNA sequence in accordance with known molecular biology procedures. Used to illustrate the invention.

Streptokinase—a commercially available bacterial enzyme known to induce strong antibody responses. Purchased from Sigma (cat no S-8026, lot 092K1515) and used as a positive control.

Materials and Methods

Mice and administration schedule: Female NMRI mice (20 mice, plus 2 as a reserve) were used in this experiment. Body weight upon arrival was 20 g. At the start of the immunization experiments, the mice were from 8 to 12 weeks old. The mice were kept and fed in accordance with guidelines from the Swedish Ministry of Agriculture, Food and Fisheries. Food and water were given ad libitum. For the immunization experiment, the mice were split into five groups with four animals in each group. 20 µg of the molecules indicated in Table 1 were administered subcutaneously to each mouse in 0.1 ml NaCl, 0.9%.

TABLE 1

Mouse groups and administered molecules

| Group | Mouse # | Molecule |
|---|---|---|
| 1 | 1-4 | His$_6$-Z$_{Taq4:1}$ |
| 2 | 5-8 | Z$_{Taq4:1}$-ABD |
| 3 | 17-20 | Streptokinase |

The solutions of test molecules were kept frozen at −20° C. and thawed before injection. Repeated injections were given at Day 0, 3, 6, 9, 12 and 21 of the study. Blood samples of 150 µl were taken from the orbital plexus of the mice at Day 0 (preplasma), 7, 14 and 21 of the study. At Day 34 of the study, the mice were sacrificed and the maximal amount of blood obtained. Blood was collected in K$^+$EDTA tubes, and left to stand for one hour after sampling. Thereafter, samples were centrifuged at 6000 rpm for 6 min in order to separate plasma. Plasma was frozen at −20° C. for storage before analysis.

Analysis of plasma samples by specific ELISA: For analysis of plasma from mice receiving one of the molecules above, ELISA-plates (Costar, no 9018) were coated with the corresponding molecule diluted in coating buffer (15 mM Na$_2$HCO$_3$, 35 mM NaHCO$_3$, pH 9.6) to a final concentration of 1 µg/ml. 100 µl of the coating solution was added per well and plates were incubated for 1-3 nights at 4° C. The plates were then washed manually 3 times with deionized water and blocked with 200 µl/well, using PBS (2.68 mM KCl, 1.47 mM KH$_2$PO$_4$, 137 mM NaCl, 8.1 mM Na$_2$HPO$_4$, pH 7.4) with either 1% bovine serum albumin (BSA; from Sigma, cat no A-2153) or 2% dry milk (Semper A B, Stockholm, Sweden), for 1 to 2 hours. The blocking solution was then removed and 100 µl plasma was added to each well, diluted from 1:100 in blocking solution and then in a series of 2-fold dilutions. After 2 hours of incubation, plates were washed manually 3 times with PBS-T (PBS with 0.05% Tween 20; Tween 20 from Acros Organics, cat no 233362500). Thereafter, 100 µl of a secondary antibody, HRP-conjugated goad anti-mouse IgG (Southern Biotech no 1031-05), diluted 1:2000 in blocking solution, was added to each well. Plates were incubated for 1 hour. The three steps (blocking, addition of plasma sample, addition of secondary antibody) were performed on a shaker, and the last step in the dark. The plates were washed manually 5 times wish PBS-T. Subsequently, 100 µl of a substrate solution (ImmunoPure® TMB; Pierce, cat no 34021) was added to each well and plates were subsequently incubated in the dark. Color development was stopped after 15 minutes by addition of 100 µl stop solution (2 M H$_2$SO$_4$; VWR, cat no 14374-1). Plates were read at 450 nm in an ELISA spectrophotmeter (Basic Sunrise, Tecan).

Also included was a standard comprising a pool of mouse plasma previously obtained, containing 210 µg/ml of anti-His$_6$-Z$_{Taq4:1}$ IgG. This pool was used in 2-fold dilution series. The limit of detection in ELISA plates coated with His$_6$-Z$_{Taq4:1}$ was approximately 5 ng/ml.

Analysis of total IgG content in plasma samples: For determination of the total amount of IgG in the samples, quantitative ELISA analyses were performed using a Mouse IgG ELISA Quantitation kit (Bethyl, cat no E90-131), according to the manufacture's instructions. In brief, ELISA plates were coated with anti-mouse IgG provided by the manufacturer. The plasma to be investigated and the standard plasma were added in 2-fold dilution series beginning with 2000 ng/ml. The detection antibody was diluted 1:100000 (anti-mouse IgG, HRP conjugate; provided by the manufacturer) in blocking buffer. The ELISA analyses were developed using ImmunoPure® TMB as described above.

Purification of IgG: IgG was purified from a pool of Day 34 plasma obtained from mice injected with Z$_{Taq4:1}$-ABD. The pool was diluted 12.5 times with PBS-T before loading on a HiTrap column provided with an IgG-specific affinity ligand derived from staphylococcal protein A. The column had been previously equilibrated with PBS-T. The column was washed until absorbance values reached zero, and bound IgG was eluted using elution buffer (0.2 M glycine, 1 mM EGTA, pH 2.8). For neutralization, Tris base to a concentration of 50 mM and 1/10 volume of 10×PBS were added.

Data analysis: ELISA values were obtained using the Magellan software from Tecan. The values were exported to Microsoft Excel for analysis. IgG concentrations were calculated by comparison with a standard curve using the Xlfit.3 program (world wide web.idbs.com). The values/curves obtained with the standard pool of anti-His$_6$-Z$_{Taq4:1}$ IgG and the Bethyl standard plasma were used for determination of specific and total IgG, respectively.

Results His$_6$-Z$_{Taq4:1}$: Mice #1-#4 were injected with His$_6$-Z$_{Taq4:1}$. Plasma samples obtained before immunization (pre-plasma), and after 7, 14, 21 and 34 days were analyzed for presence of His$_6$-Z$_{Taq4:1}$ specific antibodies, as described in the method section. ELISA plates were blocked with 1% BSA. There were no antibodies against the injected molecule in preplasma. All four mice responded by generating a moderate antibody response against the injected protein. The titre of specific antibodies rose steadily during the treatment, with the highest titre at Day 34. FIG. 1 shows the titration curves of individual plasma samples, plotted against OD values at 450 nm.

Total IgG concentration was determined using the Bethyl-ELISA, and the concentration of IgG specific for His$_6$-Z$_{Taq4:1}$ was determined using the standard pool as described above. The results are presented in Table 2. The concentration of specific antibodies increased 50-500 times during the 34 days of treatment. Taking the total IgG concentration into account, the specific antibodies constituted about 1-4% of the total amount of IgG.

TABLE 2

Total and specific IgG in plasma following administration of His$_6$-Z$_{Taq4:1}$

| Mouse # | Molecule | Total IgG (µg/ml) Day: | | Specific IgG (µg/ml) Day: | | | | |
|---|---|---|---|---|---|---|---|---|
| | | 0 | 34 | 0 | 7 | 14 | 21 | 34 |
| 1 | His$_6$-Z$_{Taq4:1}$ | 2100 | 550 | ND* | ND* | ND* | 3.4 | 5.2 |
| 2 | His$_6$-Z$_{Taq4:1}$ | 320 | 1200 | ND* | ND* | 13 | 21 | 29 |
| 3 | His$_6$-Z$_{Taq4:1}$ | 350 | 900 | ND* | ND* | 1.8 | 13 | 37 |
| 4 | His$_6$-Z$_{Taq4:1}$ | 810 | 740 | ND* | ND* | 6.9 | 12 | 17 |

*ND—Not detectable (below detection limit)

Figure 2:
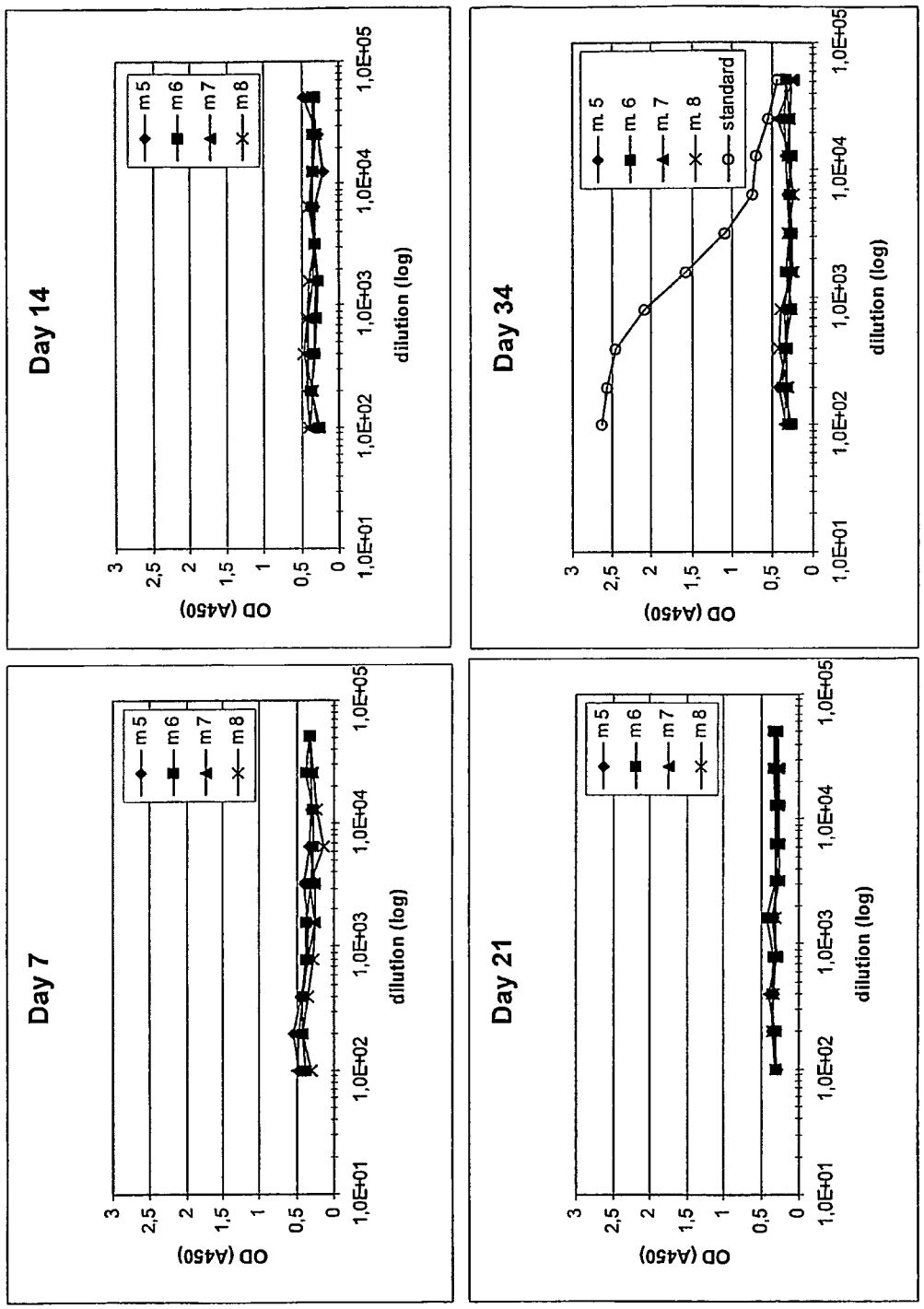
FIG. 2 shows ELISA titration curves for plasma from mice injected with $Z_{Taq4:1}$-ABD as described in Example 1, when analyzed on ELISA plates coated with $Z_{Taq4:1}$-ABD. In the panel showing plasma titres at Day 34 of the experiment, a standard curve has been included.

Z$_{Taq4:1}$-ABD: Mice #5-#8 were injected with Z$_{Taq4:1}$-ABD. Plasma samples obtained before immunization (pre-plasma, data not shown), and after 7, 14, 21 and 34 days were analyzed for presence of antibodies specific for Z$_{Taq4:1}$-ABD, as described in the method section. ELISA plates were blocked with 1% BSA. FIG. 2 shows the results obtained from individual plasma samples, plotted against OD values at 450 nm. In summary, no specific antibodies were detected against the injected Z$_{Taq4:1}$-ABD.

Figure 3:
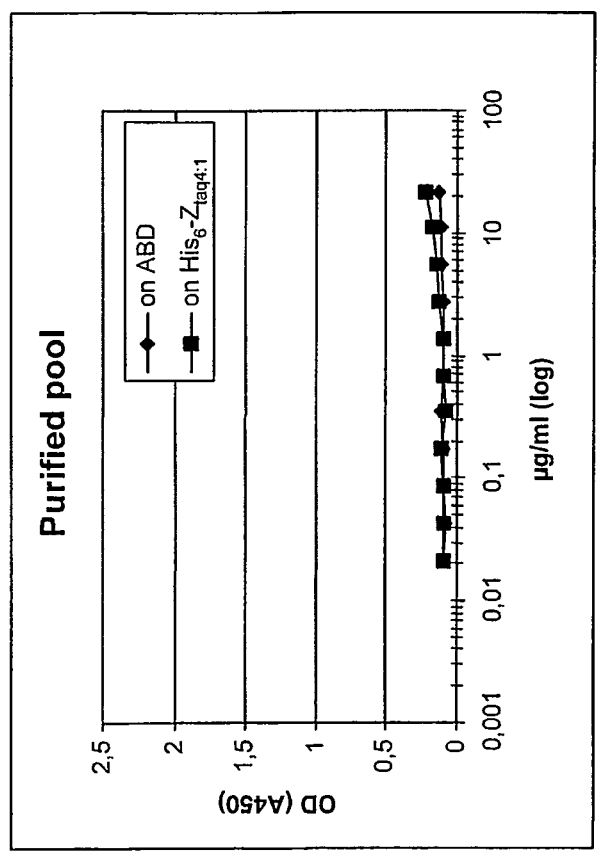
FIG. 3 shows ELISA titration curves for IgG purified from plasma from mice injected with $Z_{Taq4:1}$-ABD as described in Example 1, when analyzed on ELISA plates coated with ABD or $His_6$-$Z_{Taq4:1}$.

The risk that mouse serum albumin interacted with the ABD moiety of the protein coated in the ELISA wells, and thus sterically hindered mouse antibodies from specific binding to the Z$_{Taq4:1}$-ABD molecules, was tested. In the first approach, ABD was avoided by coating with His$_6$-Z$_{Taq4:1}$. Plasma from day 34 were tested, and results showed no specific interaction between mouse antibodies and His$_6$-Z$_{Taq4:1}$ (data not shown). Another approach was to remove albumin from the plasma. Total IgG was therefore purified from a pool of Day 34 plasma from mice #5-#8 using a HiTrap column as described in the "Materials and methods" section. The IgG fraction was tested on plates coated with ABD or His$_6$-Z$_{Taq4:1}$, and the results are shown in FIG. 3. In summary, no binding could be detected between mouse antibodies and the His$_6$-Z$_{Taq4:1}$ or ABD coated surfaces.

Total IgG concentration was determined using the Bethyl-ELISA as described above, and the results are presented in Table 3.

TABLE 3

Total IgG in plasma following administration of Z$_{Taq4:1}$-ABD

| | | Total IgG (µg/ml) Day: | |
|---|---|---|---|
| Mouse # | Molecule | 0 | 34 |
| 5 | Z$_{Taq4:1}$-ABD | 270 | 320 |
| 6 | Z$_{Taq4:1}$-ABD | 280 | 370 |
| 7 | Z$_{Taq4:1}$-ABD | 1000 | 950 |
| 8 | Z$_{Taq4:1}$-ABD | 1400 | 1200 |

Figure 4:
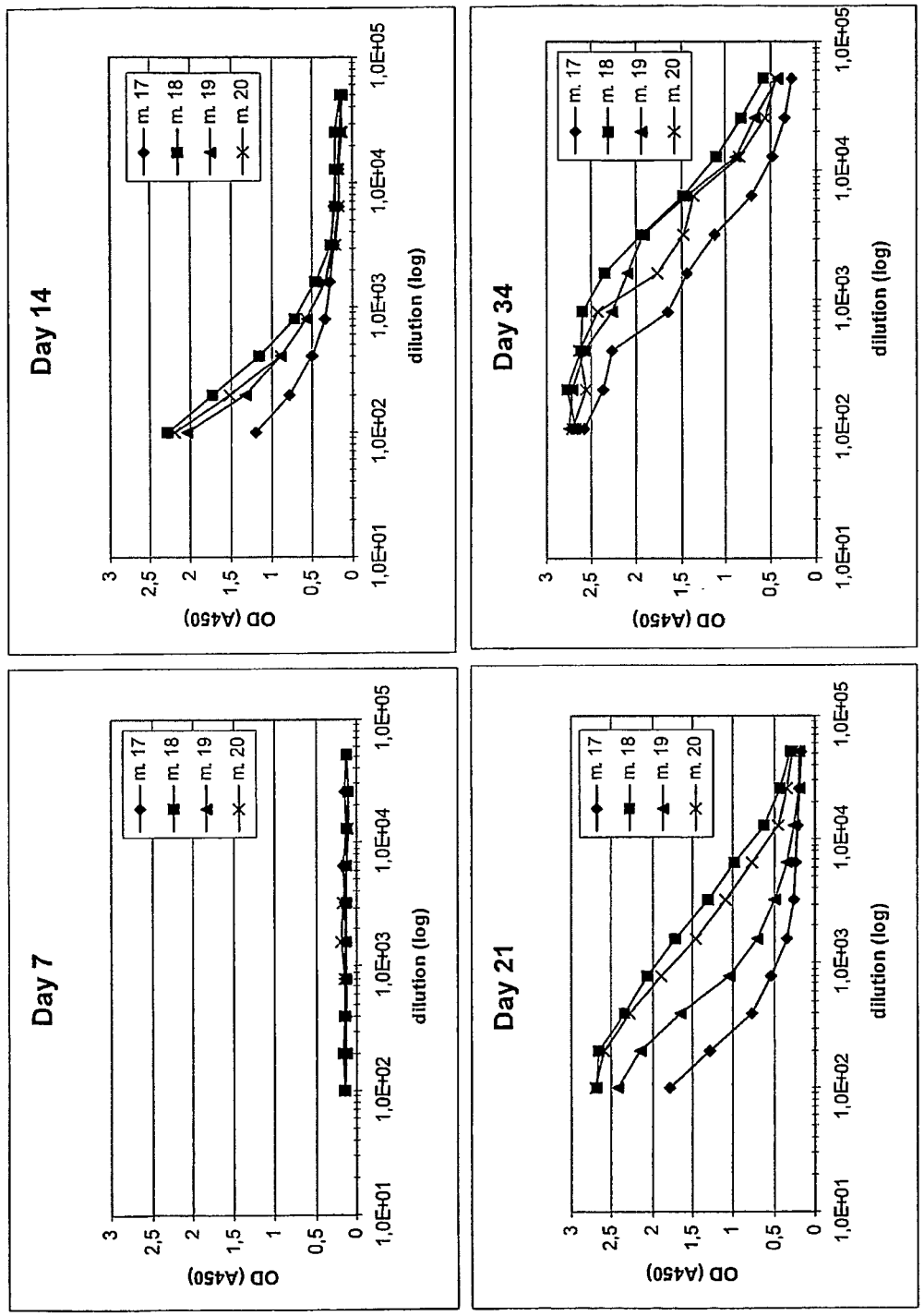
FIG. 4 shows ELISA titration curves for plasma from mice injected with streptokinase as described in Example 1, when analyzed on ELISA plates coated with streptokinase.

Streptokinase: Mice #17-#20 were injected with streptokinase, a bacterial enzyme that prevents clotting of blood and is known to induce strong antibody responses. Plasma samples obtained before injection (preplasma, not shown), and after 7, 14, 21 and 34 days were analyzed for the presence of streptokinase-specific antibodies, as described in the method-section. The ELISA plates were blocked with 2% dry milk. FIG. 4 shows the results obtained from individual plasma samples, plotted against OD values at 450 nm. As shown in FIG. 4, streptokinase induced an antibody response that increased during the treatment period. At Day 34, high titres of streptokinase-specific antibodies were detected in all four mice.

Total IgG concentration was determined using the Bethyl-ELISA as described above, and the results are presented in Table 4. The total IgG concentration was in all but one case considerably higher at death bleeding than in preplasma, implying a normal maturation of the immune system and/or an ongoing immune response.

TABLE 4

Total IgG in plasma following administration of streptokinase

| | | Total IgG (µg/ml) Day: | |
|---|---|---|---|
| Mouse # | Molecule | 0 | 34 |
| 17 | Streptokinase | 1500 | 1100 |
| 18 | Streptokinase | 1200 | 4800 |
| 19 | Streptokinase | 3000 | 6300 |
| 20 | Streptokinase | 280 | 4100 |

Endpoint titres: The concentration of antibodies specific for the administered molecule was determined only in plasma from mice injected with His$_6$-Z$_{Taq4:1}$, due to the lack of suitable standards for the other proteins. For this reason, endpoint titres were used for comparisons between different injected proteins. The endpoint titre was defined as the dilution where the OD value equaled two times the background, the background being the OD value obtained in preplasma from the same mouse. Table 5 shows the endpoint titres for each mouse. To summarize the results, the endpoint titres after immunization with streptokinase were considerably higher than those obtained with different Z variants. Of particular relevance to the present invention was that antibody titres after immunization with Z$_{Taq4:1}$-ABD were not detectable.

TABLE 5

Endpoint titres of antibodies following administration of various molecules to mice

| His$_6$-Z$_{Taq4:1}$ | | Z$_{Taq4:1}$-ABD | | Streptokinase | |
|---|---|---|---|---|---|
| Mouse # | Endpoint titre | Mouse # | Endpoint titre | Mouse # | Endpoint titre |
| 1 | 2700 | 5 | No value | 17 | 78 000 |
| 2 | 14 000 | 6 | No value | 18 | Value out of range |
| 3 | 16 000 | 7 | No value | 19 | 110 000 |
| 4 | 8000 | 8 | No value | 20 | 730 000 |

Discussion

To study the effect of administration of different molecules on initiation of specific B-cell activation and antibody generation in an animal model, NMRI mice were injected subcutaneously with different molecules. In order to simulate a normal treatment cycle, six injections of adequate doses without adjuvant were administered to the mice (three days apart, with a booster injection at Day 21). Plasma from treated animals were analyzed for the presence of antibodies of IgG isotype with specificity for the injected molecules. In addition, levels of total IgG content of all animals were determined in preplasma and on the day of death bleeding (Day 34).

As shown in the "Results" section above, His$_6$-Z$_{Taq4:1}$ induced specific IgG responses in the studied animals. The antibody responses were low to moderate (5 to 37 µg/ml at Day 34), with the most apparent increase after booster injection at Day 21 (2-20 times increase). The responses peaked at Day 34.

Importantly, plasma from animals injected with Z$_{Taq4:1}$-ABD did not show any specific binding to the injected molecules as determined by ELISA. This result was in great contrast to the specific IgG titres observed when analyzing His$_6$-Z$_{Taq4:1}$, i e the same Z sequence fused to His$_6$ instead of ABD. All five time-points analyzed were negative for target-specific mouse IgG antibodies. The Limit of Detection (LOD) in the ELISA was about 5 ng/ml.

Streptokinase, a bacterial protein considered to be a strong immunogen, was used as positive control in the studies. As expected, high specific IgG responses were observed in animals injected with streptokinase.

In conclusion, the injected proteins can be ranked in the following manner, according to their ability to evoke specific IgG responses: streptokinase>>His$_6$-Z$_{Taq4:1}$>>Z$_{Taq4:1}$-ABD. The most interesting and relevant result was that the fusion of ABD to Z$_{Taq4:1}$ resulted in a specific IgG response that could not be detected.

EXAMPLE 2

Humoral Immune Response in Mice Following Administration of Different Molecules at Various Frequencies Molecules Studied In this Example, the inventive concept was again studied through a comparison of the antibody response in mice upon administration of different molecules. The molecules administered were the following:

His$_6$-Z$_{Taq4:5}$—a variant of protein Z, in turn derived from the B domain of staphylococcal protein A. The Z$_{Taq4:5}$ variant was produced using recombinant DNA technology, through expression of the DNA sequence encoding it, and simultaneously provided with a hexahistidyl tag according to known molecular biology procedures. Z$_{Taq4:5}$, including its selection and amino acid sequence, is described in Gunneriusson E et al, supra, where it is denoted Z$_{Taq\ S1\text{-}1}$. Used for comparative purposes.

Z$_{Taq4:1}$-ABD—as described in Example 1. Used to illustrate the invention.

ABD—the albumin binding domain (ABD) of streptococcal protein G strain G148 (see above for references). Prepared through expression of the corresponding DNA sequence in accordance with known molecular biology procedures. Used for comparative purposes.

Materials and Methods

Mice and administration schedule: Female NMRI mice (40 mice, plus 2 as a reserve) were used in this experiment. Body weight upon arrival was 20 g. At the start of the immunization experiments, the mice were from 8 to 12 weeks old. The mice were kept and fed in accordance with guidelines from the Swedish Ministry of Agriculture, Food and Fisheries. Food and water were given ad libitum. For the immunization experiment, the mice were split into seven groups according to Table 6. 20 µg of the molecules indicated in Table 6 were administered subcutaneously to each mouse in 0.1 ml NaCl, 0.9%.

TABLE 6

Mouse groups and administered molecules

| Group | Mouse # | Molecule |
|---|---|---|
| 1 | 53-60 | His$_6$-Z$_{Taq4:5}$ |
| 2 | 61-68 | Z$_{Taq4:1}$-ABD |
| 3 | 69-76 | ABD |
| 4 | 82-85 | His$_6$-Z$_{Taq4:5}$ |
| 5 | 86-89 | Z$_{Taq4:1}$-ABD |
| 6 | 90-93 | ABD |

The solutions of test molecules were kept frozen at −20° C. and thawed before injection. The mice of groups 1-3 received subcutaneous injections at Day 0, 7 and 21 of the study (scheme 1, low frequency). The mice of groups 4-6 received subcutaneous injections at Day 0, 1 and 21 of the study (scheme 2, high frequency). Blood samples of 150 µl were taken from the orbital plexus of the mice at Day 0 (pre-plasma), 7, 14 and 21 of the study. At Day 34 of the study, the mice were sacrificed and the maximal amount of blood obtained. Blood was collected in K$^+$ EDTA tubes, and left to stand for one hour after sampling. Thereafter, samples were centrifuged at 6000 rpm for 6 min in order to separate plasma. Plasma was frozen at −20° C. for storage before analysis.

Analysis of plasma samples by specific ELISA: For analysis of plasma from mice receiving one of the molecules above, ELISA-plates (Costar, no 9018) were coated with the corresponding molecule diluted in coating buffer (15 mM Na$_2$HCO$_3$, 35 mM Na—HCO$_3$, pH 9.6) to a final concentration of 1 µg/ml. 100 µl of the coating solution was added per well and plates were incubated for 1-3 nights at 4° C. The plates were then washed manually 3 times with deionized water and blocked with blocking buffer (200 µl/well; PBS (2.68 mM KCl, 1.47 mM KH$_2$PO$_4$, 137 mM NaCl, 8.1 mM Na$_2$HPO$_4$, pH 7.4) with 0.5% casein (Sigma, cat no C-8654), for 1 to 2 hours. The blocking buffer was then removed and 100 µl plasma was added to each well, diluted from 1:100 in blocking solution and then in a series of 2-fold dilutions. Also included was a standard comprising a pool of mouse plasma previously obtained, containing 210 µg/ml of anti-His$_6$-Z$_{Taq4:1}$ IgG. This pool was used in 2-fold dilution series. The limit of detection in ELISA plates coated with His$_6$-Z$_{Taq4:1}$ was approximately 5 ng/ml.

After 2 hours of incubation, plates were washed manually 3 times with PBS-T (PBS with 0.05% Tween 20). Thereafter, 100 µl of a secondary antibody, HRP-conjugated goat anti-mouse IgG (Southern Biotech no 1031-05), diluted 1:2000 in blocking buffer, was added to each well. Plates were incubated for 1 hour. All steps were performed on a shaker, and the last step in the dark. The plates were washed manually five times with PBS-T. Subsequently, 100 µl of a substrate solution (ImmunoPure® TMB; Pierce, cat no 34021) was added to each well and plates were subsequently incubated in the dark. Color development was stopped after 15 minutes by addition of 100 µl stop solution (2 M H$_2$SO$_4$; VWR, cat no 14374-1). Plates were read at 450 nm in an ELISA spectrophotometer (Basic Sunrise, Tecan) using Magellan software.

Analysis of total IgG content in plasma samples: For determination of the total amount of IgG in the samples, quantitative ELISA analyses were performed using a Mouse IgG ELISA Quantitation kit (Bethyl, cat no E90-131), according to the manufacturer's instructions. In brief, ELISA plates were coated with anti-mouse IgG (1 µg/ml) provided by the manufacturer. The plasma to be investigated and the standard plasma were added in 2-fold dilution series. The standard plasma was diluted from 2000 ng/ml. The detection antibody was used at a dilution of 1:100000 (anti-mouse IgG, HRP conjugate; provided by the manufacturer) in blocking buffer. The ELISA analyses were developed using ImmunoPure® TMB as described above.

Data analysis: ELISA values were obtained using the Magellan software from Tecan. The values were exported to Microsoft Excel for analysis. IgG concentrations were calculated by comparison with a standard curve using the Xlfit.3 program (world wide web.idbs.com). The values/curves obtained with the standard pool of anti-His$_6$-Z$_{Taq4:1}$ IgG and the Bethyl standard plasma were used for determination of specific and total IgG, respectively.

Results

Figure 5:
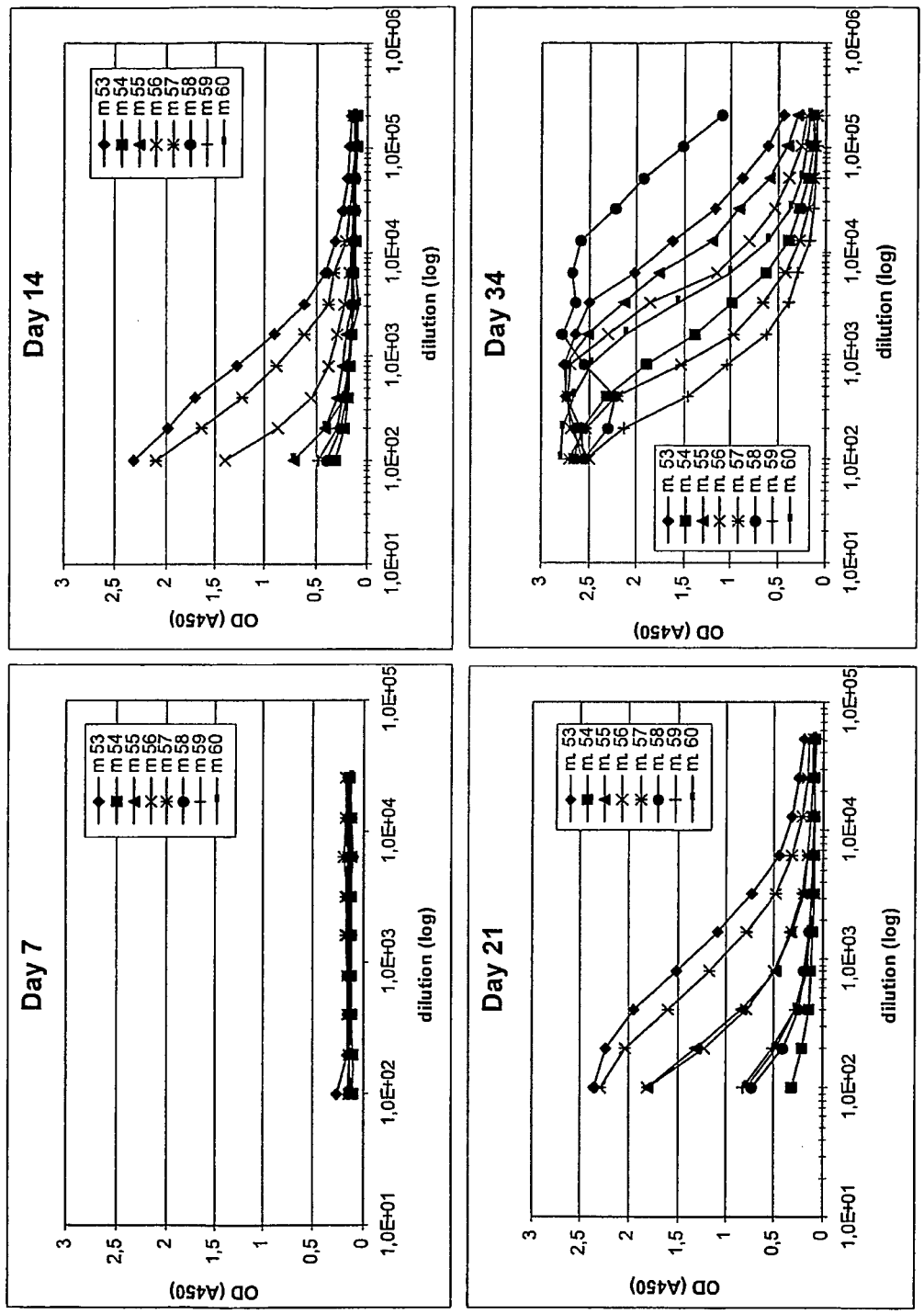
FIG. 5 shows ELISA titration curves for plasma from mice injected with $His_6$-$Z_{Taq4:5}$ following scheme 1 as described in Example 2, when analyzed on ELISA plates coated with $His_6$-$Z_{Taq4:5}$.

His$_6$-Z$_{Taq4:5}$: Eight mice (#53-#60) were injected with His$_6$-Z$_{Taq4:5}$ at 20 µg/mouse and injection, according to scheme 1 (see above). Plasma samples obtained before (preplasma), during (Day 7, 14, 21) and after (Day 34) injections were analyzed for presence of His$_6$-Z$_{Taq4:5}$ specific antibodies as described above. The results are shown in FIG. 5. There were no His$_6$-Z$_{Taq4:5}$ specific antibodies in preplasma (data not shown) or at Day 7 (FIG. 5). The number of positive plasma had increased by Day 14 and 21.

At Day 34, all plasma samples contained His$_6$-Z$_{Taq4:5}$ specific antibodies, although the level varied considerably between individual mice.

Figure 6:
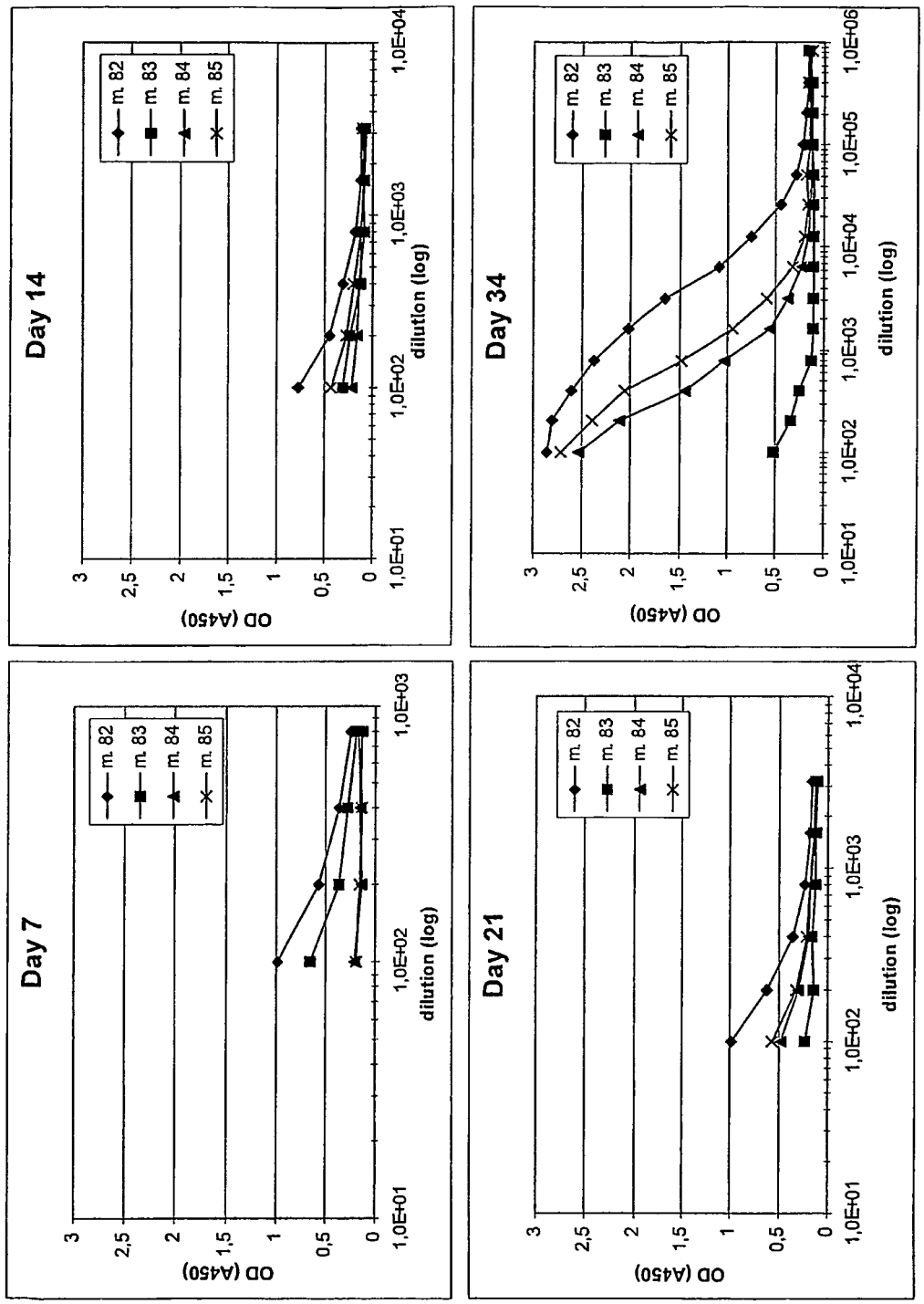
FIG. 6 shows ELISA titration curves for plasma from mice injected with $His_6$-$Z_{Taq4:5}$ following scheme 2 as described in Example 2, when analyzed on ELISA plates coated with $His_6$-$Z_{Taq4:5}$.

Four mice (#82-#85) were injected with His$_6$-Z$_{Taq4:5}$ according to scheme 2 (see above). Plasma samples obtained before (preplasma), during (Day 7, 14, 21) and after (Day 34) injection were analyzed for presence of His$_6$-Z$_{Taq4:5}$ specific antibodies as described above. The results are shown in FIG. 6. There were no His$_6$-Z$_{Taq4:5}$ specific antibodies in preplasma (data not shown). Antibodies against His$_6$-Z$_{Taq4:5}$ were found at low levels in some, but not all, plasma samples already from Day 7. The number of positive plasma samples and the titre did not increase at Day 14 and 21 as for scheme 1. At Day 34, all but one plasma sample had levels of His$_6$-Z$_{Taq4:5}$ specific antibodies that were high compared to those of Day 21.

The concentration of specific IgG was determined using the standard pool of anti-His$_6$-Z$_{Taq4:1}$ IgG (see method section). This pool has previously been shown to contain 210 µg/ml of His$_6$-Z$_{Taq4:1}$ specific antibodies. Concentrations were calculated using the XLfit program and the one-site, dose-response formula. Both samples and standard were tested as singles, and the standard variation of the method is therefore unknown. In addition, the mathematical formula chosen for calculation also affects the values, and the variation depending on the formula has not been calculated. Thus, the concentrations given in the table below should be considered as relative, rather than absolute, values. Table 7 shows the concentration of His$_6$-Z$_{Taq4:5}$ specific antibodies in plasma from individual mice. As shown in the titration analysis above, the concentration of specific IgG at Day 34 varied considerably between individual mice in both groups. The seemingly higher concentration in the scheme 1 group was not statistically significant when tested with Student's T test (TTEST function, Microsoft Excel).

Total IgG concentrations were also determined in Day 34 plasma samples from the His$_6$-Z$_{Taq4:5}$ injected mice, using quantitative ELISA as described above. The results are presented in Table 7 (column 7).

TABLE 7

Total and specific IgG in plasma following administration of His$_6$-Z$_{Taq4:5}$

| | | Specific IgG (µg/ml) | | | | Total IgG | % specific IgG of total |
|---|---|---|---|---|---|---|---|
| Scheme | Mouse # | Day 7 | Day 14 | Day 21 | Day 34 | (µg/ml) Day 34 | IgG Day 34 |
| 1 | 53 | ND* | 20 | 20 | 260 | 1100 | 26 |
| | 54 | ND | ND | ND | 20 | 1500 | 1 |
| | 55 | ND | ND | 20 | 160 | 1500 | 9 |
| | 56 | ND | 30 | 30 | 90 | 740 | 9 |
| | 57 | ND | 50 | 50 | 10 | 1500 | 1 |
| | 58 | ND | ND | ND | 1800 | 2000 | 80 |
| | 59 | ND | ND | ND | 6 | 680 | 1 |
| | 60 | ND | ND | ND | 60 | 510 | 12 |
| 2 | 82 | ND | ND | ND | 100 | 3430 | 3 |
| | 83 | ND | ND | ND | ND | 3430 | 0.01 |
| | 84 | ND | ND | ND | 10 | 2483 | 0.4 |
| | 85 | ND | ND | ND | 20 | 6400 | 0.3 |

*ND—Not detectable (below detection limit)

Figure 7:
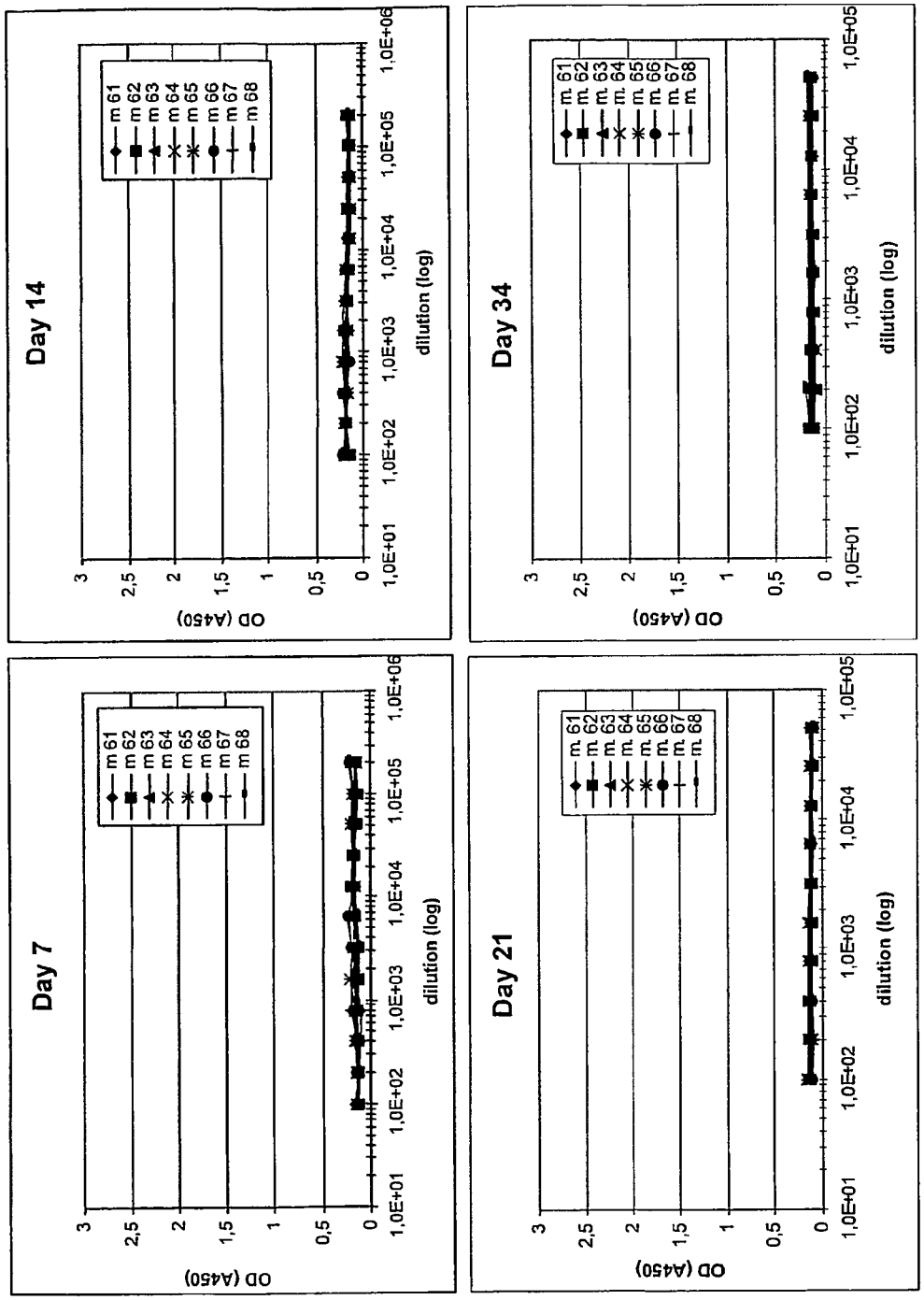
FIG. 7 shows ELISA titration curves for plasma from mice injected with $Z_{Taq4:1}$-ABD following scheme 1 as described in Example 2, when analyzed on ELISA plates coated with $Z_{Taq4:1}$-ABD.

Z$_{Taq4:1}$-ABD: Eight mice (#61-#68) were injected with Z$_{Taq4:1}$-ABD using scheme 1. Plasma samples obtained before injection (preplasma, data not shown) and after 7, 14, 21 and 34 days were analyzed for presence of Z$_{Taq4:1}$-ABD specific antibodies as described above. FIG. 7 shows the results. As is evident from FIG. 7, no specific IgG were induced against Z$_{Taq4:1}$-ABD.

There are high levels of mouse serum albumin (MSA) present in the analyzed samples. To circumvent the problem with MSA that might bind to the Z$_{Taq4:1}$-ABD coated ELISA surface, plasma samples were also titrated on plates coated with $His_6$-$Z_{Taq4:1}$ (data not shown). The analyses were once again negative, confirming the observation that the $Z_{Taq4:1}$-ABD molecule is non-immunogenic.

Figure 8:
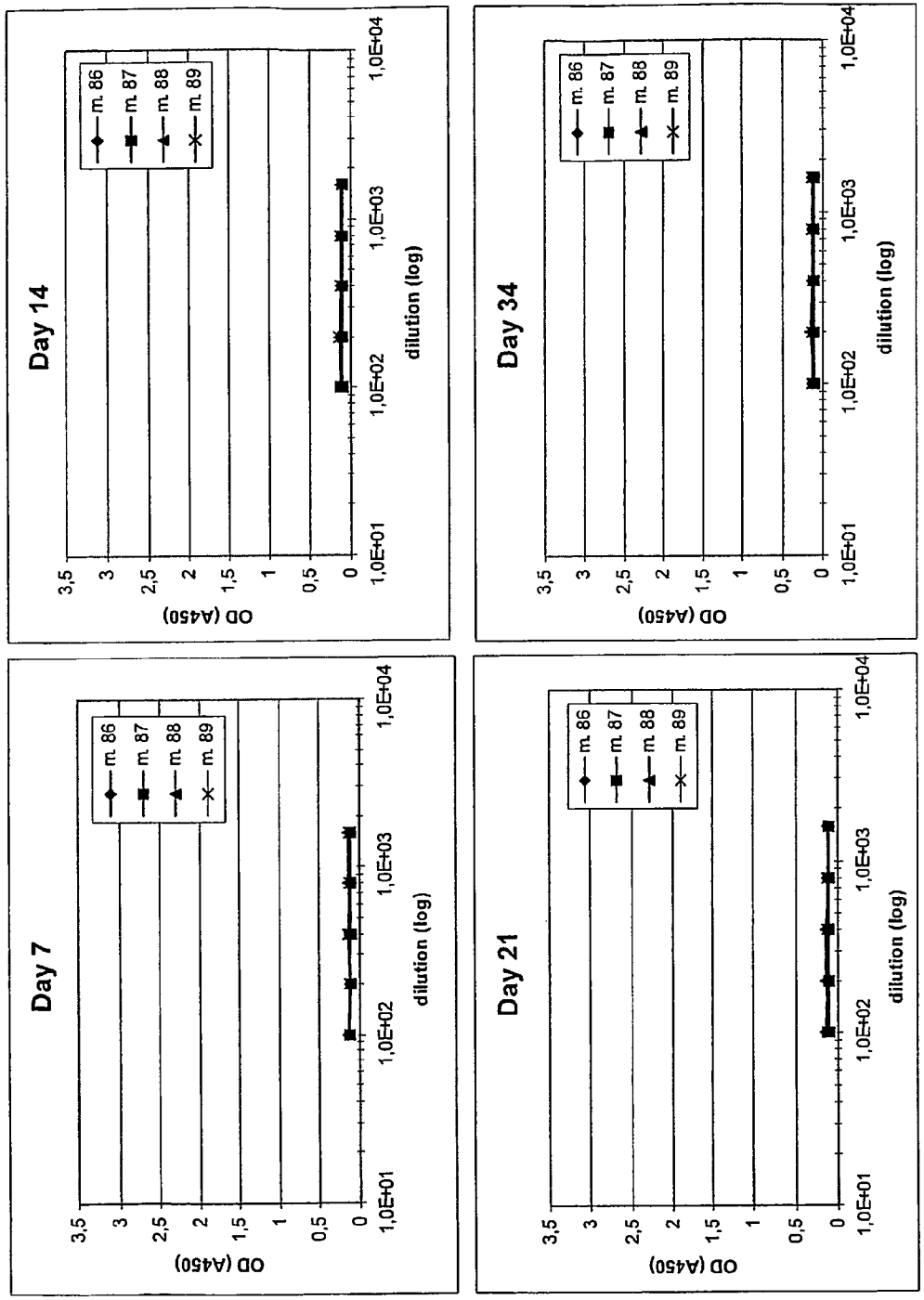
FIG. 8 shows ELISA titration curves for plasma from mice injected with $Z_{Taq4:1}$-ABD following scheme 2 as described in Example 2, when analyzed on ELISA plates coated with $Z_{Taq4:1}$-ABD.

Four mice (#86-#89) were injected with $Z_{Taq4:1}$-ABD according to scheme 2. Plasma samples obtained before injection (preplasma, data not shown) and after 7, 14, 21 and 34 days were analyzed for presence of $Z_{Taq4:1}$-ABD specific antibodies as described above. The results are shown in FIG. 8. Again, no IgG response could be measured.

Total IgG concentration was determined using the Bethyl-ELISA as described above, and the results are presented in Table 8.

TABLE 8

Total IgG in plasma following administration of $Z_{Taq4:1}$-ABD

| Scheme | Mouse # | Total IgG (μg/ml) at Day 34 |
|---|---|---|
| 1 | 61 | 500 |
|   | 62 | 1300 |
|   | 63 | 2600 |
|   | 64 | 1800 |
|   | 65 | 1700 |
|   | 66 | 1100 |
|   | 67 | 830 |
|   | 68 | 380 |
| 2 | 86 | 2500 |
|   | 87 | 870 |
|   | 88 | 2900 |
|   | 89 | 11100* |

*Unreliable, since value out of range

Figure 9:
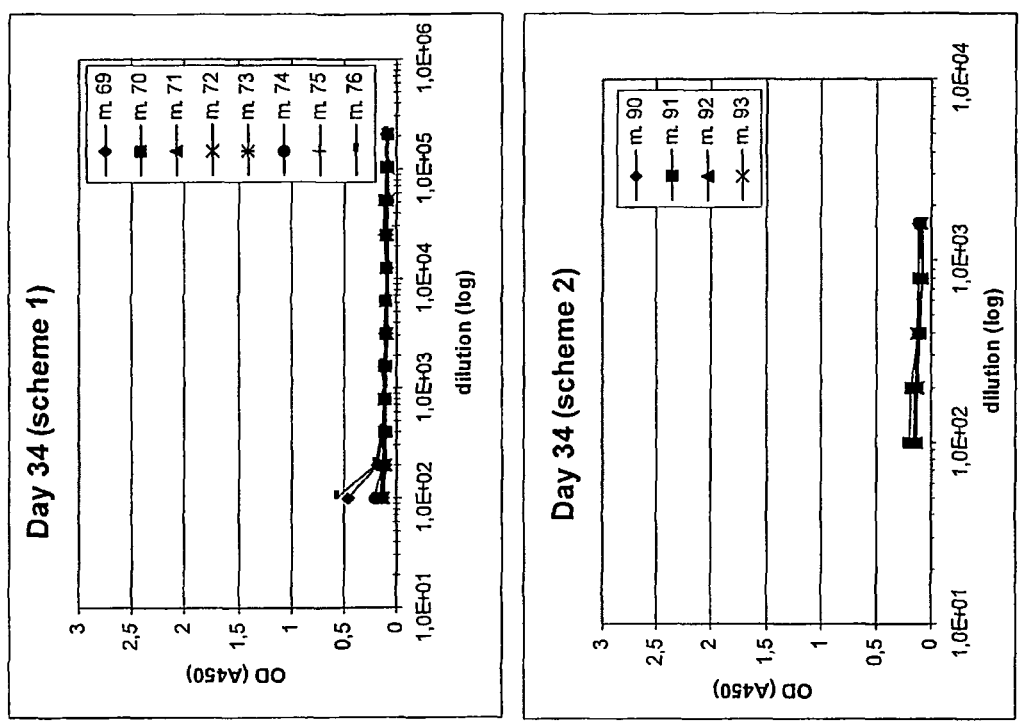
FIG. 9 shows ELISA titration curves for plasma from mice injected with ABD following scheme 1 (panel A) or scheme 2 (panel B) as described in Example 2, when analyzed on ELISA plates coated with ABD.

ABD: Eight mice (#69-#76) were injected with ABD according to scheme 1. Plasma obtained before injection (pre-plasma) and after 7, 14, 21 and 34 days was analyzed for presence of ABD-specific antibodies as described above. Very low titres of antibodies against the ABD molecule were detected, and only in Day 34 plasma (FIG. 9A). Pre-plasma and plasma from Day 7, 14 and 21 were negative (data not shown).

Four mice (#90-#93) were injected with ABD according to scheme 2. Plasma obtained before injection (preplasma) and after 7, 14, 21 and 34 days was analyzed for presence of ABD-specific antibodies as described above. No antibody response could be measure (FIG. 9B shows the results for samples of Day 34).

Total IgG concentration was determined using the Bethyl-ELISA as described above, and the results are presented in Table 9.

TABLE 9

Total IgG in plasma following administration of ABD

| Scheme | Mouse # | Total IgG (μg/ml) at Day 34 |
|---|---|---|
| 1 | 69 | 750 |
|   | 70 | 400 |
|   | 71 | 940 |
|   | 72 | 410 |
|   | 73 | 390 |
|   | 74 | 100 |
|   | 75 | 1100 |
|   | 76 | 304 |
| 2 | 90 | 3200 |
|   | 91 | 5100 |
|   | 92 | 6500 |
|   | 93 | 5800 |

Discussion

In accordance with the results of Example 1, $Z_{Taq4:1}$-ABD was unable to induce specific IgG responses in the mice. Likewise, the administration of ABD itself, devoid of fusion partner, did not elicit any measurable specific IgG response. The animals in these groups were administered the same amount of protein as in Example 1. Neither low frequency or high frequency injections generated detectable IgG responses. Since it is believed that the Z protein and its derivatives are T-dependent antigens, they would be expected to generate specific antibodies predominantly of the IgG isotype. Therefore, since these results show that no IgG antibodies are formed, they imply that no antibodies of other isotypes are formed either, in response to the $Z_{Taq4:1}$-ABD fusion protein.

EXAMPLE 3

Humoural Immune Response in Mice Following Administration of Multimers of a Z Variant Provided with an Albumin Binding Moiety Molecules Studied As in Examples 1 and 2, the inventive concept was again studied through a comparison of the antibody response in mice upon administration of different molecules. The molecules administered were the following:

$His_6$-$Z_{Taq4:5}$—as described in Example 2. Used for comparative purposes.

ABD-$Z_{her2:4}$—a fusion protein between the albumin binding domain (ABD) of streptococcal protein G strain G148 (see above) and the Z variant $Z_{her2:4}$. $Z_{her2:4}$ was selected from a library of combinatorial variants of Z and characterized. In the selection procedure, purified protein corresponding to the cancer antigen HER2 (also described in the literature as neu, HER2/neu or c-erbB-2) was used as the target molecule. $Z_{her2:4}$ was found to interact with HER2 with a $K_D$ value of approximately 50 nM. The amino acid sequence of $Z_{her2:4}$, in standard one-letter code, is:

VDNKFNKELR QAYWEIQALP NLNWTQSRAF IRSLYDDPSQ SANLLAEAKK LNDAQAPK (SEQ ID NO:4)

The fusion protein was prepared through expression of the corresponding DNA sequence together with the DNA sequence encoding the ABD moiety, in accordance with known molecular biology procedures. The ABD-$Z_{her2:4}$ fusion protein is used to illustrate the invention.

ABD-$(Z_{her2:4})_2$— a fusion protein between the albumin binding domain (ABD) and a dimer of the Z variant $Z_{her2:4}$, prepared in accordance with known molecular biology procedures with the added knowledge of $Z_{her2:4}$ sequence information. Used to illustrate the invention.

ABD-$(Z_{her2:4})_3$— a fusion protein between the albumin binding domain (ABD) and a trimer of the Z variant $Z_{her2:4}$, prepared in accordance with known molecular biology procedures with the added knowledge of $Z_{her2:4}$ sequence information. Used to illustrate the invention.

ABD-$(Z_{her2:4})_4$— a fusion protein between the albumin binding domain (ABD) and a tetramer of the Z variant $Z_{her2:4}$, prepared in accordance with known molecular biology procedures with the added knowledge of $Z_{her2:4}$ sequence information. Used to illustrate the invention.

Materials and Methods

Mice and administration schedule: Female NMRI mice (30 mice, plus 2 as a reserve) were used in this experiment. Body weight upon arrival was 20 g. At the start of the immunization experiments, the mice were from 8 to 12 weeks old. The mice were kept and fed in accordance with guidelines from the Swedish Ministry of Agriculture, Food and Fisheries. Food and water were given ad libitum. For the immunization experiment, the mice were split into five groups according to Table 10. 20 µg of the molecules indicated in Table 10 were administered subcutaneously to each mouse in 0.1 ml NaCl, 0.9%.

TABLE 10

Mouse groups and administered molecules

| Group | Mouse # | Molecule |
|---|---|---|
| 1 | 114-119 | $His_6$-$Z_{Taq4:5}$ |
| 2 | 120-125 | ABD-$Z_{her2:4}$ |
| 3 | 126-131 | ABD-$(Z_{her2:4})_2$ |
| 4 | 132-137 | ABD-$(Z_{her2:4})_3$ |
| 5 | 138-143 | ABD-$(Z_{her2:4})_4$ |

The solutions of test molecules were kept frozen at −20° C. and thawed before injection. The mice of group 1 received subcutaneous injections at Day 0, 3, 6, 9, 12 and 63 of the study (scheme 1). Blood samples of 150 µl were taken from the orbital plexus of the mice of group 1 at Day 0 (preplasma), 7, 14, 21, 34, 49 and 63 of the study. At Day 73 of the study, these mice were sacrificed and the maximal amount of blood obtained.

The mice of groups 2-5 received subcutaneous injections at Day 0, 3, 6, 9, 12 and 21 of the study (scheme 2). Blood samples of 150 µl were taken from the orbital plexus of the mice of groups 2-5 at Day 0 (preplasma), 7, 14 and 21 of the study. At Day 34 of the study, these mice were sacrificed and the maximal amount of blood obtained. Blood was collected in $K^+$EDTA tubes, and left to stand for one hour after sampling. Thereafter, samples were centrifuged at 6000 rpm for 6 min in order to separate plasma. Plasma was frozen at −20° C. for storage before analysis.

Analysis of plasma samples by specific ELISA: In general, a volume of 100 µl per well was used for all incubation steps except for blocking, where 200 µl were used. ELISA plates (Costar, no 9018) were incubated 1-3 days for coating, 1-2 hours for blocking and plasma, 1 hour for secondary antibody and 15 min for substrate solution. The incubations were performed on a shaker at room temperature, except coating, which was incubated at 4° C. Washing was done between all steps, unless otherwise stated, using the ELISA SkanWasher 300 (Skatron) with 4×350 µl washing buffer (PBS-T, see Example 1) per well. Plates were read at 450 nm in a Tecan ELISA reader using the Magellan v3.11 software. Blocking buffer was used for all dilutions except coating, where coating buffer (15 mM $Na_2HCO_3$, 35 mM $NaHCO_3$, pH 9.6) was used instead.

ELISA-plates were coated with $His_6$-$Z_{Taq4:5}$ or ABD-$(Z_{her2:4})_2$, diluted to a concentration of 5 µg/ml. After coating, plates were blocked with PBS+0.5% casein (PBS (2.68 mM KCl, 1.47 mM $KH_2PO_4$, 137 mM NaCl, 8.1 mM $Na_2HPO_4$, pH 7.4) with 0.5% casein (Sigma, cat no C-8654)). Blocking was removed and plasma was added, diluted from 1:100 and then in 3-fold dilution series. Plasma from mice injected with $His_6$-$Z_{Taq4:5}$ was analyzed on ELISA plates coated with $His_6$-$Z_{Taq4:5}$, whereas plasma from mice injected with the four different $Z_{her2:4}$ constructs was analyzed on ELISA plates coated with ABD-$(Z_{her2:4})_2$. Also included was a standard comprising a pool of mouse antibodies previously obtained. The pool included IgG directed against $Z_{Taq4:5}$ and $Z_{her2:4}$. HRP conjugated goat anti-mouse IgG (Southern Biotech, cat no 1031-05), diluted 1:2000, was used as the secondary reagent, and the reaction was developed using ImmunoPure® TMB substrate solution (Pierce, cat no 34021). This incubation was performed in the dark. The colour development was stopped after 15 minutes by the addition of stop solution (2 M $H_2SO_4$; VWR, cat no 14374-1).

Results

Plasma samples obtained before immunization (pre-plasma), and after 7, 14, 21 and 34 days were analyzed for presence of specific antibodies, as described in the "Materials and methods" section. There were no antibodies specific for the injected molecules in any preplasma (data not shown). The diagrams presented in FIGS. 10-14 show the titration curves of individual plasma samples plotted against OD values at 450 nm.

Figure 10:
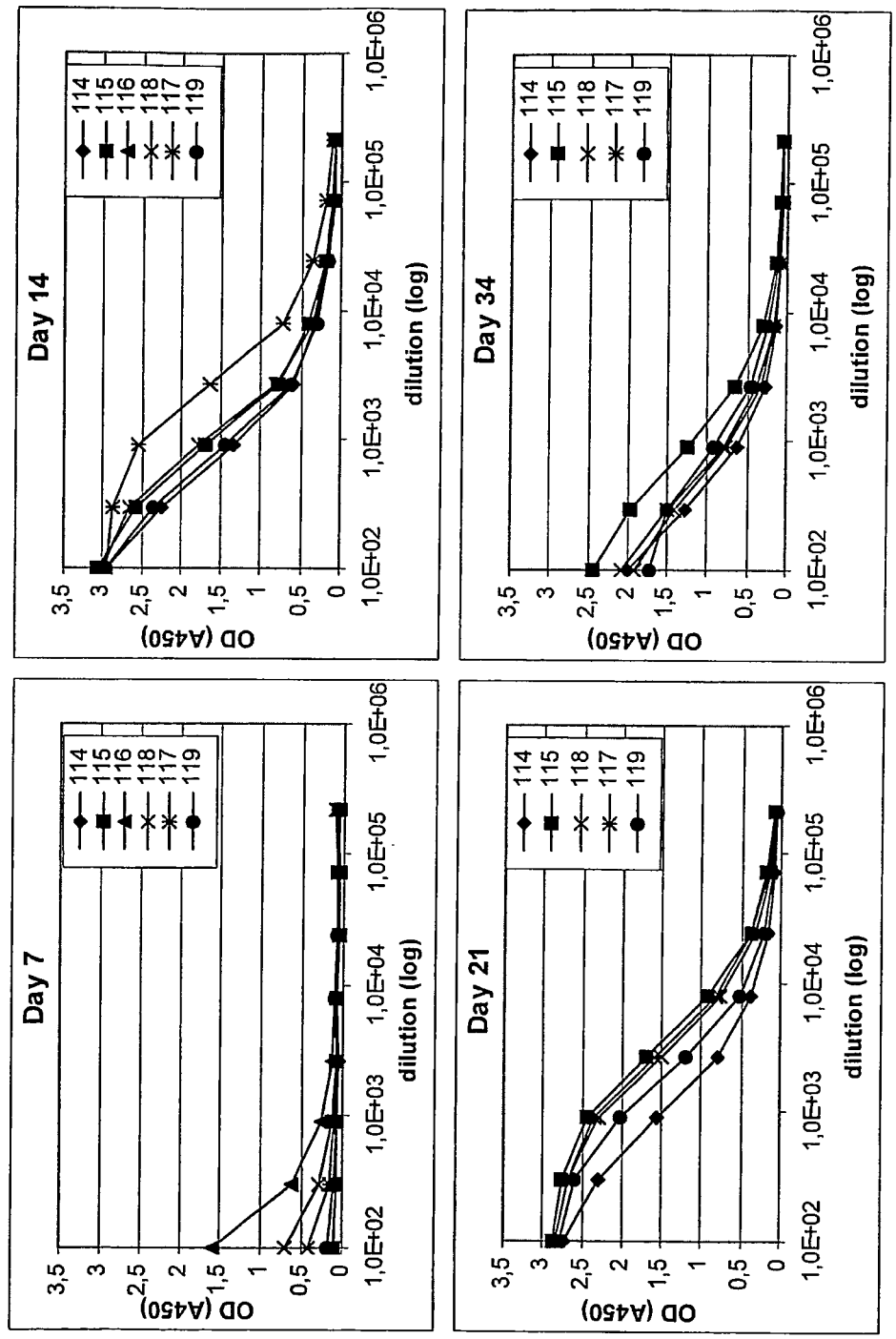
FIG. 10 shows ELISA titration curves for plasma from mice injected with $His_6$-$Z_{Taq4:5}$ as described in Example 3, when analyzed on ELISA plates coated with $His_6$-$Z_{Taq4:5}$.

$His_6$-$Z_{Taq4:5}$: The results are shown in FIG. 10. Mice injected with $His_6$-$Z_{Taq4:5}$ showed high antibody responses. The response was time dependent and seemed to peak at Day 21. Previous experiments with $His_6$-$Z_{Taq4:5}$ (Example 2) generally peaked at Day 34. The reason for the lower OD values at Day 34 of this study was likely due to the fact that these animals did not receive a booster injection at Day 21.

Figure 11:
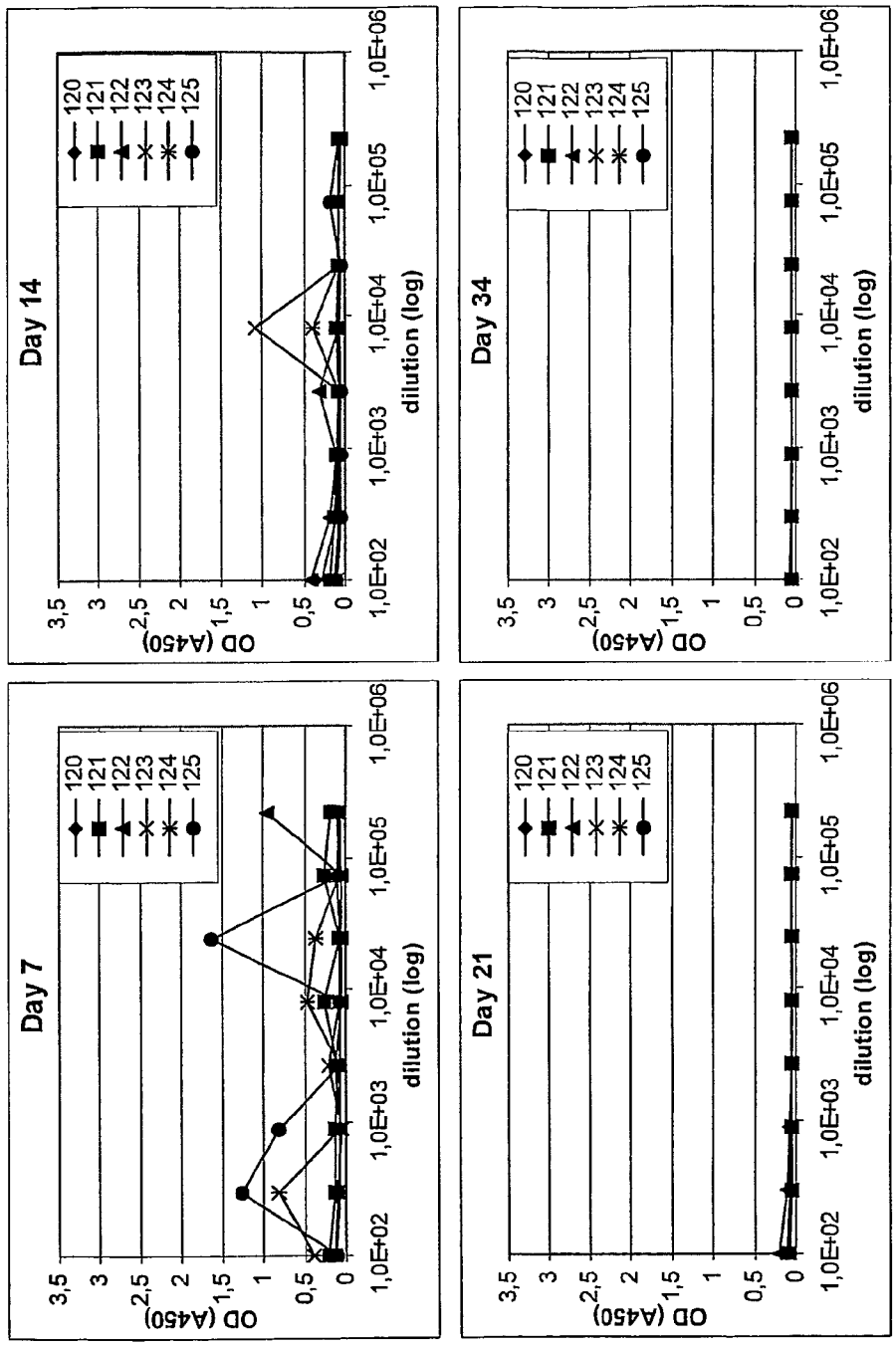
FIG. 11 shows ELISA titration curves for plasma from mice injected with ABD-$Z_{her2:4}$ as described in Example 3, when analyzed on ELISA plates coated with ABD-$(Z_{her2:4})_2$. The peaks seen in the diagrams of plasma from Day 7 and Day 14 are due to problems with the ELISA plate washer.

ABD-$Z_{her2:4}$: The results are shown in FIG. 11. Mice injected with ABD-$Z_{her2:4}$ showed no specific IgG response. The peaks seen in the diagrams of plasma from Day 7 and Day 14 are due to problems with the ELISA plate washer, and thus do not correctly represent the antibody content in the plasma.

Figure 12:
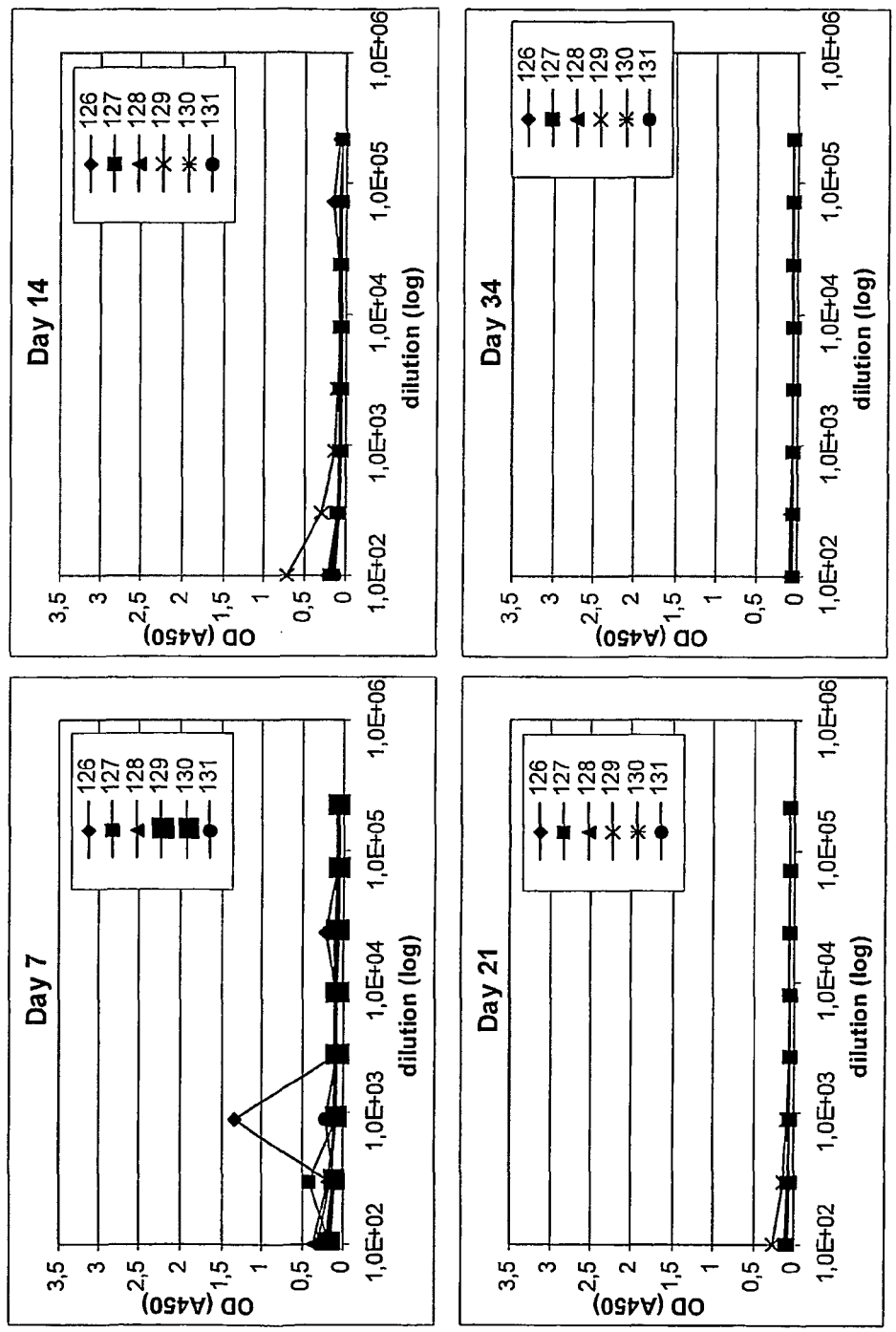
FIG. 12 shows ELISA titration curves for plasma from mice injected with ABD-$(Z_{her2:4})_2$ as described in Example 3, when analyzed on ELISA plates coated with ABD-$(Z_{her2:4})_2$. The peak seen in the diagram of plasma from Day 7 are due to problems with the ELISA plate washer.

ABD-$(Z_{her2:4})_2$: The results are shown in FIG. 12. Mice injected with ABD-$(Z_{her2:4})_2$ showed no specific IgG response. The peak seen in the diagram of plasma from Day 7 are due to problems with the ELISA plate washer, and thus do not correctly represent the antibody content in the plasma.

Figure 13:
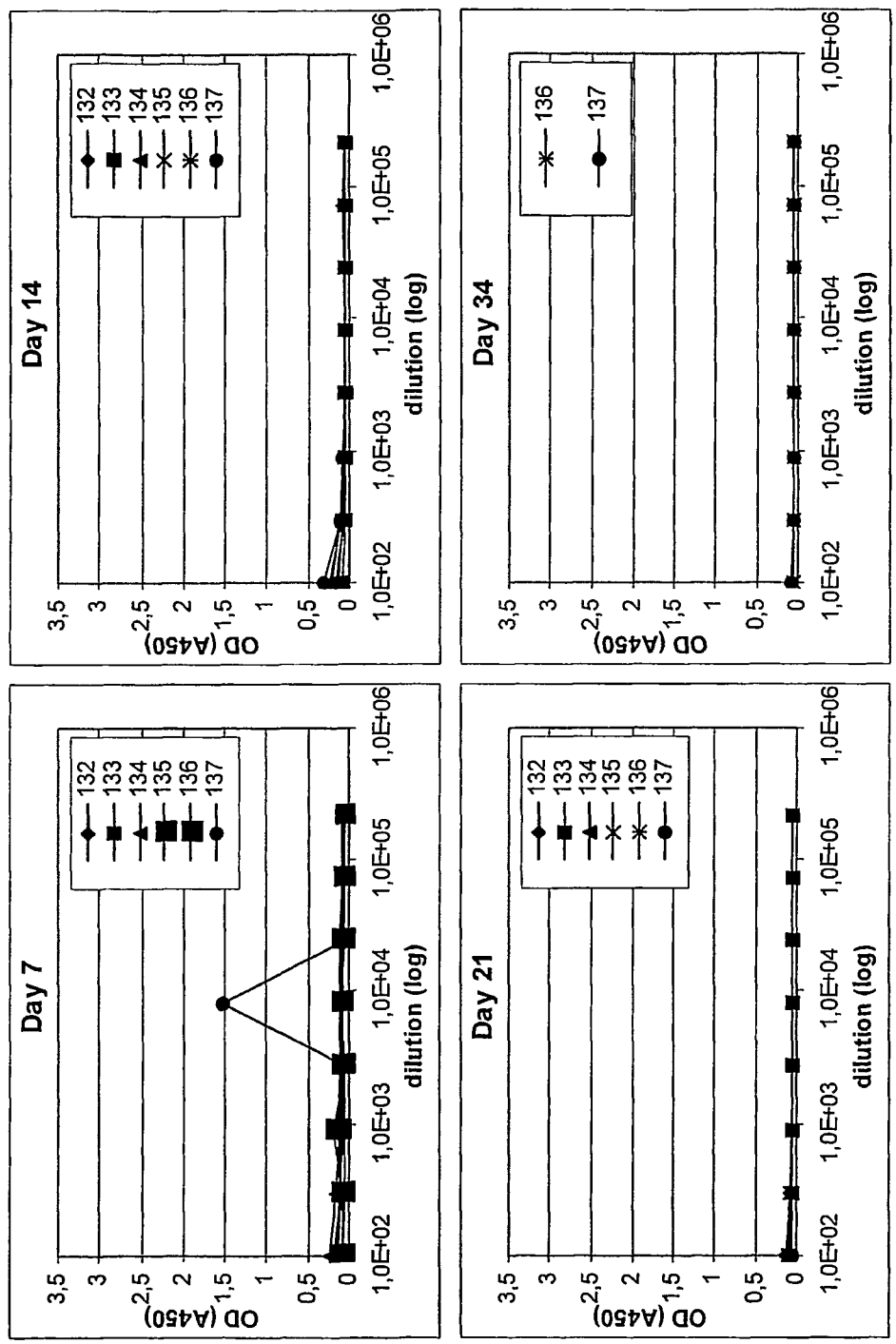
FIG. 13 shows ELISA titration curves for plasma from mice injected with ABD-$(Z_{her2:4})_3$ as described in Example 3, when analyzed on ELISA plates coated with ABD-$(Z_{her2:4})_2$. The peak seen in the diagram of plasma from Day 7 are due to problems with the ELISA plate washer.

ABD-$(Z_{her2:4})_3$: The results are shown in FIG. 13. Mice injected with ABD-$(Z_{her2:4})_3$ showed no specific IgG response. The peak seen in the diagram of plasma from Day 7 are due to problems with the ELISA plate washer, and thus do not correctly represent the antibody content in the plasma.

Figure 14:
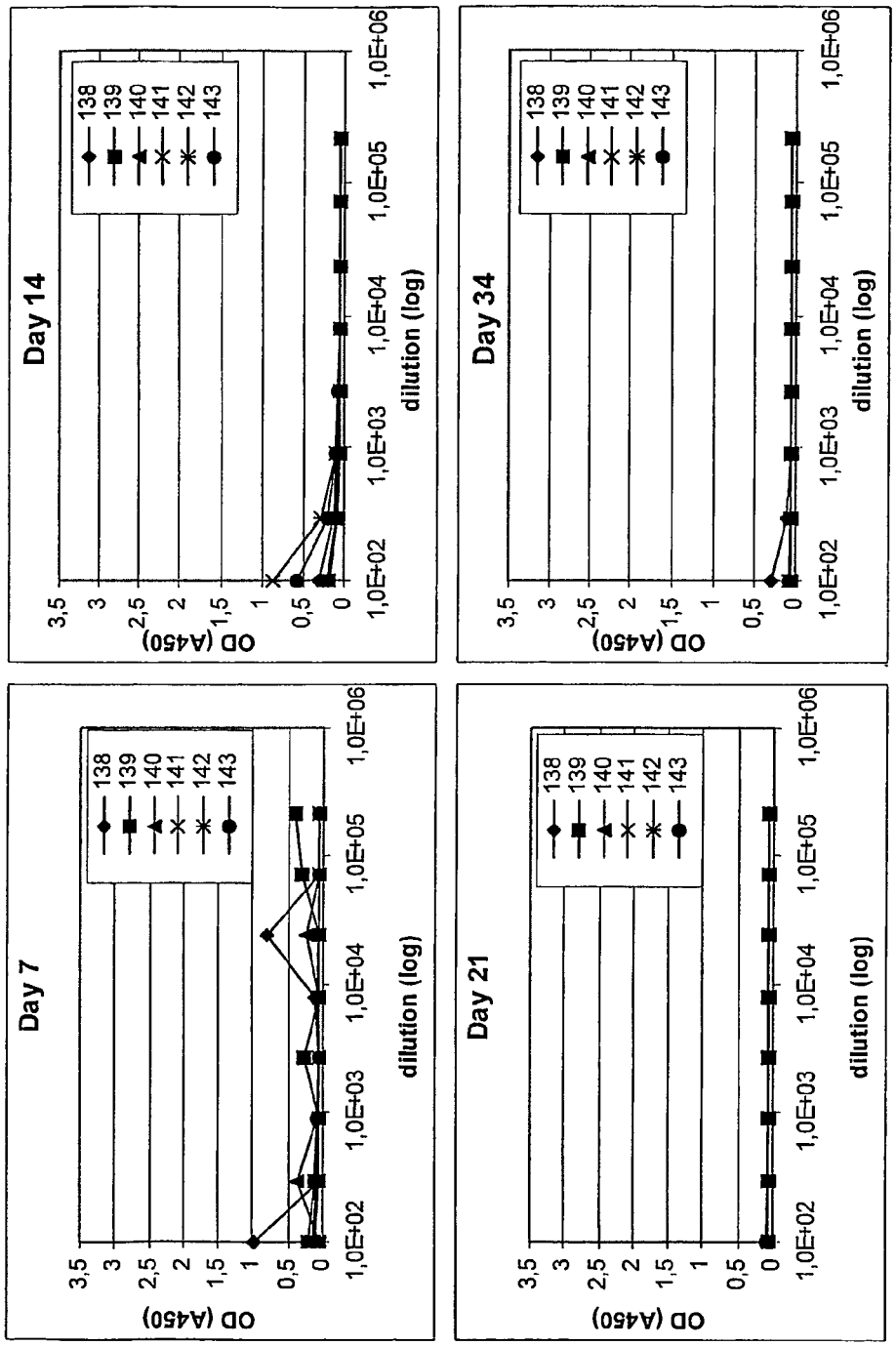
FIG. 14 shows ELISA titration curves for plasma from mice injected with ABD-$(Z_{her2:4})_4$ as described in Example 3, when analyzed on ELISA plates coated with ABD-$(Z_{her2:4})_2$. The peaks seen in the diagram of plasma from Day 7 are due to problems with the ELISA plate washer.

ABD-$(Z_{her2:4})_4$: The results are shown in FIG. 14. Mice injected with ABD-$(Z_{her2:4})_4$ showed no specific IgG response. The peaks seen in the diagram of plasma from Day 7 are due to problems with the ELISA plate washer, and thus do not correctly represent the antibody content in the plasma.

Also tested was the ability of the four different ABD-$(Z_{her2:4})_n$ constructs to elicit a specific IgM response. No such responses were detected (data not shown).

Discussion

The results of this experiment confirm the finding from Examples 1 and 2 that the provision of an albumin-binding moiety reduces or eliminates the immune response to a biologically active protein. Importantly, the effect was shown to be valid for proteins of increasing size. The tetramer of $Z_{her2:4}$ comprises more than 230 amino acid residues, but despite its size does not elicit a substantial antibody response upon administration in mice.

EXAMPLE 4

Reduction of Immune Response Tested with Dimers of Further Biologically Active Molecules Molecules Studied The aim of this study was also to assess if the antibodies, generated after immunization, are able to inhibit the binding between specific AFFIBODY® molecules and their target protein. The previous observation of a reduction in immune response when a biologically active protein is coupled to an albumin binding domain was confirmed using two other AFFIBODY® molecules: $(Z_{A\beta3})_2$ and ABD-$(Z_{A\beta3})_2$.

$(Z_{A\beta3})_2$—a dimer of a variant of protein Z, in turn derived from the B domain of staphylococcal protein A. The $Z_{A\beta3}$ variant was produced using recombinant DNA technology, through expression of the DNA sequence encoding it, according to known molecular biology procedures. Used for comparative purposes.

ABD-$(Z_{A\beta3})_2$— a fusion protein between the albumin binding domain (ABD) and a dimer of the Z variant $Z_{A\beta3}$ prepared in accordance with known molecular biology procedures. Used to illustrate the invention.

$His_6$-$Z_{Taq4:1}$—the his-tagged variant of protein Z described in Example 1. Used for comparative purposes.

$His_6$-$Z_{Taq4:5}$—the his-tagged variant of protein Z described in Example 2. Used for comparative purposes.

Materials and Methods

Mice were injected with two different dimeric AFFIBODY® molecules, $(Z_{A\beta3})_2$ and ABD$(Z_{A\beta3})_2$. Plasma from mice was obtained as before, four times during the treatment scheme and after booster and was analyzed for presence of AFFIBODY®-specific IgG. The results showed that the mice injected with $(Z_{A\beta3})_2$, generated a strong IgG response. The antibody production started around day 14 and peaked at day 34. The average concentration of specific IgG at death bleeding was 278 µg/ml $(Z_{A\beta3})_2$. No specific antibodies were detected in plasmas from mice treated with ABD$(Z_{A\beta3})_2$.

Total IgG-concentration was determined in plasma at day 0 and day 34 from both groups of mice. The concentration of total IgG increased approximately 2 times in both groups over the 34 day period.

An inhibition-ELISA was set up to test if anti-$(Z_{A\beta3})_2$-antibodies were able to neutralize the interaction between the AFFIBODY® molecule and the target protein. The results showed that $(Z_{A\beta3})_2$-specific IgG did not neutralize the interaction between $(Z_{A\beta3})_2$ and β-Amyloid 40.

Mice and Administration Schedule

The mice were treated with $(Z_{A\beta3})_2$ and $(Z_{A\beta3})_2$-ABD according to the scheme (Table 11). The injection and bleeding scheme is shown in Table 12. Mouse 5 in group 1 became sick and was removed from the study after bleeding day 22.

TABLE 11

| Group | Treatment | Mouse strain | Admin. | µg/animal/ injection | ml/animal/ injection | Animal number |
|---|---|---|---|---|---|---|
| 1 | $(Z_{A\beta3})_2$ | NMRI | s.c. | 20 | 0.1 | 1-6 |
| 2 | ABD-$(Z_{A\beta3})_2$ | NMRI | s.c. | 20 | 0.1 | 7-12 |

TABLE 12

| Day | Treatment |
|---|---|
| 0 | Preserum (= Sample 1) and Injection 1 |
| 3 | Injection 2 |
| 6 | Injection 3 |
| 7 | Sample 2 (day 7) |
| 9 | Injection 4 |
| 12 | Injection 5 |
| 14 | Sample 3 (day 14) |
| 21 | Sample 4 (day 21), and Injection 6 |
| 34 | Sample 5 (= death bleeding, day 34) |

Purification of IgG from Mouse Plasma

Total IgG was purified from pooled plasma day 34 (mouse no 5 day 21) from the mice immunized with $(Z_{A\beta3})_2$. The plasma pool, 2400 µl, was diluted 5 times with PBS-T to a total amount of 12 ml before loading on a $Z_{wt}$-coupled High-Trap column (L0091-98) previously equilibrated with PBS-T. The column was washed until absorbance values reached zero and bound IgG was eluted using an acidic elution buffer (0.2M Glycine, 1 mM EGTA, pH 2.8). For neutralization, 1M Tris base was added to a final concentration of 50 mM. The buffering capacity was restored by adding 1/10 of the elution volume of 10×PBS (2.68 mM KCl, 1.47 mM $KH_2PO_4$, 137 mM, NaCl, 8.1 mM $Na_2HPO_4$, pH 7.4, PBS-Tween (PBS T), 1×PBS with 0.05% Tween).

ELISA-plates (96 well, flat bottom, high binding Costar No. 9018) were coated with the appropriate AFFIBODY® molecule diluted in coating buffer to a final concentration of 2 µg/ml. 100 µl of the coating solution was added per well and plates were incubated for 1-3 nights at 4° C. The plates were then washed manually four times with deionized water and blocked with blocking buffer (0.5% Casein (Sigma) in 1×PBS; 200 µl/well) for 1 to 2 hours. Blocking buffer was removed, and 100 µl of serum was added to each well in dilution series. After 1 hour incubation, the plates were washed with the automated ELISA-washer or manually four times with PBS-T, and 100 µl of the second step antibody, HRP-conjugated goat anti-mouse IgG diluted 1:2000 in blocking buffer, was added to each well. The plates were subsequently incubated for 1 hour. Plates were washed four times with PBS-T and 100 µl of substrate solution (IMMUNOPURE® TMB) was added to each well followed by incubation in the dark. The colour development was stopped after 15 minutes by the addition of 100 µl of stop solution 2M $H_2SO_4$. Plates were read at 450 nm in an ELISA-reader with the use of the Magellan software.

Mouse Anti $Z_{A\beta3}$-Specific IgG ELISA

Plates were coated with $(Z_{A\beta3})_2$ 2 µg/ml in coating buffer and incubated overnight at 4° C. After washing, plates were blocked as described above. Plasma from mice immunized with $(Z_{A\beta3})_2$ or with ADB$(Z_{A\beta3})_2$ was added in 3-fold dilution series starting from 1/100. After incubation, plates were treated as described above.

To measure the concentration of AFFIBODY® specific IgG, a standard plasma pool was used, the Scheele 8 pool. The concentration of anti-Z IgG in this serum pool had been determined on $His_6$-$Z_{Taq4:1}$-coated plates to 97 µg/ml. The concentration of anti-$His_6$-$Z_{Taq4:5}$ and anti-$(Z_{A\beta3})_2$ IgG in Scheele 8 pool was determined to be 291 and 97 µg/ml respectively (L0242-14/16). As a positive control we used plasma from mouse #117 (Scheele 7; day 73, in a dilution of 1:10.000, which should give an OD value close to the inflection point of the standard curve. Negative control was blocking buffer. The limit of detection was 3 ng/ml.

Total IgG ELISA

Plasmas from day 0 and day 34 (mouse no 5 day 21) from both groups of mice were analyzed regarding the total amount of IgG. In this assay, ELISA-plates were coated with $(Fab)_2$ fragments of goat anti-mouse IgG-Fc antibodies (Southern Biotech no. 1031-05 0.5 µg/ml). Plasma or standard (mouse IgG) in 3-fold dilution series starting from 1:10000 and 100 ng/ml respectively was added to coated wells. The reaction was developed with HRP-conjugated $(Fab)_2$ fragments of goat anti-mouse IgG-fab antibodies (0.2 µg/ml). Substrate solution (ImmunoPure® TMB Pierce no. 34021) was added and the colour development was stopped after 10 minutes incubation in dark by the addition of stop solution.

Inhibition ELISA Analysis

Plates were coated with $(Z_{A\beta3})_2$, 2 µg/ml in coating buffer and incubated overnight in 4° C. After washing plates were blocked as described above. Purified anti-$(Z_{A\beta3})_2$ IgG was added in 3-fold dilution series starting from 1 µg/ml. After 1 h incubation the protein β-Amyloid 40, biotinylated, was added to the wells without washing in between. The final concentration of β-Amyloid 40 BioSite A2275-74D was 10 µg/ml. The plates were washed after one additional hour of incubation and depending on what reaction to analyze, either goat-anti-mouse IgG HRP (Dalco P0397 diluted 1/2000) or streptavidin-HRP (diluted 1/5000) was added. After the final incubation, plates were washed and developed as described above.

Data Analysis

Magellan (Tecan) was used as ELISA reader software. The results were exported to Excel for data analysis and presentation. For concentration determinations, the XLfit program, formula "Dose response-one site", equation 205, was used. Processed data from each day and type of measurement i.e. IgG, concentration etc, were represented by an Excel file.

Results

AFFIBODY®-specific IgG ELISA Group I

Figure 15:
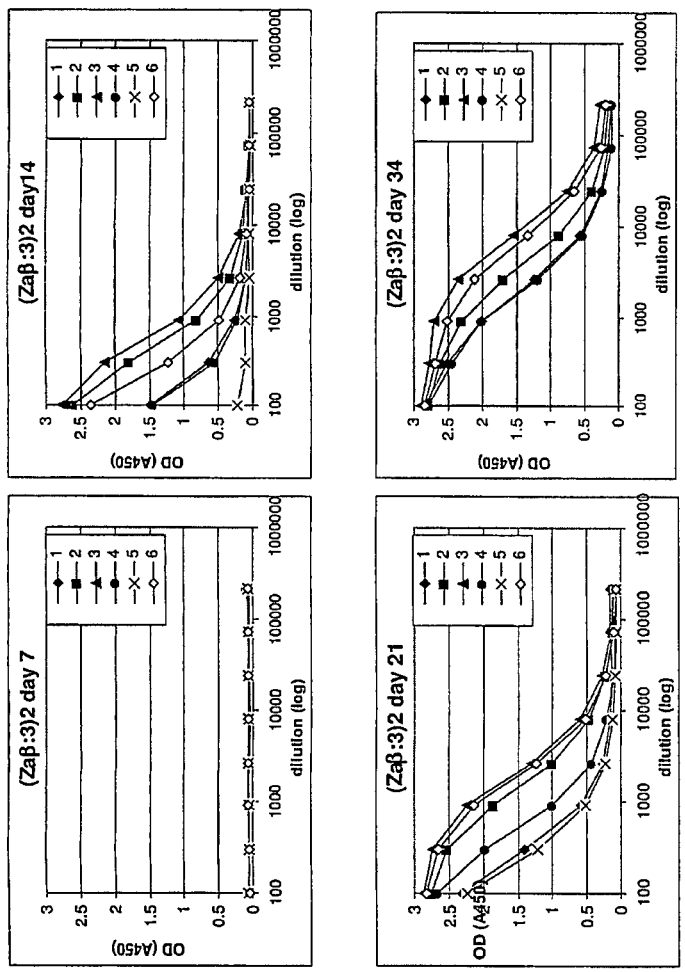
FIG. 15 shows ELISA titration curves for plasma from mice injected with $(Z_{a\beta:3})_2$ as described in Example 4 when analyzed on ELISA plates coated with $(Z_{a\beta:3})_2$.

Plasmas from six mice injected with $(Z_{A\beta3})_2$ was titrated on $(Z_{A\beta3})_2$-coated plates. All mice responded by day 14, although mouse 5 showed a very low response. The maximal anti-AFFIBODY®-IgG level was observed at day 34 (FIG. 15). The average concentration of specific IgG at day 34 was 278 µg/ml (Table 13). Mouse no 5 did not respond well and day 21 is the death bleeding sample. No specific IgG response could be detected in the serum samples from day 0 i.e. before administration (data not shown).

TABLE 14

Concentration of specific IgG (ND = Not Detectable)

| Group 1 | Concentration of specific IgG in µg/ml | | | |
|---|---|---|---|---|
| | day 7 | day 14 | day 21 | day 34 |
| mouse 1 | ND | 3.7 | 9.8 | 121.3 |
| mouse 2 | ND | 13.5 | 51.3 | 216.3 |
| mouse 3 | ND | 19.8 | 78.2 | 530.8 |
| mouse 4 | ND | 3.4 | 17.2 | 113.7 |
| mouse 5 | ND | ND | 7.6 | —* |
| mouse 6 | ND | 8.0 | 71.1 | 407.9 |
| Average | ND | 9 | 39 | 278 |
| St dev | | 6 | 29 | 165 |

ND: Not detected, values were below the detection limit 3 ng/ml.
*Mouse 5 became sick and was removed from the study day 22.

AFFIBODY®-specific IgG ELISA Group 2

Figure 16:
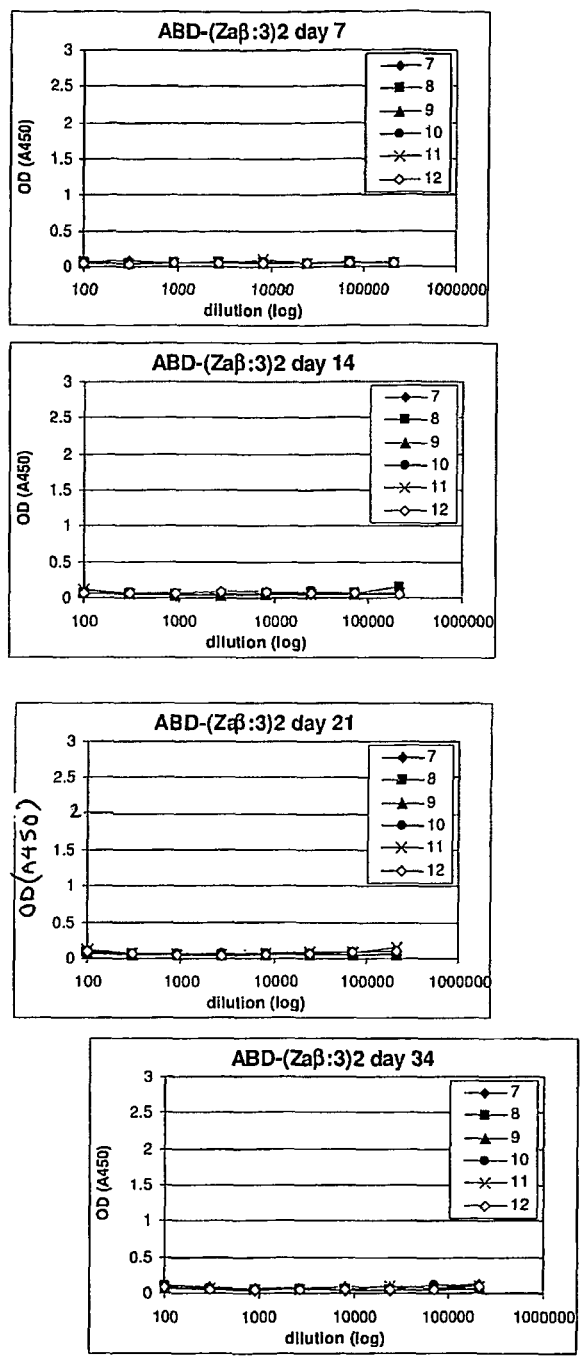
FIG. 16 shows ELISA titration curves for plasma from mice injected with ABD-$(Z_{a\beta:3})_2$ as described in Example 4 when analyzed on ELISA plates coated with ABD-$(Z_{a\beta:3})_2$.

Plasma from six mice injected with ADB-$(Z_{A\beta3})_2$ was titrated on $(Z_{A\beta3})_2$-coated plates. No specific IgG concentration could be detected in any of the bleeding samples. (FIG. 16).

Total IgG ELISA

Plasma from both groups of mice day 0 and day 34 (mouse no 5 day 21), was titrated on $(Z_{A\beta:3})_2$ coated plates. As shown in Table 15 the amount of total IgG increased over the 34 day period in both groups. However, considering that day 0 levels are surprisingly low, the increase may reflect the normal expansion in a mouse over that particular period in life. Plasma from vehicle mice would have been the appropriate control.

TABLE 15

Total IgG concentrations group 1

| | Group 1 ($Z_{A\beta:3}$)$_2$ | | Group 2 ABD-($Z_{A\beta:3}$)$_2$ | |
|---|---|---|---|---|
| Mouse no | Day 0/preplasma | Day 34/death bleeding | Day 0/preplasma | Day 34/death bleeding |
| 1 | 828.9 | 1724.4 | 812.9 | 1850.6 |
| 2 | 984.6 | 1948.5 | 931 | 2108.9 |
| 3 | 1142.1 | 2673 | 437.4 | 1091.7 |
| 4 | 2074.5 | 3418.2 | 900.3 | 1180.1 |
| 5 | 1789.2 | 3936.6 | 778.6 | 1839.3 |
| 6 | 829.8 | 1263.6 | 1322.9 | 2573.1 |

Inhibition ELISA: Target Protein

Figure 17:
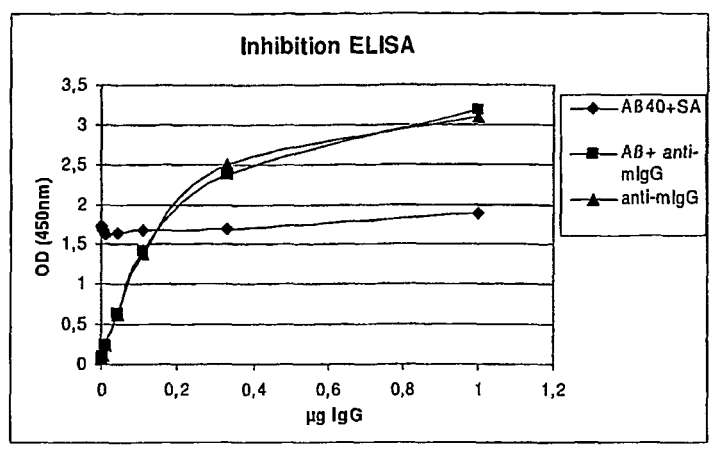
FIG. 17 shows the results of Inhibition ELISA experiments described in Example 4.

The likelihood that AFFIBODY® specific IgG antibodies neutralize/inhibit the interaction between the target protein and the AFFIBODY® molecule was explored by an inhibition ELISA. The ELISA-plate was coated with $(Z_{A\beta3})_2$ as described above. Total IgG, purified from a pool of plasma from group 1 day 34, was added. The IgG antibodies were added in 3-fold dilutions from 1 µg/ml. The antibodies were allowed to bind for one hour to the coated AFFIBODY® molecule before the target protein β-Amyloid 40 was added to a final concentration of 10 µg/ml. The reaction was developed with streptavidin-HRP to visualize the interaction between $(Z_{A\beta3})_2$ and the target protein (blue line). The interaction between the IgG-antibodies and the coated AFFIBODY® molecule was visualized with anti-mouse IgG HRP (FIG. 17). Specifically, FIG. 17 shows the results of inhibition ELISA. Binding of purified $(Z_{A\beta3})_2$-specific mouse antibodies to coated $(Z_{A\beta3})_2$ in the presence or absence of β-Amyloid 40. Purified IgG and target protein developed, with streptavidin HRP (♦). Purified IgG and target protein, developed with anti-mouse IgG HRP (■). Purified IgG developed with anti-mouse IgG HRP (▲). The experiment was repeated twice with the same result.

As control the titrated IgG-antibody was allowed to react with the coated AFFIBODY® molecule without adding any target protein. FIG. 17 also shows almost identical OD-values for the IgG-detection with anti-mouse IgG HRP with or without the target protein. These results indicate that $(Z_{A\beta3})_2$-specific IgG antibodies do not inhibit the interaction between $(Z_{A\beta3})_2$ and µ-Amyloid 40.

EXAMPLE 5

Reduction of Immune Response Tested in Additional Mouse Strain

As shown in Example 4 we have previously observed that $His_6$-$Z_{Taq4:1}$ but not $Z_{Taq4:1}$-ABD induces an antibody response in out bred NMRI mice. In this study, an additional out bred mouse strain (CD1) was tested and the results showed that CD1-mice responded as NMRI mice by producing specific IgG when administered with $His_6$-$Z_{Taq4:1}$ but not with $Z_{Taq4:1}$-ABD. Thus, the immune unresponsiveness observed upon injection of ABD-fused AFFIBODY®molecule ($Z_{Taq4:1}$) seems to be a general phenomenon in mice.

The nature of ABD-induced unresponsiveness was further analyzed in NMRI mice. Four groups of mice received ten (10) AFFIBODY® injections with a change of injected molecule after the fifth injection (according to treatment scheme 2). The results showed that mice, primed with $Z_{Taq4:1}$-ABD, produced AFFIBODY®-specific-IgG after antigen-switch to $His_6$-$Z_{Taq4:1}$ (group 4). The antibody production started approximately 14 days after the switch to $His_6$-$Z_{Taq4:1}$, which is the number of days usually necessary for naive mice to produce antibodies. Mice that were primed with $Z_{Taq4:1}$-ABD before receiving a mixture of $Z_{Taq}4:1$-ABD and $His_6$-$Z_{Taq4:1}$ (group 5) also started to produce specific IgG against the AFFIBODY® molecule. The observed specific response in group 5 was smaller than seen in group 4 which is most likely due to fact that group 5 received half of the injected dose of $His_6$-$Z_{Taq4:1}$ as compared to group 4. Mice in group 6 were primed with $His_6$-$Z_{Taq4:1}$ before receiving $Z_{Taq4:1}$-ABD and this treatment resulted in a continued AFFIBODY®-specific IgG production after the antigen switch although the titre decreased by time.

Figure 27:
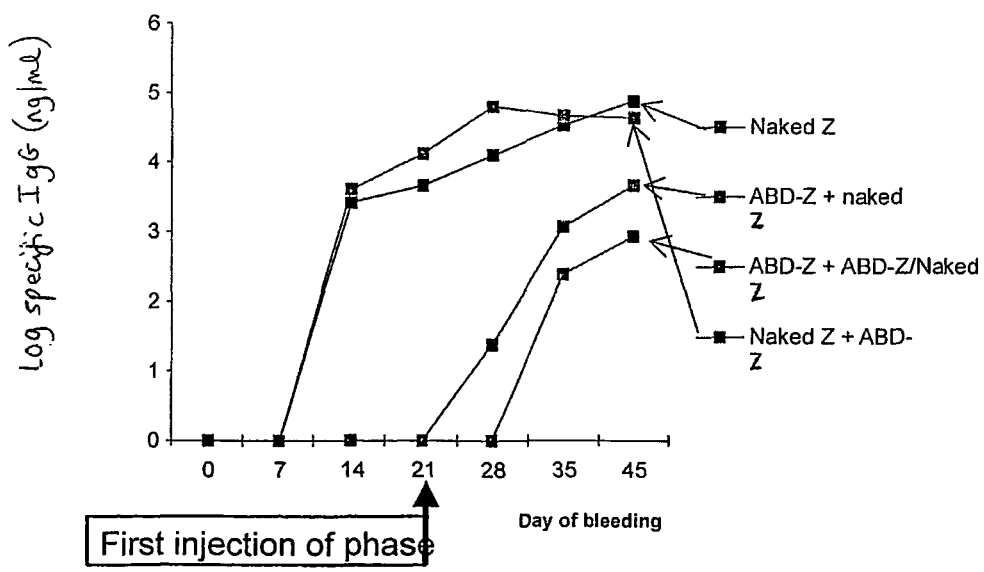
FIG. 27 A is a summary of the set up of Example 5.

This Scheele 9 study was performed mainly for two reasons: 1) does a second out bred mouse strain (CD1) respond to the administration of ABD-fused and unfused AFFIBODY® molecules in the same way as NMRI mice (BT1-PAR07, BT11-PAR03), and 2) when $Z_{Taq4:1}$-ABD is injected and followed by $His_6$-$Z_{Taq4:1}$, will the mice generate an AFFIBODY®-specific IgG response or not? The answer to the latter question helped us clarify whether the observed unresponsiveness towards ABD-fused AFFIBODY® molecules is an active or passive suppression process. The molecules used in each group of animals are listed in Table 16 and the two treatment schemes are presented in Tables 17 and 18. The setup of this study is illustrated in FIG. 27A.

TABLE 16

Animal number scheme for the Scheele 9 study; Affibody ® 1: $His_6$-$Z_{Taq4:1}$; AFFIBODY ® 3: $Z_{Taq4:1}$-ABD

| Group | Treatment | Mouse strain | Admin. | µg/animal/ injection | mL/animal/ injection | Animal number |
|---|---|---|---|---|---|---|
| 1 | Affibody 1 | CD1 | s.c. | 20 | 0.1 | 144-148 |
| 2 | Affibody 3 | CD1 | s.c. | 20 | 0.1 | 149-153 |
| 3 | Affibody 1 | NMRI | s.c. | 20 | 0.1 | 154-158 |
| 4 | Affibody 3 + 1 | NMRI | s.c. | 20 | 0.1 | 159-163 |
| 5 | Affibody 3 + 1/3 | NMRI | s.c. | 20 | 0.1 | 164-168 |
| 6 | Affibody 1 + 3 | NMRI | s.c. | 20 | 0.1 | 169-173 |

TABLE 17

Treatment scheme 1 for group 1 and 2

| Day | Treatment |
|---|---|
| 0 | Preplasma (= Sample 1) |
| 0 | Injection 1 |
| 3 | Injection 2 |
| 6 | Injection 3 |
| 7 | Sample 2 |
| 9 | Injection 4 |
| 12 | Injection 5 |
| 14 | Sample 3 |
| 21 | Sample 4 |
| 21 | Injection 6 |
| 34 | Death-bleeding (= Sample 5) |

TABLE 18

Treatment scheme 2 for group 3, 4, 5, and 6

| Day | Treatment |
|---|---|
| 0 | Preplasma (= sample 1) |
| 0 | Injection 1 |
| 3 | Injection 2 |
| 6 | Injection 3 |
| 7 | Sample 2 |
| 9 | Injection 4 |
| 12 | Injection 5 |
| 14 | Sample 3 |

TABLE 18-continued

Treatment scheme 2 for group 3, 4, 5, and 6

| Day | Treatment |
|---|---|
| 21 | Sample 4 |
| From now on | In group 4, 5, and 6: change of antigen |
| 21 | Injection 6 |
| 24 | Injection 7 |
| 27 | Injection 8 |
| 28 | Sample 5 |
| 30 | Injection 9 |
| 33 | Injection 10 |
| 35 | Sample 6 |
| 45 | Death-bleeding (= sample 7) |

Materials and Methods

AFFIBODY® ELISA 96 well, flat bottom, high binding Costar ELISA plates were coated with $His_6$-$Z_{Taq4:1}$ diluted in coating buffer (10× coating buffer, 150 mM $Na_2CO_3$, 350 mM $NaHCO_3$, pH 9.6 pH9.6) to a final concentration of 5 µg/ml. 100 µl of the coating solution was added per well, and plates were incubated for 1-4 nights at 4° C. The plates were then washed manually four times with deionized water and blocked with blocking buffer (200 µl/well) for 1 to 2 hours. Blocking buffer was removed and 100 µl of plasma was added to each well, diluted from 1:100 in blocking buffer, and then in 3-fold dilution series. To measure the concentration of AFFIBODY®-specific IgG, a standard plasma pool was used, the Scheele 6B pool. The concentration of anti $His_6$-$Z_{Taq4:1}$ IgG in this plasma pool had been determined to 120 µg/ml. As a positive control we used plasma from mouse #118 of the Scheele 7 study, day 73, in a dilution of 1:9200, which should give an OD value near the inflection point of the standard curve. Negative control was blocking buffer.

After 2 hours of incubation, the plates were washed four times with PBS-T (Phosphate buffered saline (10×PBS) 2.68 mM KCl, 1.47 mM $KH_2PO_4$, 137 mM NaCl, 8.1 mM $Na_2HPO_4$, pH 7.4; PBS-Tween (PBS-T), 1×PBS with 0.05% Tween) and 100 µl of a second step antibody, HRP-conjugated goat anti-mouse IgG diluted 1:2000 in blocking buffer (PBS-Tween (PBS-T), 1×PBS with 0.05% Tween) was added in each well. The plates were thereafter incubated for 1 hour. Plates were washed four times with PBS-T and 100 µl of the substrate solution (ImmunoPure® TMB) was added to each well. Plates were incubated in the dark and the color development was stopped after 15 minutes by the addition of 100 µl of stop solution (2M $H_2SO_4$). Plates were read at 450 nm in an ELISA-reader with the use of the Magellan software.

Total IgG ELISA

For determination of total IgG in plasma, a quantitative ELISA was performed. The procedure was the same as for the AFFIBODY® ELISA, with the following differences:

ELISA-plates were coated with AffiniPure (Fab')$_2$ fragment goat anti-mouse IgG Jackson 115-006-008 (Fcγ-fragment specific), in a concentration of 0.5 μg/1 ml. Dilutions of the first and second step were done in PBS-T without casein, and the dilution series of plasma began at 1:10.000. Standard IgG was ChromPure mouse IgG Jackson 015-000-003, whole molecule, in a dilution series beginning with 100 ng/ml. Peroxidase-conjugated AffiniPure F(ab')$_2$ fragment goat anti-mouse IgG (F(ab')$_2$-fragment specific) Jackson 115-036-006 diluted 1:2000 was used as second step antibody.

Data Analysis

Magellan (Tecan) was used as ELISA reader software. The results were exported to Excel for data analysis and presentation. For concentration determinations, the XLfit program, formula "Dose response-one site", equation 205, was used.

Results

Treatment Scheme 1

Group 1 and 2 consisted of CD1 mice. The animals were injected with either His$_6$-Z$_{Taq4:1}$ (group 1) or Z$_{Taq4:1}$-ABD (group 2), according to treatment scheme 1 (Table 17). Blood samples obtained before, during, and after immunization were analyzed on His$_6$-Z$_{Taq4:1}$ coated plates for detection of IgG-antibodies specifically recognizing His$_6$-Z$_{Taq4:1}$.

Group 1

Figure 18:
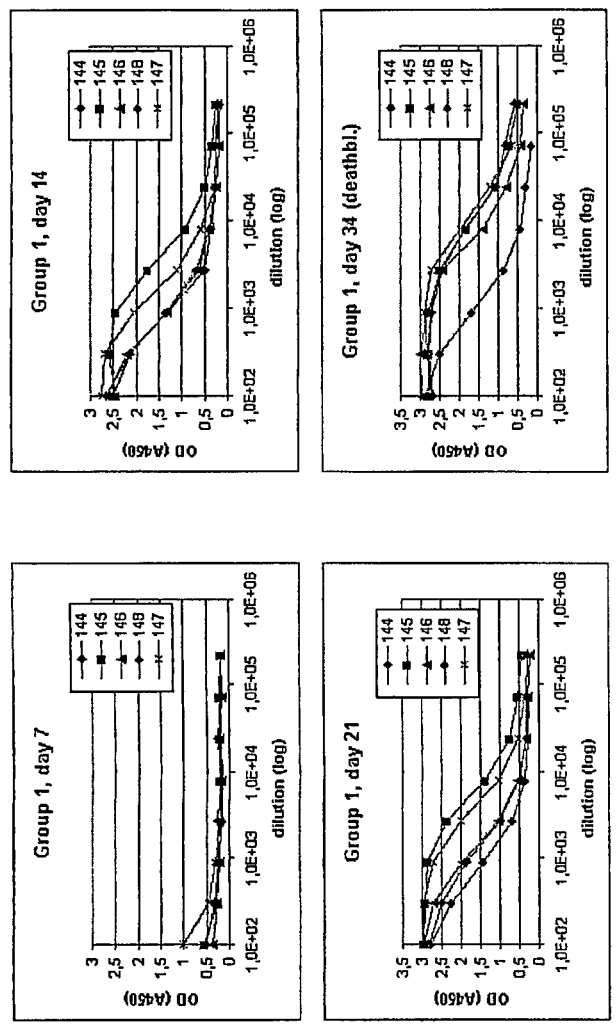
FIG. 18 shows ELISA titration curves for plasma from mice injected with $His_6$-$Z_{Taq4:1}$ as described in Example 5 when analyzed on ELISA plates coated with $His_6$-$Z_{Taq4:1}$.

The five mice that were injected with His$_6$-Z$_{Taq4:1}$ developed IgG antibodies as expected. All five mice responded by day 14 showing a maximal anti-AFFIBODY®-IgG response at day 34 (FIG. 18). In plasma samples from day 0 (before administration), no immunological response could be seen (data not shown). Table 19 shows the concentration of specific and total IgG as calculated with the XLfit program. Average concentration of specific IgG at day 34 was 85 μg/ml.

TABLE 19

Concentration of specific and total IgG in group 1
Concentration of IgG in μg/ml

| | Specific IgG | | | | Total IgG |
|---|---|---|---|---|---|
| | Day 7 | Day 14 | Day 21 | Day 34 | Day 34 |
| m. 144 | ND | 7.8 | 14.2 | 115.3 | 3706 |
| m. 145 | ND | 42.9 | 70.3 | 107.9 | 3065 |
| m. 146 | ND | 7.7 | 16.0 | 63.5 | 4306 |
| m. 147 | 0.3 | 16.7 | 49.6 | 128.9 | 3612 |
| m. 148 | ND | 8.3 | 8.0 | 10.2 | 2472 |
| average | 0.3 | 8.0 | 31.6 | 85.2 | 3432 |

(ND = not detectable)

Group 2

Figure 19:
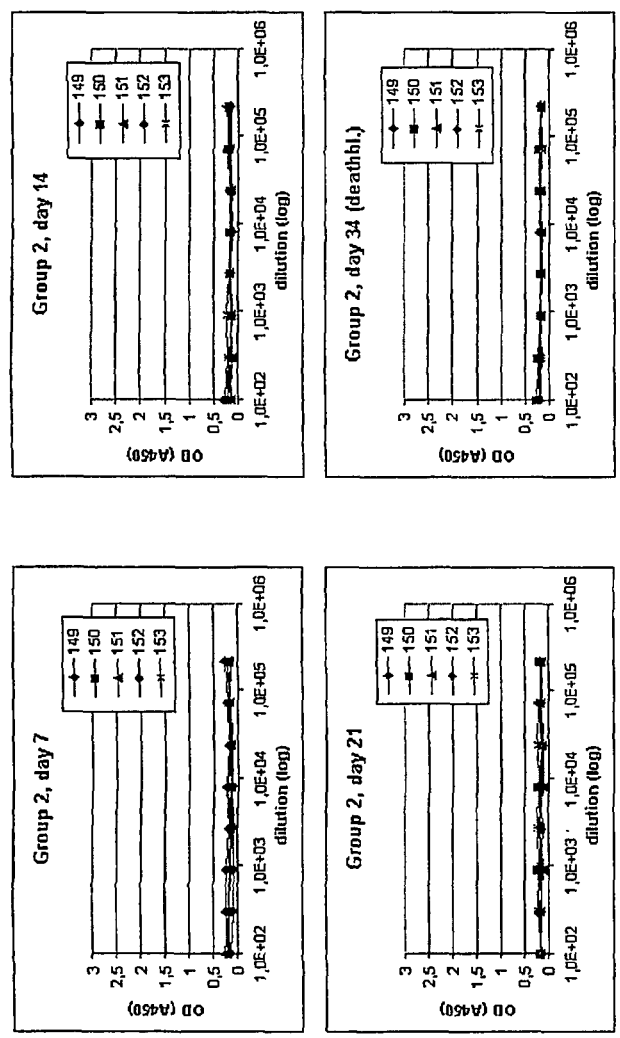
FIG. 19 shows ELISA titration curves for plasma from mice injected with $Z_{Taq4:1}$-ABD as described in Example 5 when analyzed on ELISA plates coated with $Z_{Taq4:1}$-ABD.

Group 2 consisted of five CD1 mice that were injected with Z$_{Taq4:1}$-ABD. As shown in FIG. 19. No specific antibodies could be detected in plasma samples from day 0 (data not shown) or from any other sampling day. Total IgG concentrations are shown in Table 20.

TABLE 20

Concentration of total IgG in group 2
Concentration of total IgG in μg/ml

| | Day 34 |
|---|---|
| m. 149 | 1435 |
| m. 150 | 794 |
| m. 151 | 1638 |
| m. 152 | 1050 |
| m. 153 | 2971 |
| Average | 1578 |

Treatment Scheme 2

Group 3 to 6 consisted of NMRI mice that were injected 10 times. Group 3 received His$_6$-Z$_{Taq4:1}$ at all injection times while the other groups had an injection scheme with a switch of antigen after the first 5 injections (treatment scheme 2, Table 3.3). Blood samples obtained before, during, and after immunization were analyzed on His$_6$-Z$_{Taq4:1}$ coated plates for IgG-antibodies directed against His$_6$-Z$_{Taq4:1}$. No antibody reactivity was found in any of the pre-plasma samples of group 3 to 6 (data not shown).

Group 3

Figure 20:
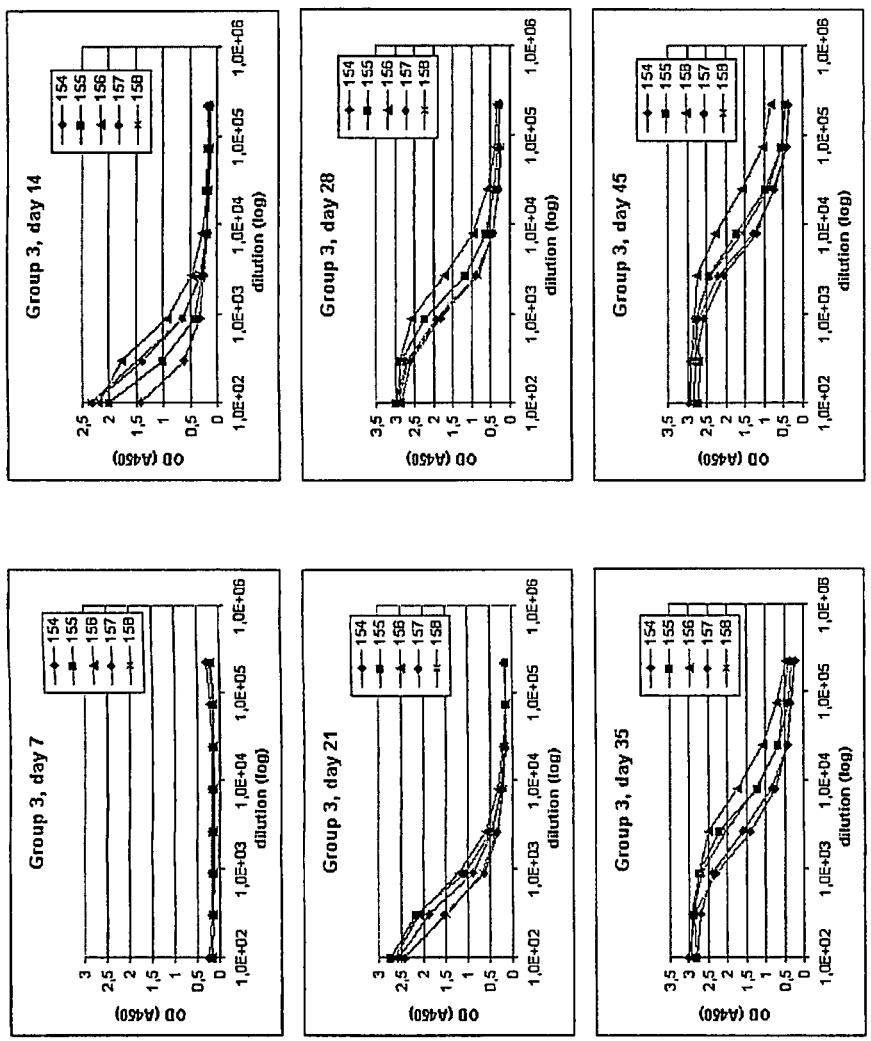
FIG. 20 shows ELISA titration curves for plasma from mice injected with $His_6$-$Z_{Taq4:1}$ as described in Example 5 when analyzed on ELISA plates coated with $His_6$-$Z_{Taq4:1}$.

Group 3 was injected with His$_6$-Z$_{Taq4:1}$ according to treatment scheme 2 (Table 18). Specific antibody production could be observed from day 14. The concentration of specific IgG increased over-time to reach a maximum in the death-bleedings (FIG. 20). These data and the concentration of total IgG are summarized in table 21. The average concentration of specific IgG at day 45 was 71 μg/ml.

TABLE 21

Concentration of specific and total IgG in group 3
Concentration of IgG in μg/ml

| | Specific IgG | | | | | | Total IgG |
|---|---|---|---|---|---|---|---|
| | Day 7 | Day 14 | Day 21 | Day 28 | Day 35 | Day 45 | Day 45 |
| m. 154 | ND | 1.0 | 4.8 | 8.3 | 18.7 | 32.6 | 2992 |
| m. 155 | ND | 1.6 | 4.7 | 10.3 | 32.7 | 65.5 | 2576 |
| m. 156 | ND | 4.0 | 6.2 | 22.1 | 68.5 | 167.5 | 5703 |
| m. 157 | ND | 2.9 | 3.1 | 9.5 | 13.7 | 35.0 | 4088 |
| m. 158 | ND | 3.3 | 2.9 | 8.7 | 34.1 | 56.1 | 2285 |
| average | ND | 2.5 | 4.3 | 11.8 | 33.5 | 71.3 | 3529 |

(ND = not detectable)

Group 4

Figure 21:
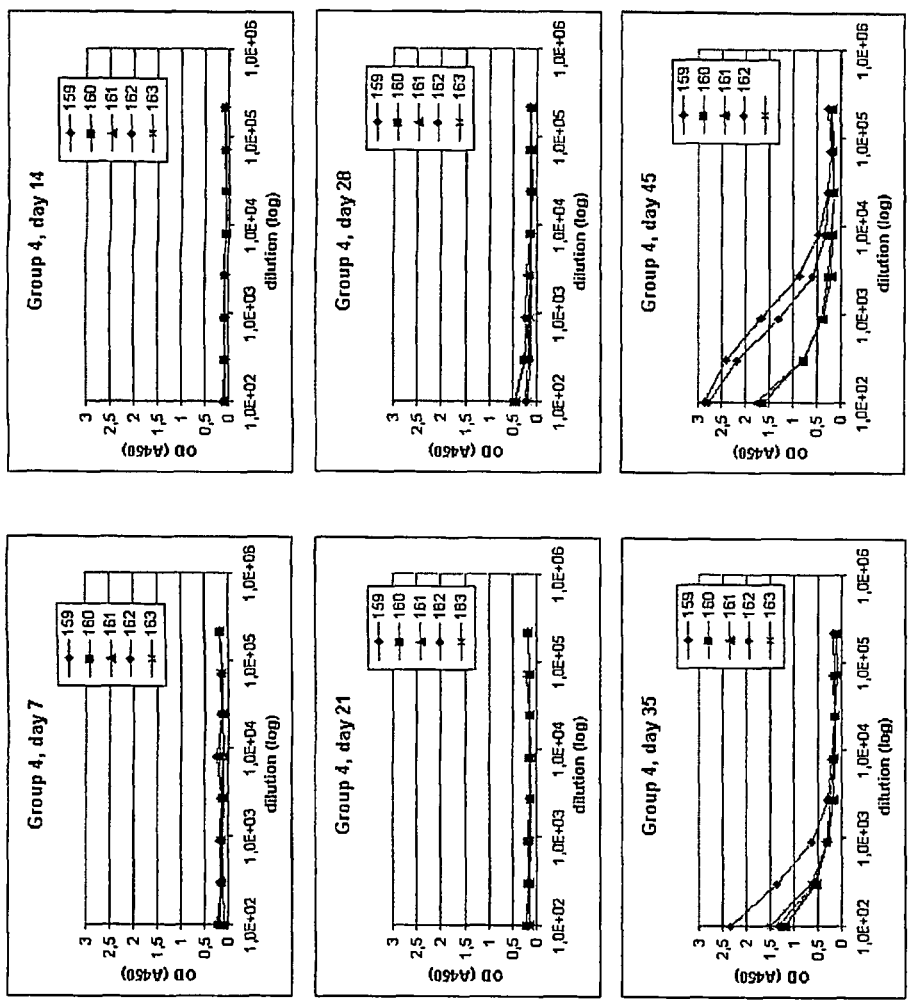
FIG. 21 shows ELISA titration curves for plasma from mice injected with $Z_{Taq4:1}$ ABD and then $His_6$-$Z_{Taq4:1}$ as described in Example 5.

Group 4 received 5 injections of Z$_{Taq4:1}$-ABD during the first 3 weeks, and then 5 additional injections of His$_6$-Z$_{Taq4:1}$. The animals did not react to the first antigen, Z$_{Taq4:1}$-ABD, but generated His$_6$-Z$_{Taq4:1}$-specific antibodies from day 35 and on. Day 35 corresponds to 14 days after the switch of injected AFFIBODY® molecule (FIG. 21). These data, and the concentration of total IgG are summarized in Table 22. The total IgG concentrations were normal except for mouse 159 that had an unusually high titre. The average concentration of specific IgG at day 45 (death-bleeding and 24 days after the switch) was 4 μg/ml.

TABLE 22

Concentration of specific and total IgG in group 4
Concentration of IgG in μg/ml

| | Specific IgG | | | | | | Total IgG |
|---|---|---|---|---|---|---|---|
| | Day 7 | Day 14 | Day 21 | Day 28 | Day 35 | Day 45 | Day 45 |
| m. 159 | ND | ND | ND | ND | 0.8 | 9.6 | 9497 |
| m. 160 | ND | ND | ND | ND | 0.7 | 1.0 | 3172 |
| m. 161 | ND | ND | ND | ND | 0.7 | 1.2 | 2554 |
| m. 162 | ND | ND | ND | ND | 2.5 | 5.6 | 3719 |
| m. 163 | ND | ND | ND | ND | 1.0 | no plasma | no plasma |
| average | ND | ND | ND | ND | 1.1 | 4.4 | 4736 |

(ND = not detectable)

Group 5

Figure 22:
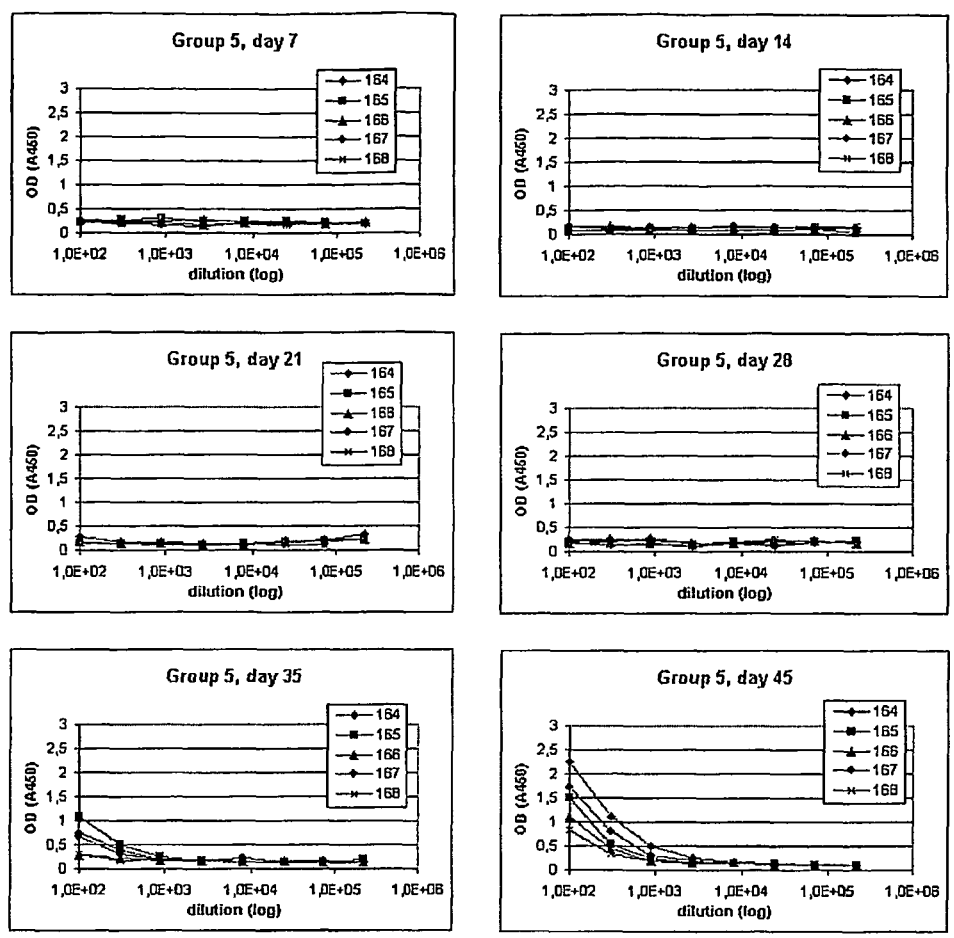
FIG. 22 shows ELISA titration curves for plasma from mice injected with $Z_{Taq4:1}$-ABD and then $Z_{Taq4:1}$-ABD and $His_6$-$Z_{Taq4:1}$ as described in Example 5.

Group 5 received five injections of Z$_{Taq4:1}$-ABD during the first 3 weeks and then another five injections of a mixture of $Z_{Taq4:1}$-ABD and $His_6$-$Z_{Taq4:1}$ (10 μg/protein). There was no detectable immune response in the animals upon injection of the first antigen i.e. $Z_{Taq4:1}$-ABD. After switching to $His_6$-$Z_{Taq4:1}$ injections low levels of specific antibodies could be detected from day 35 (FIG. 22). These data and the concentration of total IgG are summarized in table 23. The average concentration of specific IgG at day 45 was 0.8 μg/ml. The reaction is weaker than in group 4 which is most likely due to the lower dose of $His_6$-$Z_{Taq4:1}$.

TABLE 23

Concentration of specific and total IgG in group 5
Concentration of IgG in μg/ml

| | Specific IgG | | | | | Total IgG |
|---|---|---|---|---|---|---|
| | Day 7 | Day 14 | Day 21 | Day 28 | Day 35 | Day 45 | Day 45 |
| m. 164 | ND | ND | ND | ND | 0.4 | 1.5 | 2565 |
| m. 165 | ND | ND | ND | ND | 0.6 | 0.8 | 1617 |
| m. 166 | ND | ND | ND | ND | ND | 0.5 | 1284 |
| m. 167 | ND | ND | ND | ND | 0.3 | 1.1 | 1988 |
| m. 168 | ND | ND | ND | ND | ND | 0.3 | 2347 |
| Average | ND | ND | ND | ND | 0.4 | 0.8 | 1864 |

(ND = not detectable)

(ND=not detectable)
Group 6

Figure 23:
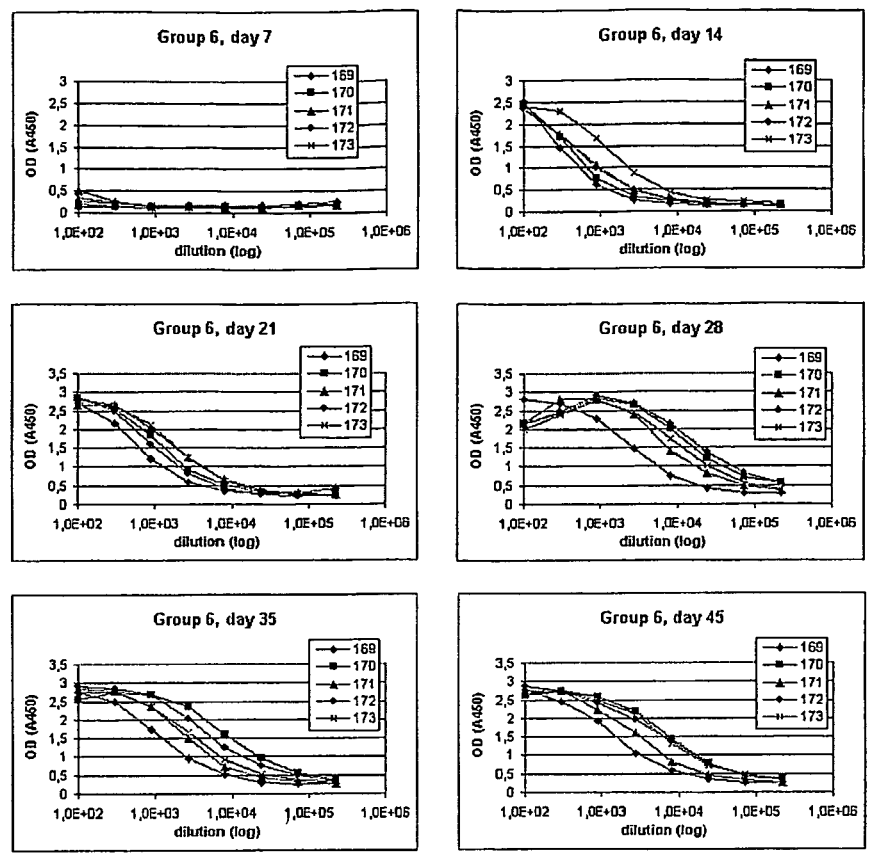
FIG. 23 shows ELISA titration curves for plasma from mice injected with $Z_{Taq4:1}$ and then $Z_{Taq4:1}$-ABD as described in Example 5.

Group 6 received five $His_6$-$Z_{Taq4:1}$ injections during the first 3 weeks followed by 5 injections of $Z_{Taq4:1}$-ABD. The results are illustrated in FIG. 23. The animal's immune system responded with a normal antibody kinetic i.e. as observed earlier upon injection of $His_6$-$Z_{Taq4:1}$. The specific IgG response reached a maximum at day 28 and decreased sometime after the antigen switch. These data and the concentration of total IgG are summarized in Table 24. The average concentration of specific IgG at day 28 was 62 μg/ml, and in the death-bleedings on day 45, 42 μg/ml.

TABLE 24

Concentration of specific and total IgG in group 6
Concentration of IgG in μg/ml

| | Specific IgG | | | | | Total IgG |
|---|---|---|---|---|---|---|
| | Day 7 | Day 14 | Day 21 | Day 28 | Day 35 | Day 45 | Day 45 |
| m. 169 | ND | 2.3 | 5.8 | 14.4 | 11.6 | 13.6 | 3295 |
| m. 170 | ND | 2.2 | 12.6 | 82.2 | 90.7 | 63.3 | 2659 |
| m. 171 | ND | 3.8 | 18.4 | 39.4 | 27.2 | 25.5 | 2737 |
| m. 172 | ND | 3.5 | 9.6 | 115.0 | 60.3 | 56.0 | 5431 |
| m. 173 | ND | 8.0 | 18.7 | 58.3 | 32.4 | 53.3 | 2941 |
| Average | ND | 4.0 | 13.0 | 61.9 | 44.4 | 42.3 | 3530 |

(ND = not detectable)

The results are illustrated in FIG. 27B.
Discussion

There were two main purposes to this study, more precisely a) to investigate the immunogenicity of $His_6$-$Z_{Taq4:1}$ and $Z_{Taq4:1}$-ABD in an additional out bred mouse strain and b) to determine whether the observed unresponsiveness of ABD-fused AFFIBODY®molecules is due to an active suppression of the animals' immune system or is merely a passive ignorance of the same.

The results showed that the out bred CD1 mice responded similar to earlier studied NMRI mice by generating specific antibodies recognizing and binding $His_6$-$Z_{Taq4:1}$ but not $Z_{Taq4:1}$-ABD. Thus the ABD-induced unresponsiveness seems to be a general phenomenon rather than a response pattern only connected to the NMRI strain.

As mentioned above, the mice in group 3 to 6 were injected with different combinations of ABD-fused and unfused $Z_{Taq4:1}$ to determine whether the ABD-mediated unresponsiveness is an active or passive process. Mice in group 4 and 5 were injected with five doses of $Z_{Taq4:1}$-ABD with the main purpose of inducing unresponsiveness and then followed by five injections of $His_6$-$Z_{Taq4:1}$ (group 4) or a mixture of $His_6$-$Z_{Taq4:1}$ and $Z_{Taq4:1}$-ABD (group 5). Both groups responded by producing a $His_6$-$Z_{Taq4:1}$ specific IgG response suggesting that injections with ABD-fused AFFIBODY®molecules do not result in an active suppression of the protein by the immune system i.e. anergy. The results of this study strongly indicate that ABD-fused AFFIBODY® molecules, by binding to serum albumin, are ignored by the mice immune system rather than actively suppressed by the same. Mice that first received $His_6$-$Z_{Taq4:1}$ continued to produce AFFIBODY®-specific IgG after the switch to $Z_{Taq4:1}$-ABD although the levels decreased slightly.

EXAMPLE 6

Immunogenicity of Chronically Administered Biologically Active Molecules in Rat

In this study, the immune responses generated in rats injected with different AFFIBODY® molecules were analyzed over an extended period. This report covers data up to 96 days after immunization. The molecules used were $(ZA\beta3)_2$ and ABD-$(ZA\beta3)_2$ as described above in Example 4. The aim of this study was to 1) analyze the ability of $(ZA\beta3)_2$ to induce specific immune responses in rats and 2) investigate if ABD-$(ZA\beta3)_2$ gives a lower immune response compared to an AFFIBODY® molecule without ABD. Blood samples obtained before, nine times during the immunization scheme and after the last injection were analyzed for reactivity. On plates coated with $(ZA\beta3)_2$ the result showed that administration with $(ZA\beta3)_2$ generated an IgG response that increased over time with a large individual variability. In contrast, there were no detectable or very low specific IgG in serum from all rats injected with ABD-fused $(ZA\beta3)_2$-molecules. In addition, no adverse effects were seen in the rats.
Methods
General ELISA Method In general, a volume of 100 μl per well was used for all incubation steps except for blocking where a volume of 200 μl was used. Plates were incubated 1 day for coating, 1-2 hours for blocking and plasma, 1 hour for second step antibody and 10 min for substrate solution. Incubations were done at room temperature except coating that was incubated at 4° C. Washing was done between all steps unless otherwise stated, using the ELISA SkanWasher 300, with 4×350 μl washing buffer (PBS-T) per well. Plates were read at 450 nm in a Tecan ELISA reader with use of the Magellan software. PBS-T buffer was used for all dilutions except coating, where coating buffer was used instead.
Rat Anti $(ZA\beta3)_2$-Specific IgG ELISA Plates were coated with 2 μg/ml of $(ZA\beta3)_2$, in coating buffer and incubated overnight at 4° C. After washing, plates were blocked as described above. Serum from rabbits injected with $(ZA\beta3)_2$ or ABD-$(ZA\beta3)_2$ was added in 3-fold dilution series starting from 1/10. After incubation, plates were washed and HRP-conjugated goat anti-rat IgG, Southern Biotechnology 3050-05 diluted 1:6000, was added. After the final incubation, plates were washed and developed as described above.

Data Analysis

Magellan2 (Tecan) was used as ELISA reader software. The results were exported to Excel for data analysis and presentation. For concentration determinations the Xlfit3.0 program, formula "Dose response-one site", equation 205 was used. Processed data from each day and type of measurement i.e. IgG, concentration etc, are represented by an Excel file.

Results

Treatment and Injection Scheme

Two groups of rats, ten per group, were injected with the same dose of AFFIBODY® molecules (200 µg/ml), about every 28 days. Serum was drawn before (day 0), according to the schedule during the injection scheme and two weeks after the last injection (death-bleeding).

TABLE 25

List of AFFIBODY ® molecules and the corresponding group-number in the study.

| Group | Treatment | Admin. | µg/animal/ injection | ml/animal/ injection | Test tube | Rat no. |
|---|---|---|---|---|---|---|
| 1 | (Zaβ3)2 | s.c. | 100 | 0.25 | A | 1-10 |
| 2 | ABD-(Zaβ3)2 | s.c. | 100 | 0.25 | B | 11-20 |

TABLE 26

Injection and bleeding scheme for group 1 and 2.

| Day | Treatment |
|---|---|
| 0 | Preserum/sample 1, Injection 1(100 µg/animal; tube A-B) |
| 3 | Injection 2 (100 µg/animal; tube A-B) |
| 6 | Injection 3 (100 µg/animal; tube A-B) |
| 7 | Sample 2 |
| 14 | Sample 3 |

TABLE 26-continued

Injection and bleeding scheme for group 1 and 2.

| Day | Treatment |
|---|---|
| 21 | Sample 4 |
| 21 | Injection 4 (100 µg/animal; tube A-B) |
| 36 | Sample 5 |
| 51 | Injection 5 (100 µg/animal; tube A-B) |
| 66 | Sample 6 |
| 81 | Injection 6 (100 µg/animal; tube A-B) |
| 96 | Sample 7 |
| 111 | Injection 7 (100 µg/animal; tube A-B) |
| 141 | Injection 8 (100 µg/animal; tube A-B) |
| 156 | Sample 8 |
| 171 | Injection 9 (100 µg/animal; tube A-B) |
| 201 | Injection 10 (100 µg/animal; tube A-B) |
| 216 | Sample 9 |
| 231 | Injection 11 (100 µg/animal; tube A-B) |
| 261 | Injection 12 (100 µg/animal; tube A-B) |
| 276 | Sample 10 |
| 291 | Injection 13 (100 µg/animal; tube A-B) |
| 306 | Sample 11 |

Injection with $(Za\beta3)_2$ and ABD-$(Za\beta3)_2$

Serum samples from individual rats were titrated in 3-fold dilution series on $(ZA\beta3)_2$ coated ELISA-plates and analyzed for the presence of specific antibodies, as described in the Methods section.

Titration Curves, $(ZA\beta3)_2$

As shown in FIG. 24 serum from rats of group one, injected with $(ZA\beta3)_2$ showed no or low response the first two weeks of immunization. After day 14, the antibody titers increased steadily and gave a widely spread response. After 96 days all rats responded although the response magnitudes were still different between individual animals.

Titration Curves, ABD-$(ZA\beta3)_2$

Figure 25:
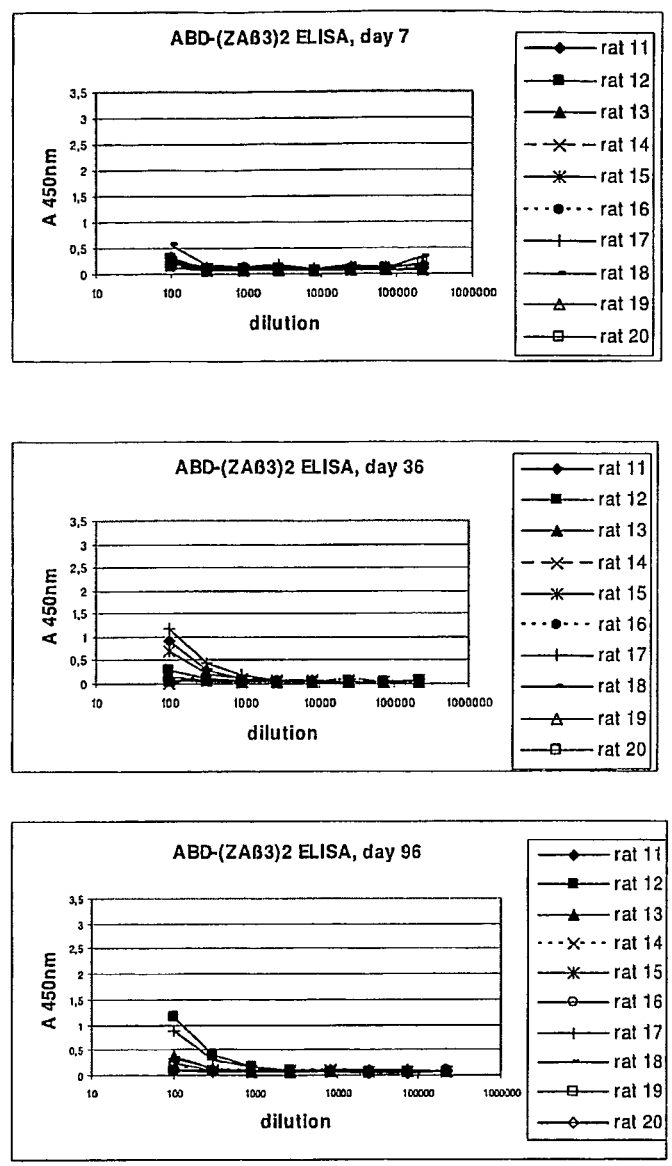
FIG. 25 shows ELISA titration curves for plasma from rats injected with ABD$(ZA\beta3)_2$ as described in Example 6.

As shown in FIG. 25 serum from rats of group two, injected with ABD-$(ZA\beta3)_2$, consistently showed no or low antibody responses when tested on $(ZA\beta3)_2$-coated plates during the 96 first days of the injection scheme.

The invention claimed is:

1. A method of reducing or eliminating the immune response elicited upon administration of a biologically active protein to a mammal, comprising coupling said biologically active protein to at least one moiety capable of binding to a serum albumin of a mammal, wherein the moiety capable of binding to a serum albumin of a mammal is the 46 amino acid ABD domain of streptococcal protein G, to form a molecule which has a binding affinity for the serum albumin such that the $K_D$ of the interaction is less than or equal to $10^{-7}$M, and wherein said molecule is capable of reducing or eliminating the immune response elicited upon administration of said biologically active protein to said mammal.

2. The method of claim 1, in which the ABD domain is arranged to enhance its binding with human serum albumin.

3. The method according to claim 2 in which the ABD domain includes an amino acid residue which forms an interaction with helix 7 in the human serum albumin domain IIB so as to enhance binding of the molecule to albumin.

4. The method according to claim 2 in which the ABD domain includes an amino acid residue which forms an interaction with residues in human serum albumin domain IIA so as to enhance binding of the molecule to albumin.

5. The method according to claim 2 in which the ABD domain includes an amino acid residue which forms an interaction with residues between helices 2 and 3 of human serum albumin so as to enhance binding of the molecule to albumin.

6. The method according to claim 1, wherein the molecule has a binding affinity for the serum albumin of less than or equal to $10^{-8}$ M.

7. The method according to claim 6, wherein the molecule has a binding affinity for the serum albumin of less than or equal to $10^{-9}$ M.

8. The method of claim 1, wherein the mammal is a human being.

9. The method according to claim 1, wherein the mammal is a non-human mammal.

10. The method according to claim 1, wherein the immune response is a humoral immune response.

11. The method according to claim 1, wherein the biological activity of the biologically active protein comprises an ability to interact with a target molecule other than a serum albumin.

12. The method according to claim 11, wherein the biological activity of the biologically active protein comprises an ability to block the activity of the target molecule.

13. The method according to claim 11, wherein the target molecule is present on the surface of a cell.

14. The method according to claim 13, wherein the cell is a cancerous or precancerous cell.

15. The method according to claim 14, wherein the target molecule present on the surface of the cell is selected from HER2, CD4, CD20, CD22, CD74, CEA and EpCAM.

16. The method according to claim 11, wherein the target molecule is selected from hormone receptors and cytokine receptors.

17. The method according to claim 1, wherein the biologically active protein is selected from antibodies, staphylococcal protein A, fibronectin, lipocalin, transferrin, and lectin.

18. The method according to claim 17, wherein the biologically active protein is staphylococcal protein A.

19. The method according to claim 18, wherein the biologically active protein comprises the B domain of staphylococcal protein A.

* * * * *

SEQUENCE LISTING

<160> NUMBER OF SEQ ID NOS: 11

<210> SEQ ID NO 1
<211> LENGTH: 11
<212> TYPE: PRT
<213> ORGANISM: Artificial
<220> FEATURE:
<223> OTHER INFORMATION: Artificial or naturally occurring

<400> SEQUENCE: 1

Asp Ile Cys Leu Pro Arg Trp Gly Cys Leu Trp
1               5                   10

<210> SEQ ID NO 2
<211> LENGTH: 11
<212> TYPE: PRT
<213> ORGANISM: Artificial
<220> FEATURE:
<223> OTHER INFORMATION: Artificial or naturally occurring

<400> SEQUENCE: 2

Asp Leu Cys Leu Arg Asp Trp Gly Cys Leu Trp
1               5                   10

```
<210> SEQ ID NO 3
<211> LENGTH: 11
<212> TYPE: PRT
<213> ORGANISM: Artificial
<220> FEATURE:
<223> OTHER INFORMATION: Artificial or naturally occurring

<400> SEQUENCE: 3

Asp Ile Cys Leu Ala Arg Trp Gly Cys Leu Trp
1               5                   10

<210> SEQ ID NO 4
<211> LENGTH: 58
<212> TYPE: PRT
<213> ORGANISM: Artificial
<220> FEATURE:
<223> OTHER INFORMATION: Artificial or naturally occurring

<400> SEQUENCE: 4

Val Asp Asn Lys Phe Asn Lys Glu Leu Arg Gln Ala Tyr Trp Glu Ile
1               5                   10                  15

Gln Ala Leu Pro Asn Leu Asn Trp Thr Gln Ser Arg Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 5
<211> LENGTH: 122
<212> TYPE: PRT
<213> ORGANISM: Artificial
<220> FEATURE:
<223> OTHER INFORMATION: Artificial or naturally occurring

<400> SEQUENCE: 5

Ala Gln His Asp Glu Ala Val Asp Asn Lys Phe Asn Lys Glu Lys Gly
1               5                   10                  15

Glu Val Val Glu Ile Phe Arg Leu Pro Asn Leu Asn Gly Arg Gln Val
            20                  25                  30

Lys Ala Phe Ile Ala Ser Leu Tyr Asp Asp Pro Ser Gln Ser Ala Asn
        35                  40                  45

Leu Leu Ala Glu Ala Lys Lys Leu Asn Asp Ala Gln Ala Pro Lys Ser
    50                  55                  60

Ser Ser Leu Ala Glu Ala Lys Val Leu Ala Asn Arg Glu Leu Asp Lys
65                  70                  75                  80

Tyr Gly Val Ser Asp Tyr Tyr Lys Asn Leu Ile Asn Asn Ala Lys Thr
                85                  90                  95

Val Glu Gly Val Lys Ala Leu Ile Asp Glu Ile Leu Ala Ala Leu Pro
            100                 105                 110

Ser Ser Ser Ala Thr Pro Ala Lys Ser Glu
        115                 120

<210> SEQ ID NO 6
<211> LENGTH: 106
<212> TYPE: PRT
<213> ORGANISM: Artificial
<220> FEATURE:
<223> OTHER INFORMATION: Artificial or naturally occurring
```

-continued

```
<400> SEQUENCE: 6

Met Gly Leu Ala Glu Ala Lys Val Leu Ala Asn Arg Glu Leu Asp Lys
1               5                   10                  15

Tyr Gly Val Ser Asp Tyr Tyr Lys Asn Leu Ile Asn Asn Ala Lys Thr
            20                  25                  30

Val Glu Gly Val Lys Ala Leu Ile Asp Glu Ile Leu Ala Ala Leu Pro
        35                  40                  45

Val Asp Asn Lys Phe Asn Lys Glu Leu Arg Gln Ala Tyr Trp Glu Ile
    50                  55                  60

Gln Ala Leu Pro Asn Leu Asn Trp Thr Gln Ser Arg Ala Phe Ile Arg
65                  70                  75                  80

Ser Leu Tyr Asp Asp Pro Ser Gln Ser Ala Asn Leu Leu Ala Glu Ala
                85                  90                  95

Lys Lys Leu Asn Asp Ala Gln Ala Pro Lys
                100                 105

<210> SEQ ID NO 7
<211> LENGTH: 164
<212> TYPE: PRT
<213> ORGANISM: Artificial
<220> FEATURE:
<223> OTHER INFORMATION: Artificial or naturally occurring

<400> SEQUENCE: 7

Met Gly Leu Ala Glu Ala Lys Val Leu Ala Asn Arg Glu Leu Asp Lys
1               5                   10                  15

Tyr Gly Val Ser Asp Tyr Tyr Lys Asn Leu Ile Asn Asn Ala Lys Thr
            20                  25                  30

Val Glu Gly Val Lys Ala Leu Ile Asp Glu Ile Leu Ala Ala Leu Pro
        35                  40                  45

Val Asp Asn Lys Phe Asn Lys Glu Leu Arg Gln Ala Tyr Trp Glu Ile
    50                  55                  60

Gln Ala Leu Pro Asn Leu Asn Trp Thr Gln Ser Arg Ala Phe Ile Arg
65                  70                  75                  80

Ser Leu Tyr Asp Asp Pro Ser Gln Ser Ala Asn Leu Leu Ala Glu Ala
                85                  90                  95

Lys Lys Leu Asn Asp Ala Gln Ala Pro Lys Val Asp Asn Lys Phe Asn
                100                 105                 110

Lys Glu Leu Arg Gln Ala Tyr Trp Glu Ile Gln Ala Leu Pro Asn Leu
            115                 120                 125

Asn Trp Thr Gln Ser Arg Ala Phe Ile Arg Ser Leu Tyr Asp Asp Pro
        130                 135                 140

Ser Gln Ser Ala Asn Leu Leu Ala Glu Ala Lys Lys Leu Asn Asp Ala
145                 150                 155                 160

Gln Ala Pro Lys

<210> SEQ ID NO 8
<211> LENGTH: 222
<212> TYPE: PRT
<213> ORGANISM: Artificial
<220> FEATURE:
<223> OTHER INFORMATION: Artificial or naturally occurring

<400> SEQUENCE: 8

Met Gly Leu Ala Glu Ala Lys Val Leu Ala Leu Arg Glu Leu Asp Lys
1               5                   10                  15

Tyr Gly Val Ser Asp Tyr Tyr Lys Asp Leu Ile Asp Lys Ala Lys Thr
            20                  25                  30
```

Val Glu Gly Val Lys Ala Leu Ile Asp Glu Ile Leu Ala Ala Leu Pro
         35                  40                  45

Val Asp Asn Lys Phe Asn Lys Glu Leu Arg Gln Ala Tyr Trp Glu Ile
 50                  55                  60

Gln Ala Leu Pro Asn Leu Asn Trp Thr Gln Ser Arg Ala Phe Ile Arg
 65                  70                  75                  80

Ser Leu Tyr Asp Asp Pro Ser Gln Ser Ala Asn Leu Leu Ala Glu Ala
                 85                  90                  95

Lys Lys Leu Asn Asp Ala Gln Ala Pro Lys Val Asp Asn Lys Phe Asn
                100                 105                 110

Lys Glu Leu Arg Gln Ala Tyr Trp Glu Ile Gln Ala Leu Pro Asn Leu
                115                 120                 125

Asn Trp Thr Gln Ser Arg Ala Phe Ile Arg Ser Leu Tyr Asp Asp Pro
        130                 135                 140

Ser Gln Ser Ala Asn Leu Leu Ala Glu Ala Lys Lys Leu Asn Asp Ala
145                 150                 155                 160

Gln Ala Pro Lys Val Asp Asn Lys Phe Asn Lys Glu Leu Arg Gln Ala
                165                 170                 175

Tyr Trp Glu Ile Gln Ala Leu Pro Asn Leu Asn Trp Thr Gln Ser Arg
            180                 185                 190

Ala Phe Ile Arg Ser Leu Tyr Asp Asp Pro Ser Gln Ser Ala Asn Leu
        195                 200                 205

Leu Ala Glu Ala Lys Lys Leu Asn Asp Ala Gln Ala Pro Lys
210                 215                 220

<210> SEQ ID NO 9
<211> LENGTH: 280
<212> TYPE: PRT
<213> ORGANISM: Artificial
<220> FEATURE:
<223> OTHER INFORMATION: Artificial or naturally occurring

<400> SEQUENCE: 9

Met Gly Leu Ala Glu Ala Lys Val Leu Ala Leu Arg Glu Leu Asp Lys
 1               5                  10                  15

Tyr Gly Val Ser Asp Tyr Tyr Lys Asp Leu Ile Asp Lys Ala Lys Thr
                 20                  25                  30

Val Glu Gly Val Lys Ala Leu Ile Asp Glu Ile Leu Ala Ala Leu Pro
         35                  40                  45

Val Asp Asn Lys Phe Asn Lys Glu Leu Arg Gln Ala Tyr Trp Glu Ile
 50                  55                  60

Gln Ala Leu Pro Asn Leu Asn Trp Thr Gln Ser Arg Ala Phe Ile Arg
 65                  70                  75                  80

Ser Leu Tyr Asp Asp Pro Ser Gln Ser Ala Asn Leu Leu Ala Glu Ala
                 85                  90                  95

Lys Lys Leu Asn Asp Ala Gln Ala Pro Lys Val Asp Asn Lys Phe Asn
                100                 105                 110

Lys Glu Leu Arg Gln Ala Tyr Trp Glu Ile Gln Ala Leu Pro Asn Leu
                115                 120                 125

Asn Trp Thr Gln Ser Arg Ala Phe Ile Arg Ser Leu Tyr Asp Asp Pro
        130                 135                 140

Ser Gln Ser Ala Asn Leu Leu Ala Glu Ala Lys Lys Leu Asn Asp Ala
145                 150                 155                 160

Gln Ala Pro Lys Val Asp Asn Lys Phe Asn Lys Glu Leu Arg Gln Ala
                165                 170                 175

```
Tyr Trp Glu Ile Gln Ala Leu Pro Asn Leu Asn Trp Thr Gln Ser Arg
            180                 185                 190
Ala Phe Ile Arg Ser Leu Tyr Asp Asp Pro Ser Gln Ser Ala Asn Leu
            195                 200                 205
Leu Ala Glu Ala Lys Lys Leu Asn Asp Ala Gln Ala Pro Lys Val Asp
            210                 215                 220
Asn Lys Phe Asn Lys Glu Leu Arg Gln Ala Tyr Trp Glu Ile Gln Ala
225                 230                 235                 240
Leu Pro Asn Leu Asn Trp Thr Gln Ser Arg Ala Phe Ile Arg Ser Leu
                245                 250                 255
Tyr Asp Asp Pro Ser Gln Ser Ala Asn Leu Leu Ala Glu Ala Lys Lys
                260                 265                 270
Leu Asn Asp Ala Gln Ala Pro Lys
            275                 280

<210> SEQ ID NO 10
<211> LENGTH: 170
<212> TYPE: PRT
<213> ORGANISM: Artificial
<220> FEATURE:
<223> OTHER INFORMATION: Artificial or naturally occurring

<400> SEQUENCE: 10

Met Gly Ser Ser Leu Ala Glu Ala Lys Val Leu Ala Asn Arg Glu Leu
1               5                   10                  15
Asp Lys Tyr Gly Val Ser Asp Tyr Tyr Lys Asn Leu Ile Asn Asn Ala
            20                  25                  30
Lys Thr Val Glu Gly Val Lys Ala Leu Ile Asp Glu Ile Leu Ala Ala
            35                  40                  45
Leu Pro Leu Gln Val Asp Asn Lys Phe Asn Lys Glu Met Ala Ser Ala
        50                  55                  60
Gly Gly Glu Ile Val Tyr Leu Pro Asn Leu Asn Pro Asp Gln Leu Ser
65              70                  75                  80
Ala Phe Ile His Ser Leu His Asp Asp Pro Ser Gln Ser Ala Asn Leu
                85                  90                  95
Leu Ala Glu Ala Lys Lys Leu Asn Asp Ala Gln Ala Pro Lys Val Asp
            100                 105                 110
Asn Lys Phe Asn Lys Glu Met Ala Ser Ala Gly Gly Glu Ile Val Tyr
            115                 120                 125
Leu Pro Asn Leu Asn Pro Asp Gln Leu Ser Ala Phe Ile His Ser Leu
            130                 135                 140
His Asp Asp Pro Ser Gln Ser Ala Asn Leu Leu Ala Glu Ala Lys Lys
145                 150                 155                 160
Leu Asn Asp Ala Gln Ala Pro Lys Val Asp
                165                 170

<210> SEQ ID NO 11
<211> LENGTH: 124
<212> TYPE: PRT
<213> ORGANISM: Artificial
<220> FEATURE:
<223> OTHER INFORMATION: Artificial or naturally occurring

<400> SEQUENCE: 11

Met Gly Ser Ser Leu Gln Val Asp Asn Lys Phe Asn Lys Glu Met Ala
1               5                   10                  15
Ser Ala Gly Gly Glu Ile Val Tyr Leu Pro Asn Leu Asn Pro Asp Gln
            20                  25                  30
```

-continued

```
Leu Ser Ala Phe Ile His Ser Leu His Asp Asp Pro Ser Gln Ser Ala
        35              40              45

Asn Leu Leu Ala Glu Ala Lys Lys Leu Asn Asp Ala Gln Ala Pro Lys
 50              55              60

Val Asp Asn Lys Phe Asn Lys Glu Met Ala Ser Ala Gly Gly Glu Ile
 65              70              75              80

Val Tyr Leu Pro Asn Leu Asn Pro Asp Gln Leu Ser Ala Phe Ile His
                85              90              95

Ser Leu His Asp Asp Pro Ser Gln Ser Ala Asn Leu Leu Ala Glu Ala
            100             105             110

Lys Lys Leu Asn Asp Ala Gln Ala Pro Lys Val Asp
        115             120
```